(12) United States Patent
Schwarz et al.

(10) Patent No.: US 11,679,255 B2
(45) Date of Patent: Jun. 20, 2023

(54) DEVICE AND METHOD FOR UNATTENDED TREATMENT OF A PATIENT

(71) Applicant: BTL Healthcare Technologies A.S., Prague (CZ)

(72) Inventors: Tomás Schwarz, Prague (CZ); Lucia Jelínková, Prague (CZ)

(73) Assignee: BTL Healthcare Technologies A.S., Prague (CZ)

( * ) Notice: Subject to any disclaimer, the term of this patent is extended or adjusted under 35 U.S.C. 154(b) by 0 days.

(21) Appl. No.: 17/930,888

(22) Filed: Sep. 9, 2022

(65) Prior Publication Data
US 2023/0001191 A1    Jan. 5, 2023

Related U.S. Application Data

(63) Continuation of application No. 17/661,406, filed on Apr. 29, 2022, now Pat. No. 11,491,329, which is a
(Continued)

(51) Int. Cl.
*A61N 1/32* (2006.01)
*A61N 1/36* (2006.01)
(Continued)

(52) U.S. Cl.
CPC ........... *A61N 1/328* (2013.01); *A61N 1/0452* (2013.01); *A61N 1/36031* (2017.08);
(Continued)

(58) Field of Classification Search
CPC .. A61N 1/328; A61N 1/0452; A61N 1/36031; A61N 1/36034; A61N 1/403
See application file for complete search history.

(56) References Cited

U.S. PATENT DOCUMENTS

| 1,973,387 A | 9/1934 | Neymann et al. |
| 2,021,676 A | 11/1935 | Wood et al. |
| (Continued) |

FOREIGN PATENT DOCUMENTS

| AU | 747678 B2 | 5/2002 |
| AU | 2011265424 B2 | 7/2014 |
| (Continued) |

OTHER PUBLICATIONS

US 10,398,895 B2, 09/2019, Schwarz (withdrawn)
(Continued)

*Primary Examiner* — Amanda K Hulbert
*Assistant Examiner* — Philip C Edwards
(74) *Attorney, Agent, or Firm* — Sterne, Kessler, Goldstein & Fox P.L.L.C.

(57) ABSTRACT

An unattended approach can increase the reproducibility and safety of the treatment as the chance of over/under treating of a certain area is significantly decreased. On the other hand, unattended treatment of uneven or rugged areas can be challenging in terms of maintaining proper distance or contact with the treated tissue, mostly on areas which tend to differ from patient to patient (e.g. facial area). Delivering energy via a system of active elements embedded in a flexible pad adhesively attached to the skin offers a possible solution. The unattended approach may include delivering of multiple energies to enhance a visual appearance.

22 Claims, 7 Drawing Sheets

Related U.S. Application Data continuation of application No. 17/576,646, filed on Jan. 14, 2022, which is a continuation of application No. PCT/IB2021/000300, filed on May 3, 2021.

(60) Provisional application No. 63/019,619, filed on May 4, 2020.

(51) Int. Cl.
*A61N 1/04* (2006.01)
*A61N 1/40* (2006.01)

(52) U.S. Cl.
CPC ........... *A61N 1/36034* (2017.08); *A61N 1/40* (2013.01); *A61N 1/403* (2013.01)

(56) References Cited

U.S. PATENT DOCUMENTS

| | | |
|---|---|---|
| 3,163,161 A | 12/1964 | Jacques et al. |
| 3,566,877 A | 3/1971 | Smith et al. |
| 3,658,051 A | 4/1972 | MacLean et al. |
| 3,841,306 A | 10/1974 | Hallgren et al. |
| 3,915,151 A | 10/1975 | Kraus |
| 3,946,349 A | 3/1976 | Haldeman, III |
| 3,952,751 A | 4/1976 | Yarger |
| 3,971,387 A | 7/1976 | Mantell |
| 4,068,292 A | 1/1978 | Berry et al. |
| 4,143,661 A | 3/1979 | LaForge et al. |
| 4,197,851 A | 4/1980 | Fellus |
| 4,237,898 A | 12/1980 | Whalley |
| 4,305,115 A | 12/1981 | Armitage |
| 4,315,503 A | 2/1982 | Ryaby et al. |
| 4,392,040 A | 7/1983 | Rand et al. |
| 4,454,883 A | 6/1984 | Fellus |
| 4,456,001 A | 6/1984 | Pescatore |
| 4,550,714 A | 11/1985 | Talish et al. |
| 4,556,056 A | 12/1985 | Fischer et al. |
| 4,665,898 A | 5/1987 | Costa et al. |
| 4,674,482 A | 6/1987 | Waltonen et al. |
| 4,674,505 A | 6/1987 | Pauli et al. |
| 4,723,536 A | 2/1988 | Rauscher et al. |
| 4,850,959 A | 7/1989 | Findl |
| 4,889,526 A | 12/1989 | Rauscher et al. |
| 4,957,480 A | 9/1990 | Morenings |
| 4,989,604 A | 2/1991 | Fang |
| 4,993,413 A | 2/1991 | McLeod et al. |
| 5,061,234 A | 10/1991 | Chaney |
| 5,067,940 A | 11/1991 | Liboff et al. |
| 5,085,626 A | 2/1992 | Frey |
| 5,143,063 A | 9/1992 | Fellner |
| 5,156,587 A | 10/1992 | Montone |
| 5,181,902 A | 1/1993 | Erickson et al. |
| 5,199,951 A | 4/1993 | Spears |
| 5,334,181 A | 8/1994 | Rubinsky et al. |
| 5,344,384 A | 9/1994 | Ostrow et al. |
| 5,401,233 A | 3/1995 | Erickson et al. |
| 5,415,617 A | 5/1995 | Kraus |
| 5,419,344 A | 5/1995 | DeWitt |
| 5,433,737 A | 7/1995 | Aimone |
| 5,433,740 A | 7/1995 | Yamaguchi |
| 5,584,863 A | 12/1996 | Rauch et al. |
| 5,620,463 A | 4/1997 | Drolet |
| 5,660,836 A | 8/1997 | Knowlton |
| 5,674,218 A | 10/1997 | Rubinsky et al. |
| 5,690,692 A | 11/1997 | Fleming |
| 5,691,873 A | 11/1997 | Masaki |
| 5,718,662 A | 2/1998 | Jalinous |
| 5,725,471 A | 3/1998 | Davey et al. |
| 5,755,753 A | 5/1998 | Knowlton |
| 5,766,124 A | 6/1998 | Polson |
| 5,782,743 A | 7/1998 | Russell |
| 5,807,232 A | 9/1998 | Espinoza et al. |
| 5,857,957 A | 1/1999 | Lin |
| 5,908,444 A | 6/1999 | Azure |
| 5,919,219 A | 7/1999 | Knowlton |
| 5,968,527 A | 10/1999 | Litovitz |
| 5,984,854 A | 11/1999 | Ishikawa et al. |
| 6,017,337 A | 1/2000 | Pira |
| 6,032,675 A | 3/2000 | Rubinsky |
| 6,038,485 A | 3/2000 | Axelgaard |
| 6,047,215 A | 4/2000 | McClure et al. |
| 6,063,108 A | 5/2000 | Salansky et al. |
| 6,067,474 A | 5/2000 | Schulman et al. |
| 6,086,525 A | 7/2000 | Davey et al. |
| 6,094,599 A | 7/2000 | Bingham et al. |
| 6,099,459 A | 8/2000 | Jacobson |
| 6,099,523 A | 8/2000 | Kim et al. |
| 6,117,066 A | 9/2000 | Abrams et al. |
| 6,132,361 A | 10/2000 | Epstein et al. |
| 6,141,985 A | 11/2000 | Cluzeau et al. |
| 6,155,966 A | 12/2000 | Parker |
| 6,161,757 A | 12/2000 | Morris |
| 6,179,769 B1 | 1/2001 | Ishikawa et al. |
| 6,179,770 B1 | 1/2001 | Mould |
| 6,179,771 B1 | 1/2001 | Mueller |
| 6,200,259 B1 | 3/2001 | March |
| 6,213,933 B1 | 4/2001 | Lin |
| 6,223,750 B1 | 5/2001 | Ishikawa et al. |
| 6,246,905 B1 | 6/2001 | Mogul |
| 6,255,815 B1 | 7/2001 | Davey |
| 6,261,301 B1 | 7/2001 | Knesch et al. |
| 6,273,862 B1 | 8/2001 | Privitera et al. |
| 6,273,884 B1 | 8/2001 | Altshuler et al. |
| 6,280,376 B1 | 8/2001 | Holcomb |
| 6,282,448 B1 | 8/2001 | Katz et al. |
| D447,806 S | 9/2001 | Davey et al. |
| 6,311,090 B1 | 10/2001 | Knowlton |
| 6,324,430 B1 | 11/2001 | Zarinetchi et al. |
| 6,324,432 B1 | 11/2001 | Rigaux et al. |
| 6,334,069 B1 | 12/2001 | George et al. |
| 6,334,074 B1 | 12/2001 | Spertell |
| 6,350,276 B1 | 2/2002 | Knowlton |
| 6,402,678 B1 | 6/2002 | Fischell et al. |
| 6,413,255 B1 | 7/2002 | Stern |
| 6,418,345 B1 | 7/2002 | Tepper et al. |
| 6,424,864 B1 | 7/2002 | Matsuura |
| 6,425,852 B1 | 7/2002 | Epstein et al. |
| 6,443,883 B1 | 9/2002 | Ostrow et al. |
| 6,445,955 B1 | 9/2002 | Michelson et al. |
| 6,447,440 B1 | 9/2002 | Markoll |
| 6,453,202 B1 | 9/2002 | Knowlton |
| 6,461,375 B1 | 10/2002 | Baudry et al. |
| 6,491,620 B1 | 12/2002 | Davey |
| 6,500,110 B1 | 12/2002 | Davey et al. |
| 6,520,903 B1 | 2/2003 | Yamashiro |
| 6,527,694 B1 | 3/2003 | Ishikawa et al. |
| 6,527,695 B1 | 3/2003 | Davey et al. |
| 6,537,197 B1 | 3/2003 | Ruohonen et al. |
| 6,569,078 B2 | 5/2003 | Ishikawa et al. |
| 6,605,080 B1 | 8/2003 | Altshuler et al. |
| 6,635,053 B1 | 10/2003 | Lalonde et al. |
| 6,658,301 B2 | 12/2003 | Loeb et al. |
| 6,662,054 B2 | 12/2003 | Kreindel et al. |
| 6,663,556 B2 | 12/2003 | Barker |
| 6,663,659 B2 | 12/2003 | McDaniel |
| 6,701,185 B2 | 3/2004 | Burnett et al. |
| 6,735,481 B1 | 5/2004 | Bingham et al. |
| 6,738,667 B2 | 5/2004 | Deno et al. |
| 6,749,624 B2 | 6/2004 | Knowlton |
| 6,827,681 B2 | 12/2004 | Tanner et al. |
| 6,849,040 B2 | 2/2005 | Ruohonen et al. |
| 6,860,852 B2 | 3/2005 | Schonenberger et al. |
| 6,871,099 B1 | 3/2005 | Whitehurst et al. |
| 6,879,859 B1 | 4/2005 | Boveja |
| 6,889,090 B2 | 5/2005 | Kreindel |
| 6,920,883 B2 | 7/2005 | Bessette et al. |
| 6,939,287 B1 | 9/2005 | Ardizzone et al. |
| 6,960,202 B2 | 11/2005 | Cluzeau et al. |
| 6,990,427 B2 | 1/2006 | Kirsch et al. |
| 7,024,239 B2 | 4/2006 | George et al. |
| 7,030,764 B2 | 4/2006 | Smith et al. |
| 7,041,100 B2 | 5/2006 | Kreindel |
| 7,083,580 B2 | 8/2006 | Bernabei |
| 7,186,209 B2 | 3/2007 | Jacobson et al. |

(56) References Cited

U.S. PATENT DOCUMENTS

| | | | |
|---|---|---|---|
| 7,217,265 B2 | 5/2007 | Hennings et al. | |
| 7,276,058 B2 | 10/2007 | Altshuler et al. | |
| 7,309,309 B2 | 12/2007 | Wang et al. | |
| 7,318,821 B2 | 1/2008 | Lalonde et al. | |
| 7,351,252 B2 | 4/2008 | Altshuler et al. | |
| 7,367,341 B2 | 5/2008 | Anderson et al. | |
| 7,369,895 B2 | 5/2008 | Hurtado | |
| 7,372,271 B2 | 5/2008 | Roozen et al. | |
| 7,376,460 B2 | 5/2008 | Bernabei | |
| 7,396,326 B2 | 7/2008 | Ghiron et al. | |
| 7,496,401 B2 | 2/2009 | Bernabei | |
| 7,520,849 B1 | 4/2009 | Simon | |
| 7,520,875 B2 | 4/2009 | Bernabei | |
| 7,532,926 B2 | 5/2009 | Bernabei | |
| 7,571,003 B2 | 8/2009 | Pozzato | |
| 7,591,776 B2 | 9/2009 | Phillips et al. | |
| 7,601,115 B2 | 10/2009 | Riehl | |
| 7,608,035 B2 | 10/2009 | Farone | |
| 7,618,429 B2 | 11/2009 | Mulholland | |
| 7,630,774 B2 | 12/2009 | Karni et al. | |
| 7,643,883 B2 | 1/2010 | Kreindel | |
| 7,697,998 B2 | 4/2010 | Axelgaard | |
| 7,699,768 B2 | 4/2010 | Kishawi et al. | |
| 7,740,574 B2 | 6/2010 | Pilla et al. | |
| 7,744,523 B2 | 6/2010 | Epstein | |
| 7,783,348 B2 | 8/2010 | Gill et al. | |
| 7,785,358 B2 | 8/2010 | Lach | |
| 7,854,754 B2 | 12/2010 | Ting et al. | |
| 7,909,786 B2 | 3/2011 | Bonnefin et al. | |
| 7,914,469 B2 | 3/2011 | Torbati | |
| 7,945,321 B2 | 5/2011 | Bernabei | |
| 7,946,973 B2 | 5/2011 | Peterchev | |
| 7,953,500 B2 | 5/2011 | Bingham et al. | |
| 7,998,053 B2 | 8/2011 | Aho | |
| 8,035,385 B2 | 10/2011 | Tomiha et al. | |
| RE43,007 E | 12/2011 | Lalonde et al. | |
| 8,088,058 B2 | 1/2012 | Juliana et al. | |
| 8,128,549 B2 | 3/2012 | Testani et al. | |
| 8,133,191 B2 | 3/2012 | Rosenberg et al. | |
| 8,137,258 B1 | 3/2012 | Dennis et al. | |
| 8,172,835 B2 | 5/2012 | Leyh et al. | |
| 8,192,474 B2 | 6/2012 | Levinson | |
| 8,204,446 B2 | 6/2012 | Scheer et al. | |
| 8,251,986 B2 | 8/2012 | Chornenky et al. | |
| 8,265,763 B2 | 9/2012 | Fahey | |
| 8,271,090 B1 | 9/2012 | Hartman et al. | |
| 8,275,442 B2 | 9/2012 | Allison | |
| 8,285,390 B2 | 10/2012 | Levinson et al. | |
| 8,335,566 B2 | 12/2012 | Muller et al. | |
| 8,337,539 B2 | 12/2012 | Ting et al. | |
| 8,366,756 B2 | 2/2013 | Tucek et al. | |
| 8,376,825 B2 | 2/2013 | Guinn et al. | |
| 8,376,925 B1 | 2/2013 | Dennis et al. | |
| 8,454,591 B2 | 6/2013 | Leyh et al. | |
| 8,457,751 B2 | 6/2013 | Pozzato | |
| 8,475,354 B2 | 7/2013 | Phillips et al. | |
| 8,493,286 B1 * | 7/2013 | Agrama | A61N 1/36034 382/118 |
| 8,523,927 B2 | 9/2013 | Levinson et al. | |
| 8,548,599 B2 | 10/2013 | Zarsky et al. | |
| 8,565,888 B2 | 10/2013 | Buhlmann et al. | |
| 8,579,953 B1 | 11/2013 | Dunbar et al. | |
| 8,588,930 B2 | 11/2013 | DiUbaldi et al. | |
| 8,593,245 B2 | 11/2013 | Zeng et al. | |
| 8,603,073 B2 | 12/2013 | Allison | |
| 8,646,239 B2 | 2/2014 | Rulon | |
| 8,666,492 B2 | 3/2014 | Muller et al. | |
| 8,676,338 B2 | 3/2014 | Levinson | |
| 8,684,901 B1 | 4/2014 | Zabara | |
| 8,700,176 B2 | 4/2014 | Azar et al. | |
| 8,702,774 B2 | 4/2014 | Baker et al. | |
| 8,725,270 B2 | 5/2014 | Towe | |
| 8,771,326 B2 | 7/2014 | Myeong et al. | |
| 8,788,060 B2 | 7/2014 | Nebrigic et al. | |
| 8,795,148 B2 | 8/2014 | Schneider et al. | |
| 8,834,547 B2 | 9/2014 | Anderson et al. | |
| 8,840,608 B2 | 9/2014 | Anderson et al. | |
| 8,864,641 B2 | 10/2014 | Riehl et al. | |
| 8,868,177 B2 | 10/2014 | Simon et al. | |
| 8,906,009 B2 | 12/2014 | Nebrigic et al. | |
| 8,915,948 B2 | 12/2014 | Altshuler et al. | |
| 8,932,338 B2 | 1/2015 | Lim et al. | |
| 8,979,727 B2 | 3/2015 | Ron et al. | |
| 8,985,331 B2 | 3/2015 | Guenter et al. | |
| 8,998,791 B2 | 4/2015 | Ron Edoute et al. | |
| 9,002,477 B2 | 4/2015 | Burnett | |
| 9,008,793 B1 * | 4/2015 | Cosman, Sr. | A61B 18/1206 607/101 |
| 9,028,469 B2 | 5/2015 | Jones et al. | |
| 9,037,247 B2 | 5/2015 | Simon et al. | |
| 9,044,595 B2 | 6/2015 | Araya et al. | |
| 9,061,128 B2 | 6/2015 | Hall et al. | |
| 9,072,891 B1 | 7/2015 | Rao | |
| 9,078,634 B2 | 7/2015 | Gonzales et al. | |
| 9,089,719 B2 | 7/2015 | Simon et al. | |
| 9,101,524 B2 | 8/2015 | Aghion | |
| 9,132,031 B2 | 9/2015 | Levinson et al. | |
| 9,149,650 B2 | 10/2015 | Shanks et al. | |
| 9,168,096 B2 | 10/2015 | Kreindel | |
| 9,233,257 B1 | 1/2016 | Zabara | |
| 9,254,395 B1 | 2/2016 | Shambayati | |
| 9,261,574 B2 | 2/2016 | Boskamp et al. | |
| 9,265,690 B2 | 2/2016 | Kriksunov et al. | |
| 9,308,120 B2 | 4/2016 | Anderson et al. | |
| 9,314,368 B2 | 4/2016 | Allison et al. | |
| 9,326,910 B2 | 5/2016 | Eckhouse et al. | |
| 9,339,641 B2 | 5/2016 | Rajguru et al. | |
| 9,358,068 B2 | 6/2016 | Schomacker et al. | |
| 9,358,149 B2 | 6/2016 | Anderson et al. | |
| 9,375,345 B2 | 6/2016 | Levinson et al. | |
| 9,387,339 B2 | 7/2016 | Sham et al. | |
| 9,398,975 B2 | 7/2016 | Moller et al. | |
| 9,408,745 B2 | 8/2016 | Levinson et al. | |
| 9,414,759 B2 | 8/2016 | Lang et al. | |
| 9,433,797 B2 | 9/2016 | Pilla et al. | |
| 9,439,805 B2 | 9/2016 | Gonzales et al. | |
| 9,446,258 B1 | 9/2016 | Schwarz | |
| 9,468,774 B2 | 10/2016 | Arsk et al. | |
| 9,532,832 B2 | 1/2017 | Ron Edoute et al. | |
| 9,545,523 B2 | 1/2017 | Nanda | |
| 9,561,357 B2 | 2/2017 | Hall et al. | |
| 9,586,057 B2 | 3/2017 | Ladman et al. | |
| 9,596,920 B2 | 3/2017 | Shalev et al. | |
| 9,610,429 B2 | 4/2017 | Harris et al. | |
| 9,610,459 B2 | 4/2017 | Burnett et al. | |
| 9,615,854 B2 | 4/2017 | Matsushita | |
| 9,636,516 B2 | 5/2017 | Schwarz | |
| 9,636,519 B2 | 5/2017 | Ladman et al. | |
| 9,649,220 B2 | 5/2017 | Anderson et al. | |
| 9,655,770 B2 | 5/2017 | Levinson et al. | |
| 9,694,194 B2 | 7/2017 | Ron Edoute et al. | |
| 9,737,238 B2 | 8/2017 | Wright et al. | |
| 9,737,434 B2 | 8/2017 | Allison | |
| 9,757,584 B2 | 9/2017 | Burnett | |
| 9,782,324 B2 | 10/2017 | Crunick et al. | |
| 9,814,897 B2 | 11/2017 | Ron Edoute et al. | |
| 9,844,460 B2 | 12/2017 | Weber et al. | |
| 9,844,461 B2 | 12/2017 | Levinson et al. | |
| 9,855,166 B2 | 1/2018 | Anderson et al. | |
| 9,861,421 B2 | 1/2018 | O'Neil et al. | |
| 9,861,520 B2 | 1/2018 | Baker et al. | |
| 9,867,996 B2 | 1/2018 | Zarsky et al. | |
| 9,901,743 B2 | 2/2018 | Ron Edoute et al. | |
| 9,919,161 B2 | 3/2018 | Schwarz | |
| 9,937,358 B2 | 4/2018 | Schwarz | |
| 9,962,553 B2 | 5/2018 | Schwarz et al. | |
| 9,968,797 B2 | 5/2018 | Sham et al. | |
| 9,974,519 B1 | 5/2018 | Schwarz | |
| 9,974,684 B2 | 5/2018 | Anderson et al. | |
| 9,980,765 B2 | 5/2018 | Avram et al. | |
| 9,981,143 B2 | 5/2018 | Ron Edoute et al. | |
| 9,999,780 B2 | 6/2018 | Weyh et al. | |
| 10,037,867 B2 | 7/2018 | Godyak | |
| 10,039,929 B1 | 8/2018 | Schwarz et al. | |

(56) References Cited

U.S. PATENT DOCUMENTS

| | | |
|---|---|---|
| 10,080,906 B2 | 9/2018 | Schwarz |
| 10,092,346 B2 | 10/2018 | Levinson |
| 10,111,770 B2 | 10/2018 | Harris et al. |
| 10,111,774 B2 | 10/2018 | Gonzales et al. |
| 10,124,187 B2 | 11/2018 | Schwarz et al. |
| 10,183,172 B2 | 1/2019 | Ghiron et al. |
| 10,195,453 B2 | 2/2019 | Schwarz et al. |
| 10,195,454 B2 | 2/2019 | Yamashiro |
| 10,201,380 B2 | 2/2019 | Debenedictis et al. |
| 10,245,439 B1 | 4/2019 | Schwarz et al. |
| 10,271,900 B2 | 4/2019 | Marchitto et al. |
| 10,342,988 B2 | 7/2019 | Midorikawa et al. |
| 10,413,745 B2 | 9/2019 | Riehl |
| 10,463,869 B2 | 11/2019 | Ron Edoute et al. |
| 10,471,269 B1 | 11/2019 | Schwarz et al. |
| 10,478,588 B2 | 11/2019 | Walpole et al. |
| 10,478,633 B2 | 11/2019 | Schwarz et al. |
| 10,478,634 B2 | 11/2019 | Schwarz et al. |
| 10,493,293 B2 | 12/2019 | Schwarz et al. |
| 10,518,098 B2 | 12/2019 | Hong et al. |
| 10,549,109 B2 | 2/2020 | Schwarz et al. |
| 10,549,110 B1 | 2/2020 | Schwarz et al. |
| 10,556,121 B2 | 2/2020 | Gurfein |
| 10,556,122 B1 | 2/2020 | Schwarz et al. |
| 10,569,094 B2 | 2/2020 | Schwarz et al. |
| 10,569,095 B1 | 2/2020 | Schwarz et al. |
| 10,583,287 B2 | 3/2020 | Schwarz |
| 10,596,386 B2 | 3/2020 | Schwarz et al. |
| 10,610,696 B1 | 4/2020 | Peled |
| 10,632,321 B2 | 4/2020 | Schwarz et al. |
| 10,639,490 B2 | 5/2020 | Simon et al. |
| 10,675,819 B2 | 6/2020 | Li et al. |
| 10,688,310 B2 | 6/2020 | Schwarz et al. |
| 10,695,575 B1 | 6/2020 | Schwarz et al. |
| 10,695,576 B2 | 6/2020 | Schwarz et al. |
| 10,709,894 B2 | 7/2020 | Schwarz et al. |
| 10,709,895 B2 | 7/2020 | Schwarz et al. |
| 10,806,943 B2 | 10/2020 | Sokolowski |
| 10,821,295 B1 | 11/2020 | Schwarz et al. |
| 10,849,784 B2 | 12/2020 | Jurna et al. |
| 11,141,219 B1 | 10/2021 | Schwarz |
| 11,185,690 B2 | 11/2021 | Schwarz |
| 11,247,039 B2 | 2/2022 | Schwarz |
| 2001/0018547 A1 | 8/2001 | Mechlenburg et al. |
| 2002/0128686 A1 | 9/2002 | Minogue et al. |
| 2002/0143365 A1 | 10/2002 | Herbst |
| 2003/0032900 A1 | 2/2003 | Ella |
| 2003/0078646 A1 | 4/2003 | Axelgaard |
| 2003/0093133 A1 | 5/2003 | Crowe et al. |
| 2003/0216729 A1 | 11/2003 | Marchitto et al. |
| 2004/0034346 A1 | 2/2004 | Stern et al. |
| 2004/0039279 A1 | 2/2004 | Ruohonen |
| 2004/0077977 A1 | 4/2004 | Ella et al. |
| 2004/0210282 A1 | 10/2004 | Flock et al. |
| 2005/0038313 A1 | 2/2005 | Ardizzone |
| 2005/0107656 A1 | 5/2005 | Jang et al. |
| 2005/0187599 A1 | 8/2005 | Sharkey et al. |
| 2006/0094924 A1 | 5/2006 | Riehl |
| 2006/0293719 A1 | 12/2006 | Naghavi |
| 2007/0016274 A1 | 1/2007 | Boveja et al. |
| 2007/0027411 A1 | 2/2007 | Ella et al. |
| 2007/0088419 A1 | 4/2007 | Fiorina et al. |
| 2007/0142886 A1 | 6/2007 | Fischell et al. |
| 2007/0179534 A1 | 8/2007 | Firlik et al. |
| 2007/0293918 A1 | 12/2007 | Thompson et al. |
| 2008/0046053 A1 | 2/2008 | Wagner et al. |
| 2008/0082153 A1 | 4/2008 | Gadsby et al. |
| 2009/0099405 A1 | 4/2009 | Schneider et al. |
| 2009/0118790 A1 | 5/2009 | Van Herk |
| 2009/0270945 A1 | 10/2009 | Markoll et al. |
| 2010/0036191 A1 | 2/2010 | Walter et al. |
| 2010/0185042 A1 | 7/2010 | Schneider et al. |
| 2010/0256438 A1 | 10/2010 | Mishelevich et al. |
| 2010/0256439 A1 | 10/2010 | Schneider et al. |
| 2010/0261992 A1 | 10/2010 | Axelgaard |
| 2010/0274327 A1 | 10/2010 | Carroll et al. |
| 2010/0286470 A1 | 11/2010 | Schneider et al. |
| 2010/0298623 A1 | 11/2010 | Mishelevich et al. |
| 2010/0331602 A1 | 12/2010 | Mishelevich et al. |
| 2011/0105826 A1 | 5/2011 | Mishelevich et al. |
| 2011/0118722 A1 | 5/2011 | Lischinsky et al. |
| 2011/0196438 A1 | 8/2011 | Mnozil et al. |
| 2011/0237921 A1 | 9/2011 | Askin, III et al. |
| 2011/0273251 A1 | 11/2011 | Mishelevich et al. |
| 2011/0275927 A1 | 11/2011 | Wagner et al. |
| 2011/0276108 A1 | 11/2011 | Crowe et al. |
| 2011/0319700 A1 | 12/2011 | Schneider |
| 2012/0035608 A1 | 2/2012 | Marchitto et al. |
| 2012/0101326 A1 | 4/2012 | Simon et al. |
| 2012/0226330 A1 | 9/2012 | Kolen et al. |
| 2012/0253098 A1 | 10/2012 | George et al. |
| 2012/0259382 A1* | 10/2012 | Trier .................. A61N 1/36071 607/46 |
| 2012/0303076 A1 | 11/2012 | Fahey |
| 2012/0310035 A1 | 12/2012 | Schneider et al. |
| 2013/0006039 A1 | 1/2013 | Sadler |
| 2013/0096363 A1 | 4/2013 | Schneider et al. |
| 2013/0289433 A1 | 10/2013 | Jin et al. |
| 2014/0005759 A1 | 1/2014 | Fahey et al. |
| 2014/0012064 A1 | 1/2014 | Riehl et al. |
| 2014/0221990 A1 | 8/2014 | Kreindel |
| 2014/0235928 A1 | 8/2014 | Zangen et al. |
| 2014/0249355 A1 | 9/2014 | Martinez |
| 2014/0249601 A1 | 9/2014 | Bachinski et al. |
| 2014/0324120 A1 | 10/2014 | Bogie et al. |
| 2014/0357935 A1 | 12/2014 | Ilmoniemi et al. |
| 2015/0005569 A1 | 1/2015 | Missoli |
| 2015/0005759 A1 | 1/2015 | Welches et al. |
| 2015/0018667 A1 | 1/2015 | Radman et al. |
| 2015/0094788 A1 | 4/2015 | Pierenkemper |
| 2015/0133718 A1 | 5/2015 | Schneider et al. |
| 2015/0148858 A1 | 5/2015 | Kaib |
| 2016/0136462 A1 | 5/2016 | Lewis, Jr. et al. |
| 2016/0220834 A1 | 8/2016 | Schwarz |
| 2016/0317827 A1 | 11/2016 | Schwarz |
| 2017/0001026 A1 | 1/2017 | Schwarz |
| 2017/0036019 A1 | 2/2017 | Matsushita |
| 2017/0106203 A1 | 4/2017 | Schneider et al. |
| 2017/0333705 A1 | 11/2017 | Schwarz |
| 2017/0348539 A1* | 12/2017 | Schwarz ................ A61N 1/328 |
| 2017/0361095 A1 | 12/2017 | Mueller et al. |
| 2018/0000347 A1 | 1/2018 | Perez et al. |
| 2018/0021565 A1 | 1/2018 | Dar et al. |
| 2018/0036548 A1 | 2/2018 | Nusse |
| 2018/0043151 A1 | 2/2018 | Ejiri et al. |
| 2018/0071544 A1 | 3/2018 | Ghiron et al. |
| 2018/0177706 A1 | 6/2018 | Gozani et al. |
| 2018/0229048 A1* | 8/2018 | Sikora ................... A61N 2/002 |
| 2018/0296831 A1 | 10/2018 | Matsushita |
| 2018/0353767 A1 | 12/2018 | Biginton |
| 2019/0111255 A1 | 4/2019 | Errico et al. |
| 2019/0117965 A1 | 4/2019 | Iger et al. |
| 2019/0168012 A1 | 6/2019 | Biginton |
| 2019/0192853 A1 | 6/2019 | Kim et al. |
| 2019/0209836 A1 | 7/2019 | Yakoub et al. |
| 2019/0255346 A1 | 8/2019 | Ghiron |
| 2019/0269909 A1 | 9/2019 | Gozani et al. |
| 2019/0275320 A1 | 9/2019 | Kim et al. |
| 2020/0094066 A1 | 3/2020 | Heath |
| 2020/0114160 A1 | 4/2020 | Blendermann |
| 2020/0171297 A1 | 6/2020 | Kirson et al. |
| 2020/0197696 A1 | 6/2020 | Nagel et al. |
| 2020/0330782 A1 | 10/2020 | Zabara |
| 2020/0352633 A1 | 11/2020 | Treen et al. |
| 2020/0353244 A1 | 11/2020 | Yamazaki |
| 2020/0353273 A1 | 11/2020 | Zucco |
| 2020/0360681 A1 | 11/2020 | Lay |
| 2021/0008369 A1 | 1/2021 | Crosson |
| 2021/0038894 A1 | 2/2021 | Mowery et al. |
| 2021/0146150 A1 | 5/2021 | Frangineas, Jr. et al. |
| 2021/0275825 A1 | 9/2021 | Kreindel |
| 2021/0283395 A1 | 9/2021 | Kreindel |

(56) References Cited

U.S. PATENT DOCUMENTS

| | | | |
|---|---|---|---|
| 2021/0361938 A1 | 11/2021 | Gershonowitz | |
| 2022/0249836 A1 | 8/2022 | Schwartz | |

FOREIGN PATENT DOCUMENTS

| | | |
|---|---|---|
| AU | 2012244313 B2 | 11/2014 |
| AU | 2014203094 B2 | 7/2015 |
| AU | 2013207657 B2 | 11/2015 |
| BR | PI0812502 A2 | 6/2015 |
| CA | 2484880 A1 | 4/2006 |
| CA | 2604112 C | 7/2016 |
| CA | 3019140 A1 | 10/2017 |
| CA | 3019410 A1 | 10/2017 |
| CA | 3023821 A1 | 11/2017 |
| CH | 714113 A2 | 3/2019 |
| CN | 86204070 U | 9/1987 |
| CN | 87203746 U | 12/1987 |
| CN | 87215926 U | 7/1988 |
| CN | 1026953 C | 12/1994 |
| CN | 1027958 C | 3/1995 |
| CN | 2192348 Y | 3/1995 |
| CN | 1206975 C | 6/2005 |
| CN | 101234231 A | 8/2008 |
| CN | 101327358 A | 12/2008 |
| CN | 201906360 U | 7/2011 |
| CN | 102319141 A | 1/2012 |
| CN | 102711706 A | 10/2012 |
| CN | 10284 7231 A | 1/2013 |
| CN | 202637725 U | 1/2013 |
| CN | 203169831 U | 9/2013 |
| CN | 102319141 B | 8/2014 |
| CN | 106540375 A | 3/2017 |
| CN | 107613914 A | 1/2018 |
| CN | 108882992 A | 11/2018 |
| CN | 109310516 A | 2/2019 |
| CN | 112221015 A | 1/2021 |
| DE | 718637 C | 3/1942 |
| DE | 1118902 B | 12/1961 |
| DE | 2748780 A1 | 5/1978 |
| DE | 3205048 A | 8/1983 |
| DE | 334097 4 A1 | 5/1985 |
| DE | 3610474 A1 | 10/1986 |
| DE | 3825165 A1 | 1/1990 |
| DE | 334097 4 C2 | 7/1994 |
| DE | 69318706 T2 | 1/1999 |
| DE | 10062050 A1 | 4/2002 |
| DE | 102004006192 A1 | 9/2005 |
| DE | 60033756 T2 | 6/2007 |
| DE | 102009023855 A1 | 12/2010 |
| DE | 102009050010 A1 | 5/2011 |
| DE | 102010004307 A1 | 7/2011 |
| DE | 102011014291 A1 | 9/2012 |
| DE | 102013211859 B4 | 7/2015 |
| DE | 102016116399 A1 | 3/2018 |
| DE | 202016008884 U1 | 7/2020 |
| DE | 102010014157 B4 | 2/2021 |
| DK | 0633008 T3 | 3/1999 |
| EA | 000494 B1 | 8/1999 |
| EA | 002087 B1 | 12/2001 |
| EA | 002179 B1 | 2/2002 |
| EA | 003851 B1 | 10/2003 |
| EA | 007347 B1 | 8/2006 |
| EA | 007975 B1 | 2/2007 |
| EP | 0048451 A1 | 3/1982 |
| EP | 0209246 A1 | 1/1987 |
| EP | 0459101 A1 | 12/1991 |
| EP | 0459401 A1 | 12/1991 |
| EP | 0633008 A1 | 1/1995 |
| EP | 0788813 A1 | 8/1997 |
| EP | 0633008 B1 | 5/1998 |
| EP | 0692993 B1 | 9/1999 |
| EP | 1022034 A1 | 7/2000 |
| EP | 1916013 A1 | 4/2008 |
| EP | 2069014 A2 | 6/2009 |
| EP | 2139560 A1 | 1/2010 |
| EP | 2124800 B1 | 11/2010 |
| EP | 1917935 B1 | 1/2011 |
| EP | 2308559 A2 | 4/2011 |
| EP | 2139560 B1 | 5/2012 |
| EP | 2461765 A1 | 6/2012 |
| EP | 2069014 B1 | 6/2013 |
| EP | 2614807 A1 | 7/2013 |
| EP | 2676700 A2 | 12/2013 |
| EP | 2694159 A2 | 2/2014 |
| EP | 2749259 A1 | 7/2014 |
| EP | 2814445 A1 | 12/2014 |
| EP | 2856986 A1 | 4/2015 |
| EP | 3009167 A1 | 4/2016 |
| EP | 2501352 B1 | 7/2016 |
| EP | 3209246 A1 | 8/2017 |
| EP | 3342379 A1 | 7/2018 |
| EP | 3389532 A1 | 10/2018 |
| EP | 3434323 A1 | 1/2019 |
| EP | 3721939 A1 | 10/2020 |
| ES | 2118925 T3 | 10/1998 |
| ES | 2300569 T3 | 6/2008 |
| ES | 2305698 T3 | 11/2008 |
| ES | 2359581 T3 | 5/2011 |
| ES | 2533145 A2 | 4/2015 |
| ES | 2533145 B1 | 7/2016 |
| ES | 2533145 R1 | 10/2018 |
| FR | 3041881 A | 4/2017 |
| FR | 3061012 A1 | 6/2018 |
| GB | 260116 A | 10/1926 |
| GB | 304587 A | 3/1930 |
| GB | 390500 A | 4/1933 |
| GB | 871672 A | 6/1961 |
| GB | 2176009 A | 12/1986 |
| GB | 2188238 A | 9/1987 |
| GB | 2176009 B | 12/1989 |
| GB | 2261820 A | 6/1993 |
| GB | 2286660 A | 8/1995 |
| GB | 2395907 B | 12/2004 |
| GB | 2504984 A | 2/2014 |
| GB | 2521240 A | 6/2015 |
| GB | 2552004 A | 1/2018 |
| GR | 3027678 T3 | 11/1998 |
| IT | 1217550 B | 3/1990 |
| IT | RE20120010 A1 | 8/2013 |
| IT | UB20159823 A1 | 7/2017 |
| JP | 2003305131 A | 10/2003 |
| JP | 2006130055 A | 5/2006 |
| JP | 4178762 B2 | 11/2008 |
| JP | 4324673 B2 | 9/2009 |
| JP | 2010207268 A | 9/2010 |
| JP | 2010533054 A | 10/2010 |
| JP | 2011194176 A | 10/2011 |
| JP | 2013063285 A | 4/2013 |
| JP | 2017518857 A | 7/2017 |
| JP | 2018501927 A | 1/2018 |
| JP | 2018018650 A | 2/2018 |
| KR | 20030065126 A | 8/2003 |
| KR | 100484618 B1 | 4/2005 |
| KR | 100491988 B1 | 5/2005 |
| KR | 200407524 Y1 | 1/2006 |
| KR | 100556230 B1 | 3/2006 |
| KR | 200410065 Y1 | 3/2006 |
| KR | 100841596 B1 | 6/2008 |
| KR | 20090063618 A | 6/2009 |
| KR | 20090095143 A | 9/2009 |
| KR | 100936914 B1 | 1/2010 |
| KR | 1020100026107 A | 3/2010 |
| KR | 101022244 B1 | 3/2011 |
| KR | 20110123831 A | 11/2011 |
| KR | 20120037011 A | 4/2012 |
| KR | 101233286 B1 | 2/2013 |
| KR | 101233287 B1 | 2/2013 |
| KR | 20130072244 A | 7/2013 |
| KR | 101292289 B1 | 8/2013 |
| KR | 20130128391 A | 11/2013 |
| KR | 101413022 B1 | 7/2014 |
| KR | 101415141 B1 | 7/2014 |
| KR | 101447532 B1 | 10/2014 |
| KR | 101511444 B1 | 4/2015 |

(56) References Cited

FOREIGN PATENT DOCUMENTS

| | | |
|---|---|---|
| KR | 20150058102 A | 5/2015 |
| KR | 101539633 B1 | 7/2015 |
| KR | 20150079619 A | 7/2015 |
| KR | 20150106379 A | 9/2015 |
| KR | 101650155 B1 | 8/2016 |
| KR | 101673182 B1 | 11/2016 |
| KR | 20170090654 A | 8/2017 |
| KR | 20170107603 A | 9/2017 |
| KR | 101794269 B1 | 11/2017 |
| KR | 20180059114 A | 6/2018 |
| KR | 20180092020 A | 8/2018 |
| KR | 101941863 B1 | 1/2019 |
| KR | 20190005981 A | 1/2019 |
| KR | 102000971 B1 | 7/2019 |
| KR | 20190001779 U | 7/2019 |
| KR | 200491572 Y1 | 5/2020 |
| KR | 20200000889 U | 5/2020 |
| KR | 20200052602 A | 5/2020 |
| KR | 20200056692 A | 5/2020 |
| KR | 20200056693 A | 5/2020 |
| KR | 20200056801 A | 5/2020 |
| KR | 20200056802 A | 5/2020 |
| KR | 20200057154 A | 5/2020 |
| KR | 2021000297 4 A | 1/2021 |
| KR | 20210002973 A | 1/2021 |
| MX | 2012012158 A | 4/2014 |
| NL | 7510644 A | 3/1977 |
| NL | 1037451 C2 | 5/2011 |
| RU | 2212909 C2 | 9/2003 |
| RU | 2226115 C2 | 3/2004 |
| RU | 2281128 C2 | 8/2006 |
| RU | 2373971 C2 | 11/2009 |
| RU | 2392979 C2 | 6/2010 |
| RU | 2395267 C2 | 7/2010 |
| RU | 2496532 C2 | 10/2013 |
| RU | 25294 71 C2 | 9/2014 |
| RU | 2596053 C2 | 8/2016 |
| RU | 2637104 C2 | 11/2017 |
| RU | 2645923 C2 | 2/2018 |
| SI | 24921 A | 8/2016 |
| TW | 200423986 A | 11/2004 |
| WO | WO-9312835 A1 | 7/1993 |
| WO | WO-9521655 A1 | 8/1995 |
| WO | WO-9527533 A1 | 10/1995 |
| WO | WO-9932191 A1 | 7/1999 |
| WO | WO-0013749 A1 | 3/2000 |
| WO | WO-0044346 A1 | 8/2000 |
| WO | WO-0107111 A2 | 2/2001 |
| WO | WO-0112089 A1 | 2/2001 |
| WO | WO-0193797 A2 | 12/2001 |
| WO | WO-0225675 A1 | 3/2002 |
| WO | WO-03078596 A2 | 9/2003 |
| WO | WO-03079916 A1 | 10/2003 |
| WO | WO-03090863 A1 | 11/2003 |
| WO | WO-03103769 A1 | 12/2003 |
| WO | WO-2004078255 A1 | 9/2004 |
| WO | WO-2004087255 A1 | 10/2004 |
| WO | WO-2004095385 A2 | 11/2004 |
| WO | WO-2004095835 A1 | 11/2004 |
| WO | WO-2004096343 A2 | 11/2004 |
| WO | WO-2004108211 A1 | 12/2004 |
| WO | WO-2005032660 A1 | 4/2005 |
| WO | WO-2005107866 A1 | 11/2005 |
| WO | WO-2006115120 A1 | 11/2006 |
| WO | WO-2007096206 A1 | 8/2007 |
| WO | WO-2007140584 A1 | 12/2007 |
| WO | WO-2008012827 A2 | 1/2008 |
| WO | WO-2008049775 A1 | 5/2008 |
| WO | WO-2008060494 A2 | 5/2008 |
| WO | WO-2008109058 A1 | 9/2008 |
| WO | WO-2008127011 A2 | 10/2008 |
| WO | WO-2008145260 A2 | 12/2008 |
| WO | WO-2009011708 A1 | 1/2009 |
| WO | WO-2009013729 A2 | 1/2009 |
| WO | WO-2009036040 A1 | 3/2009 |
| WO | WO-2009042863 A1 | 4/2009 |
| WO | WO-2009044400 A2 | 4/2009 |
| WO | WO-2009047628 A2 | 4/2009 |
| WO | WO-2009083915 A2 | 7/2009 |
| WO | WO-2010007614 A2 | 1/2010 |
| WO | WO-2010022278 A1 | 2/2010 |
| WO | WO-2010007614 A3 | 5/2010 |
| WO | WO-2010135425 A1 | 11/2010 |
| WO | WO-2010139376 A1 | 12/2010 |
| WO | WO-2011011749 A1 | 1/2011 |
| WO | WO-2011016019 A1 | 2/2011 |
| WO | WO-2011021184 A1 | 2/2011 |
| WO | WO-2011045002 A1 | 4/2011 |
| WO | WO-2011053607 A1 | 5/2011 |
| WO | WO-2011058556 A2 | 5/2011 |
| WO | WO-2011058565 A2 | 5/2011 |
| WO | WO-2011156495 A2 | 12/2011 |
| WO | WO-2012005766 A1 | 1/2012 |
| WO | WO-2012029065 A2 | 3/2012 |
| WO | WO-2012040243 A1 | 3/2012 |
| WO | WO-2012073232 A1 | 6/2012 |
| WO | WO-2012103632 A1 | 8/2012 |
| WO | WO-2012119293 A1 | 9/2012 |
| WO | WO-2012138169 A2 | 10/2012 |
| WO | WO-2013021380 A1 | 2/2013 |
| WO | WO-2013026393 A1 | 2/2013 |
| WO | WO-2013035088 A1 | 3/2013 |
| WO | WO-2013074576 A2 | 5/2013 |
| WO | WO-2013098815 A1 | 7/2013 |
| WO | WO-2013191699 A1 | 12/2013 |
| WO | WO-2014009875 A2 | 1/2014 |
| WO | WO-2014016820 A2 | 1/2014 |
| WO | WO-2014109653 A1 | 7/2014 |
| WO | WO-2014137344 A1 | 9/2014 |
| WO | WO-2014141229 A1 | 9/2014 |
| WO | WO-2014149021 A2 | 9/2014 |
| WO | WO-2014151431 A2 | 9/2014 |
| WO | WO-2014163020 A1 | 10/2014 |
| WO | WO-2014164926 A1 | 10/2014 |
| WO | WO-2015004540 A2 | 1/2015 |
| WO | WO-2015012639 A1 | 1/2015 |
| WO | WO-2015012672 A1 | 1/2015 |
| WO | WO-2015052705 A1 | 4/2015 |
| WO | WO-2015083305 A1 | 6/2015 |
| WO | WO-2015137733 A1 | 9/2015 |
| WO | WO-2015157725 A1 | 10/2015 |
| WO | WO-2015179571 A1 | 11/2015 |
| WO | WO-2016116747 A1 | 7/2016 |
| WO | WO-2016140871 A1 | 9/2016 |
| WO | WO-2017002065 A1 | 1/2017 |
| WO | WO 2017/106878 A1 | 6/2017 |
| WO | WO-2017103923 A1 | 6/2017 |
| WO | WO-2017159959 A1 | 9/2017 |
| WO | WO-2017160097 A2 | 9/2017 |
| WO | WO-2017176621 A1 | 10/2017 |
| WO | WO-2017196548 A1 | 11/2017 |
| WO | WO-2017212253 A1 | 12/2017 |
| WO | WO-2018006086 A1 | 1/2018 |
| WO | WO-2018008023 A1 | 1/2018 |
| WO | WO-2018044825 A1 | 3/2018 |
| WO | WO-2018121998 A2 | 7/2018 |
| WO | WO-2018122535 A1 | 7/2018 |
| WO | WO-2017160097 A3 | 9/2018 |
| WO | WO-2018208992 A1 | 11/2018 |
| WO | WO-2019120420 A1 | 6/2019 |
| WO | WO-2019150378 A1 | 8/2019 |
| WO | WO-2019166965 A1 | 9/2019 |
| WO | WO-2019173866 A1 | 9/2019 |
| WO | WO-2019183622 A1 | 9/2019 |
| WO | WO-2020002801 A1 | 1/2020 |
| WO | WO-2020035852 A1 | 2/2020 |
| WO | WO-2020041502 A1 | 2/2020 |
| WO | WO-2020142470 A1 | 7/2020 |
| WO | WO-2020144486 A1 | 7/2020 |
| WO | WO-2020174444 A1 | 9/2020 |
| WO | WO-2020183508 A1 | 9/2020 |
| WO | WO-2020190514 A1 | 9/2020 |
| WO | WO-2020208590 A1 | 10/2020 |

(56) References Cited

FOREIGN PATENT DOCUMENTS

| WO | WO-2020264263 A1 | 12/2020 |
|---|---|---|
| WO | WO-2021013654 A1 | 1/2021 |
| WO | WO-2021102365 A1 | 5/2021 |

OTHER PUBLICATIONS

2018 Cutera University, Clinical Forum, Cutera 20, 26 pages.
501(k) K030708 Slendertone FLEX Letter from Department of Health and Humane Serivces, Public Health Service, Jun. 25, 2003, 6 pages.
501(k) K163165 AM-100 Letter from Department of Health and Human Services, Public Health Service, Feb. 16, 2017, 9 pages.
Abulhasan, J.F., et al., "Peripheral Electrical and Magnetic Stimulation to Augment Resistance Training," Journal of Functional Morphology and Kinesiology, 1(3):328-342, (Sep. 2016).
Accent Radiofrequency System, Operator's Manual, Alma Lasers, Wellbeing Through Technology, 2008, 82 Pages.
Agilent Technologies, Inc., "Agilent 33500 Series 30 MHz Function/ Arbitrary Waveform Generator User's Guide," Publication No. 33520-90001 (Dec. 2010), 278 pages.
Agilent Technologies, Inc., "Agilent Announces 30 MHz Function/ Arbitrary Waveform Generators," Microwave J., URL: (Aug. 3, 2010), 8 pages.
*Allergan, Inc. et al. v. BTL Healthcare Technologies A.S.*, PTAB-PGR2021-00015, Paper 16 (Decision Denying Institution of Post-Grant Review), Jun. 17, 2021, 20 pages.
*Allergan, Inc. et al. v. BTL Healthcare Technologies A.S.*, PTAB-PGR2021-00016, Paper 16 (Decision Denying Institution of Post-Grant Review), Jun. 17, 2021, 20 pages.
*Allergan, Inc. et al. v. BTL Healthcare Technologies A.S.*, PTAB-PGR2021-00017, Paper 16 (Decision Denying Institution of Post-Grant Review), Jun. 16, 2021, 33 pages.
*Allergan, Inc. et al. v. BTL Healthcare Technologies A.S.*, PTAB-PGR2021-00018, Paper 16 (Decision Denying Institution of Post-Grant Review), Jun. 16, 2021, 42 pages.
*Allergan, Inc. et al. v. BTL Healthcare Technologies A.S.*, PTAB-PGR2021-00020, Paper 16 (Decision Denying Institution of Post-Grant Review), Jun. 16, 2021, 35 pages.
*Allergan, Inc. et al. v. BTL Healthcare Technologies A.S.*, PTAB-PGR2021-00021, Paper 17 (Decision Denying Institution of Post-Grant Review), Jun. 16, 2021, 33 pages.
*Allergan, Inc. et al. v. BTL Healthcare Technologies A.S.*, PTAB-PGR2021-00022; PTAB-PGR2021-00023; PTAB-PGR2021-00024; PTAB-PGR2021-00025; PTAB-IPR2021-00296; PTAB-IPR2021-00312, Paper 11 (Decision Settlement Prior to Institution of Trial), Jul. 6, 2021, 4 pages.
Alma Lasers., "Accent Radiofrequency System, Operator's Manual," Wellbeing Through Technology, 2008, Chapters 1-8, Appendix A.
Arjunan, P.A., et al., "Computation and Evaluation of Features of Surface Electromyogram to Identify the Force of Muscle Contraction and Muscle Fatigue," BioMed research international 2014:197960, Hindawi Pub. Co, United States (2014).
Avram, M.M and Harry, R.S.,"Cryolipolysis for Subcutaneous Fat Layer Reduction," Lasers in Surgery and Medicine, 41(10):703-708, Wiley-Liss, United States (Dec. 2009).
Bachasson, D., et al., "Quadriceps Function Assessment Using an Incremental Test and Magnetic Neurostimulation: a Reliability Study," Journal of Electromyography and Kinesiology, 23(3):649-658, Elsevier, England, (Jun. 2013).
Baranov, A., Krion, Whole Body Cryotherapy, Russia, 19 Pages.
Barker, A.T, "An Introduction to the Basic Principles of Magnetic Nerve Stimulation," Journal of Clinical Neurophysiology, 8(1):26-37, Lippincott Williams & Wilkins, United States, (Jan. 1991).
Barker, A.T., et al., "Non-Invasive Magnetic Stimulation of Human Motor Cortex," Lancet 1(8437):1106-1107, Elsevier, England (May 1985).
Barker, A.T., "The History and Basic Principles of Magnetic Nerve Stimulation," Electroencephalography and Clinical Neurophysiology 51:3-21, Elsevier, Netherlands (1999).

Barrett, J., et al., "Mechanisms of Action Underlying the Effect of Repetitive Transcranial Magnetic Stimulation on Mood: Behavioral and Brain Imaging Studies," Neuropsychopharmacology 29(6):1172-1189, Nature Publishing Group, England (Jan. 14, 2004).
Basic Protocol of Salus, Talent with Incontinence Chair, REMED, 1 page.
Behrens, M., et al., "Repetitive Peripheral Magnetic Stimulation (15 Hz RPMS) of the Human Soleus Muscle did not Affect Spinal Excitability," Journal of Sports Science and Medicine, 10(1):39-44, Dept. of Sports Medicine, Medical Faculty of Uludag University, Turkey (Mar. 2011).
Beilin, G., et al., "Electromagnetic Fields Applied to the Reduction of Abdominal Obesity," Journal of Cosmetic & Laser Therapy, 14(1):24-42, Informa Healthcare, England, (Feb. 2012).
Belanger, A-Y., "Chapter 13: Neuromuscular Electrical Stimulation," in Therapeutic Electrophysical Agents: Evidence Behind Practice, 3rd Edition, Lupash, E., ed., pp. 220-255, Lippincott Williams & Wilkins, United States (2015).
Benton, et al., "Functional Electrical Stimulation—A Practical Clinical Guide," Second Edition, The Professional Staff Association of the Rancho Los Amigos Hospital, Inc., 42 pages (1981).
Benton, L.A., et al., "Chapter 2: Physiological Basis of Nerve and Muscle Excitation" and "Chapter 4: General Uses of Electrical Stimulation," in Functional Electrical Stimulation: A Practical Guide, 2nd Edition, pp. 11-30 and 53-71, Rancho Los Amigos Rehabilitation Engineering Center, Downey, CA (1981), 42 pages.
Bergh, U., and Ekblom, B., "Influence of Muscle Temperature on Maximal Muscle Strength and Power Output in Human Skeletal Muscles," Acta Physiologica Scandinavica 107(1):33-37, Blackwell Scientific Publications, England (Aug. 1979).
Binder-MacLeod, S.A., et al., "Force Output of Cat Motor Units Stimulated with Trains of Linearly Varying Frequency," Journal of Neurophysiology 61(1):208-217, American Physiological Society, United States (Jan. 1989).
Binder-MacLeod, S.A., et al., "Use of a Catchlike Property of Human Skeletal Muscle to Reduce Fatigue," Muscle & Nerve 14(9):850-857, John Wiley & Sons, United States (Sep. 1991).
Bio Medical Research Limited., "Slendertone Flex Abdominal Training System, Instructions for Use," All pages (Aug. 2006).
Bio Medical Research Limited., "Slendertone Flex Max Instruction Manual," All pages (Apr. 2006).
Bio-Medical Research Ltd., K010335, 510(k) Summary, Slendertone Flex, All pages (Sep. 2001).
Bio-Medical Research Ltd., K022855 510(k) Summary, Slendertone, 1-6 (Mar. 2003).
Bischoff, C., et al., "Repetitive Magnetic Nerve Stimulation: Technical Considerations and Clinical Use in the Assessment of Neuromuscular Transmission," Electroencephalography and Clinical Neurophysiology 93(1):15-20, Elsevier, Ireland (Feb. 1994).
Bourland, J.D., et al., "Transchest Magnetic (Eddy-Current) Stimulation of the Dog Heart," Medical & Biological Engineering & Computing 28(2):196-198, Springer, United States (Mar. 1990).
BTL Industries, Inc., K163165 510(k) Summary, AM-100, All pages (Feb. 2017).
BTL Industries, Inc., K180813 510(k) Summary, Emsculpt, All pages (Mar. 2018).
*BTL Industries, Inc. v. Allergan Ltd. et al* DDE-1-20-cv-01046, Complaint for Patent Infringement and Exhibits 1-38, 821 pages (Aug. 2020).
*BTL Industries, Inc. v. Allergan Ltd. et al.*, DDE-1-20-cv-01046, Order Administratively Closing Case, Jul. 26, 2021, 1 page.
*BTL Industries, Inc. v. Allergan Ltd. et al* DDE-1-20-cv-01046, Order Granting Motion to Stay Pending Resolution of Proceedings at the International Trade Commission (Unopposed), 2 pages (Oct. 2020).
*BTL Industries, Inc. v. Allergan PLC et al* DDE-1-19-cv-02356, Complaint for Patent Infringement and Exhibits 1-34, 375 pages (Dec. 2019).
*BTL Industries, Inc. v. Allergan PLC et al* DDE-1-19-cv-02356, Order Granting Stipulation to Stay, Oct. 1, 2020, 1 page.
*BTL Industries, Inc. v. Allergan USA, Inc. et al.*, DDE-1-19-cv-02356, Order Administratively Closing Case, Jul. 26, 2021, 1 page.

(56) References Cited

OTHER PUBLICATIONS

Buenos Aires, Oct. 14, 2014, Venus Concept, Provision No. 7246, 56 pages (With Machine Translation).

Burge, S.M and Dawber, R.P.,"Hair Follicle Destruction and Regeneration in Guinea Pig Skin After Cutaneous Freeze Injury," Cryobiology, 27(2):153-163, Elsevier, Netherlands (Apr. 1990).

Busso, M. and Denkova, R., "Efficacy of High Intensity Focused Electro-Magnetic (HIFEM) Field Therapy When Used For Non-Invasive Buttocks Augmentation and Lifting: A Clinical Study" American Society for Laser Medicine and Surgery Abstracts, 382 (2018).

Bustamante, V., et al., "Muscle Training With Repetitive Magnetic Stimulation of the Quadriceps in Severe COPD Patients," Respiratory Medicine, 104(2):237-245, Elsevier, England, (Feb. 2010).

Bustamante, V., et al., "Redox Balance Following Magnetic Stimulation Training in the Quadriceps of Patients With Severe COPD," Free Radical Research, 42(11-12):939-948, Informa Healthcare, England, (Nov. 2008).

Callaghan, M.J., et al., "Electric Muscle Stimulation of the Quadriceps in the Treatment of Patellofemoral Pain," Archives of Physical Medicine and Rehabilitation 85(6):956-962, W.B. Saunders, United Staes (Jun. 2004).

Carbonaro, M., et al., "Architectural Changes in Superficial and Deep Compartments of the Tibialis Anterior during Electrical Stimulation over Different Sites," IEEE transactions on Neural Systems and Rehabilitation Engineering 28(11):2557-2565, IEEE, United States (Nov. 2020).

Caress, J.B., et al., "A Novel Method of Inducing Muscle Cramps Using Repetitive Magnetic Stimulation," Muscle Nerve, 23(1):126-128, John Wiley & Sons, United States, (Jan. 2000).

Certain Non-Invasive Aesthetic Body Contouring Devices, Components Thereof, and Methods of Using the Same, Inv. No. 337-TA-1219, BTL's Statement of Suggested Claim Terms to be Construed Pursuant to Ground Rule 6b, Nov. 4, 2020, 2 pages.

Certain Non-Invasive Aesthetic Body Contouring Devices, Components Thereof, and Methods of Using the Same, Inv. No. 337-TA-1219, Complainant BTL's Proposed Construction of Disputed Claim Terms, Dec. 8, 2020, 19 pages.

Certain Non-Invasive Aesthetic Body Contouring Devices, Components Thereof, and Methods of Using the Same, Inv. No. 337-TA-1219, Complaint, Aug. 5, 2020, 93 pages.

Certain Non-Invasive Aesthetic Body Contouring Devices, Components Thereof, and Methods of Using the Same, Inv. No. 337-TA-1219, Joint Claim Construction Chart, Dec. 14, 2020, 15 pages.

Certain Non-Invasive Aesthetic Body Contouring Devices, Components Thereof, and Methods of Using the Same; Inv. No. 337-TA-1219, Joint Claim Construction Chart, Dec. 18, 2020, 15 pages.

Certain Non-Invasive Aesthetic Body Contouring Devices, Components Thereof, and Methods of Using the Same, Inv. No. 337-TA-1219, Respondents' Allergan Limited, Allergan USA, Inc., Allergan, Inc., Zeltiq Aesthetics, Inc., Zeltiq Ireland Unlimited Company, and Zimmer MedizinSysteme GmbH's Notice of Prior Art, Nov. 20, 2020, 5 pages.

Certain Non-Invasive Aesthetic Body Contouring Devices, Components Thereof, and Methods of Using the Same, Inv. No. 337-TA-1219, Respondents' List of Claim Terms for Construction, Nov. 4, 2020, 8 pages.

Certain Non-Invasive Aesthetic Body Contouring Devices, Components Thereof, and Methods of Using the Same; Inv. No. 337-TA-1219, Respondents' List of Proposed Claim Constructions and Their Intrinsic and Extrinsic Support, filed Dec. 15, 2020, 23 pages.

Certain Non-Invasive Aesthetic Body Contouring Devices, Components Thereof, and Methods of Using the Same, Inv. No. 337-TA-1219, Response of Respondent Zimmer MedizinSysteme GmbH to the Complaint and Notice of Investigation, Oct. 22, 2020, 68 pages.

Certain Non-Invasive Aesthetic Body Contouring Devices, Components Thereof, and Methods of Using the Same, Inv. No. 337-TA-1219, Response of Respondents Allergan Limited, Allergan USA, Inc., Allergan, Inc., Zeltiq Aesthetics, Inc., and Zeltiq IrelandUnlimited Company to the Complaint and Notice of Investigation, Oct. 22, 2020, 69 pages.

Certain Non-Invasive Aesthetic Body-Contouring Devices, Components Thereof, and Methods of Using Same, Notice of Institution of Investigation, Inv. No. 337-TA-1219, Notice of Institution of Investigation, Sep. 2, 2020, 21 pages.

Certain Non-Invasive Aesthetic Body-Contouring Devices, Components Thereof, and Methods of Using the Same, Inv. No. 337-TA-1219, Order No. 21 (Initial Determination), Apr. 28, 2021,5 pages.

Certain Non-Invasive Aesthetic Body-Contouring Devices, Components Thereof, and Methods of Using the Same, Inv. No. 337-TA-1219, Order No. 30 (Order Concerning the Procedural Schedule), Aug. 4, 2021, 3 pages.

Certain Non-Invasive Aesthetic Body-Contouring Devices, Components Thereof, and Methods of Using the Same, Inv. No. 337-TA-1219, Order No. 17: Amending Procedural Schedule, Apr. 9, 2021, 4 pages.

Certified English Translation of Belyaev, A.G., "Effect of Magnetic Stimulation on the Strength Capacity of Skeletal Muscles," Ph.D. Thesis Abstract, Smolensk State Academy of Physical Culture, Sport, and Tourism, Dec. 11, 2020, 23 pages.

Certified English Translation of Belyaev, A.G., "Effect of Magnetic Stimulation on the Strength Capacity of Skeletal Muscles," Ph.D. Thesis, Smolensk State Academy of Physical Culture, Sport, and Tourism, Dec. 11, 2020, 117 pages.

Chattanooga Group of Encore Medical, L.P., "Intelect SWD 100 User Manual, Operation & Installation Instructions for Intelect SWD 00—Model 1600," All pages (2009).

Chesterton, L.S., et al.,"Skin Temperature Response to Cryotherapy," Archives of Physical Medicine and Rehabilitation, 83(4):543-549, W.B. Saunders, United States (Apr. 2002).

Clinical Application of Electro Magnetic Stimulation, Salus-Talent, Korea Society of interventional Muscle and Soft Tissue Stimulation Therapy, CR Technology, 141 pages.

Collins, D.F., et al., "Large Involuntary Forces Consistent With Plateau-Like Behavior of Human Motoneurons," Journal of Neuroscience 21(11):4059-4065, Society for Neuroscience, United States (Jun. 2001).

Colson, S., et al., "Re-Examination of Training Effects by Electrostimulation in the Human Elbow Musculoskeletal System," International Journal of Sports Medicine 21(4):281-288, Stuttgart, Thieme (May 2000).

Course in Physical Therapy, Presentation, Jan. 4, 2013, 156 pages.

CR Technologies, "Salus Talent Pop Manual KFDA First Approval Document" (English Translation), Nov. 25, 2011, 47 pages.

CR Technologies, "Notification of medical device manufacturing item permission, Salus Talent Pop KFDA Approval Document" (English Translation), 3 pages (Sep. 2011).

CR Technology Co, Ltd., "Salus-Talent Double Sales Brochure" 2 pages, (Oct. 2020).

CR Technology Co. Ltd., "Medical Laser Irradiator Salus-Talent-Pop User Manual Version 1.00" (Nov. 2020).

CR Technology Co. Ltd., Salus Talent Pop User Manual, Ver. 1.00, All pages, Approx. 2012.

CR Technology, Salus-Talent, Technical File of Electro-magnetic Stimulator, Document No. TF-C05, 2008, 241 pages.

CR Technology, Technology for Health and Business for Human Being, investor relations, 2008, 21 pages.

CryoGenTech GmbH, Company Profile, Creating CRYO, Medica, 9 pages.

Currier, D. P., "Effects of Electrical and Electromagnetic Stimulation after Anterior Cruciate Ligament Reconstruction," The Journal of Orthopaedic and Sports Physical Therapy 17(4):177-84, Williams and Wilkins, United States (1993).

Cutera, truSculptflex, Brochure, dated 2019, 2 pages.

Cynosure, SculpSure TM, The New Shape of Energy-Based body Contouring, 2015, Cynosure Inc, 2 pages.

Cynosure,Smooth Shapes XV, Now with Smoothshape petite, Transforming non-invasive Body Shaping,Retrieved from the Internet: (www.cynosure.com), 2011, Cynosure Inc, 8 pages.

Davies, C.T., et al., "Contractile Properties of the Human Triceps Surae With Some Observations on the Effects of Temperature and

(56) References Cited

OTHER PUBLICATIONS

Exercise," European Journal of Applied Physiology and Occupational Physiology 49(2):255-269, Springer Verlag, Germany (Aug. 1982).

Deng, Z.D., et al., "Electric Field Depth-Focality Tradeoff in Transcranial Magnetic Stimulation: Simulation: Comparison of 50 Coil Designs," Brain stimulation 6(1):1-13, Elsevier, New York (Jan. 2013).

Department of Health and Human Services, 501(k) Letter and Summary for K092476 Body Control System 4M Powered Muscle Stimulator, dated May 7, 2010, 5 pages.

Department of Health and Human Services, 501(k) Letter and Summary for K160992 HPM-6000 Powered Muscle Stimulator, dated Oct. 21, 2016, 9 pages.

Department of Health and Human Services, 501(k) Letter and Summary for K163415 SlimShape System Powered Muscle Stimulator, dated Apr. 20, 2017, 8 pages.

Depatment of Health and Human Services, 501(k) Letter and Summary for K182106 BTL 799-2T Powered Muscle Stimulator, dated Oct. 23, 2018, 9 pages.

Depatment of Health and Human Services, 501(k) Letter and Summary for K190456 BTL 799-2L Powered Muscle Stimulator, dated Jul. 5, 2019, 9 pages.

Depatment of Health and Human Services, 501(k) Letter and Summary for K192224 BTL 899 Powered Muscle Stimulator, dated Dec. 5, 2019, 11 pages.

Doucet, B., et al., "Neuromuscular Electrical Stimulation for Skeletal Muscle Function," Yale Journal of Biology & Medicine 85:201-215, Yale Journal of Biology and Medicine, United States (Jun. 2012).

Dudley, G. and Stevenson, S., "Use of Electrical Stimulation in Strength and Power Training," Special Problems in Strength and Power Training :426-435 (2003).

Duncan, D., et al., "Noninvasive Induction of Muscle Fiber Hypertrophy and Hyperplasia: Effects of High-Intensity Focused Electromagnetic Field Evaluated in an In-Vivo Porcine Model: A Pilot Study," Aesthetic Surgery Journal 40(5):568-574, Oxford University Press, United States (Apr. 2020).

DuoMAG Magnetic Stimulator, Alien Technik User Manuel, Jun. 26, 2012,48 pages, Version 2.1.

Dybek, T., et al.,"Impact of 10 Sessions of Whole Body Cryostimulation on Aerobic and Anaerobic Capacity and on Selected Blood Count Parameters," Biology of Sport, 29(1):39-43 (Jan. 2012).

Dynatronics., "Better Rehab Solutions for Better Outcomes," Rehabilitation Products Guide 2.3, 2017, 52 pages.

Effective PEMF Magnetic Fat Reduction Slimming Body Beauty Salon Machine (PEMF Star), Wolfbeauty 1980, PEMF Star, China, Retrieved from the Internet: (URL: https://www.ec21.com/product-details/Effective-PEMF-Magnetic-Fat-Reduction--89287 46.html), 2019, 5 pages.

Elamed, Magnetic Therapeutic Apparatus for Running Pulse Magfield small-sized ALMAG-01 Manual, allegedly accessed on Nov. 18, 2020, All pages.

Eliminate Stubborn Fat without Surgery or Downtime and Feel Great From Every Angle, Fear No Mirror®, Consultation Guide, Coolsculpting, 2014, 20 pages.

EndyMed PRO, 3 Deep, 3 Dimensional Control of the Target Zone, A Brilliant RadioFrequency Innovation, Eclipse Aesthetics, 7 Pages.

Energist Ltd—Acquired Chromogenez—Old Account, ilipo—Laser Liposuction (i-Lipo), Video Screenshots, Aug. 10, 2009, 5 pages.

Enoka, R.M., "Muscle Strength and Its Development," Sports Medicine 6:146-168, Springer (Oct. 1988).

Epstein, C., et al., "The Oxford Handbook of Transcranial Stimulation," 773 pages (2008).

European Commission, Neuodegenerative Disorders, 10 pages printed Dec. 27, 2016.

European Commission, "Neurogenerative Disorders," 10 pages printed Dec. 27, 2016.

European Patent Office, International Search Report and Written Opinion for International Application No. PCT/IB2016/053930, dated Dec. 12, 2016, 19 pages.

Exilis, Operator's Manual, BTL, 2012, 44 Pages.

Faghri, P.D., et al., "The Effects of Functional Electrical Stimulation on Shoulder Subluxation, Arm Function Recovery, and Shoulder Pain in Hemiplegic Stroke Patients," Archives of Physical Medicine and Rehabilitation 75(1):73-79, W.B. Saunders, United States (Jan. 1994).

FDA letter to Venus Legacy, Dec. 19, 2014, 7 pages.

Fischer, J., et al., "Precise Subpixel Position Measurement with Linear Interpolation of CMOS Sensor Image Data," The 6th IEEE International Conference on Intelligent Data Acquisition and Advanced Computing Systems, 500-504 (Sep. 2011).

Fisher, R., et al., "ILAE Official Report: a Practical Clinical Definition of Epilepsy," Epilepsia, 55(4):475-482, Blackwell Science, United States (Apr. 2014).

FMS Tesla Stym—AKCE, Medila Genova nabidika, Price offerc. 191, 24 pages.

Fujimura, K., et al., "Effects of Repetitive Peripheral Magnetic Stimulation on Shoulder Subluxations Caused by Stroke: A Preliminary Study," Neuromodulation: Journal of the International Neuromodulation Society 23(6):847-851, Wiley-Blackwell, United States (Nov. 2020).

Gaines, M., "Slendertone Abdominal Training System, the First FDA-Cleared Abdominal Belt, Introduced in United States by Compex Technologies on Time for Holiday Gift-Giving," Business Wire 44199 (Oct. 2003).

Geddes, L.A., "History of Magnetic Stimulation of the Nervous System," Journal of Clinical Neurophysiology 8(1):3-9, Lippincott Williams & Wilkins, United States (Jan. 1991).

Goetz, S.M., et al., "Coil Design for Neuromuscular Magnetic Stimulation Based on a Detailed 3-D Thigh Model," IEEE Transactions on Magnetics, 50(6):10, IEEE, (Jun. 2014).

Goodman, B.E., "Channels Active in the Excitability of Nerves and Skeletal Muscles Across the Neuromuscular Junction: Basic Function and Pathophysiology," Advances in Physiology Education 32(2):127-135, American Physiological Society, United States (Jun. 2008).

Gorgey, A., et al., "Effects of Electrical Stimulation Parameters on Fatigue in Skeletal Muscle," The Journal of Orthopaedic and Sports Physical Therapy 39(9):684-692, Williams and Wilkins, United States (Sep. 2009).

Gorodnichev, R.M., et al., "The Effect of Electromagnetic Stimulation on the Parameters of Muscular Strength," Human Physiology 40:65-69 (2014).

Gorodnichev, R.M., "Magnetic Stimulation of Muscles as New Method to Enhance Their Strength," Velikie Luki State Academy of Physical Culture and Sport, Velikie Luki, 2016, 5 pages.

Guangzhou HEMS Tech, PEMF Star, May 31, 2019, 5 pages.

Halaas, Y. and Bernardy, J., "Biochemical Perspective of Fat Physiology after Application of HIFEM Field Technology: Additional Investigation of Fat Disruption Effects in a Porcine Study," American Society for Laser Medicine and Surgery Abstracts, S4 (2019).

Hamnegard, C.H., et al., "Quadriceps Strength Assessed by Magnetic Stimulation of the Femoral Nerve in Normal Subjects," Clinical Physiology and Functional Imaging, 24(5):276-280, Blackwell, England, (Sep. 2004).

Han, B.H., et al., "Development of four-channel magnetic nerve stimulator," 2001 Proceedings of the 23rd Annual EMBS International Conference, pp. 1325-1327, Turkey (2001).

Han, T.R., et al., "Magnetic Stimulation of the Quadriceps Femoris Muscle: Comparison of Pain With Electrical Stimulation," American Journal of Physical Medicine & Rehabilitation, 85(7):593-599, Lippincott Williams & Wilkins, United States, (Jul. 2006).

Harkey, M.S., "Disinhibitory Interventions and Voluntary Quadriceps Activation: A Systematic Review," Journal of Athletic Training 49(3):411-421, National Athletic Trainers' Association, United States (2014).

Hasala, 0., et al., Case Study of Treating Acute Ankle Distortion Using TMS, Charles University, Faculty of Physical Education and Sports, Prague, Czech Republic, 4 Pages.

(56) References Cited

OTHER PUBLICATIONS

Heidland, A., et al., "Neuromuscular Electrostimulation Techniques: Historical Aspects and Current Possibilities in Treatment of Pain and Muscle Waisting," Clinical Nephrology 79 Suppl 1:S12-S23, Dustri-Verlag Dr. Karl Feistle, Germany (Jan. 2012).
Heisel, Jurgen, Physikalische Medizin, Stuttgart: Georg Thieme Verlag KG, 2005. ISBN 3-13-139881-7. p. 159.
Hera Estetik Medikal, "Lipostar" dated Jul. 7, 2014, accessed at https://www.youtube.com/watch?v=-R70nFIK9go, accessed on Dec. 15, 2021.
Hera Estetik Medikal, "Lipostar Manyetik Incelme", accessed at https://www.heraestetik.com/en/urundetay/liposter-manyetik-incelme, accessed on Dec. 15, 2021.
Hill, A., "The Influence of Temperature on the Tension Developed in an Isometric Twitch," Proceeding of the Royal Society B 138:349-354, (Sep. 1951).
Hirvonen, H.E., et al.,"Effectiveness of Different Cryotherapies on Pain and Disease Activity in Active Rheumatoid Arthritis. A Randomised Single Blinded Controlled Trial," Clinical and Experimental Rheumatology, 24(3):295-301, Clinical and Experimental Rheumatology SAS, Italy (May-Jun. 2006).
Hovey, C. and Jalinous, R., "The Guide to Magnetic Stimulation" Magstim, Pioneers in Nerve Stimulation and Monitoring, pp. 1-44 (2016).
Hovey, C., et al., "The Guide to Magnetic Stimulation," The Magstim Company Limited, 48 pages (Jul. 2006).
Huang, Y.Z., et al., "Theta Burst Stimulation of the Human Motor Cortex," Neuron 45(2):201-206, Cell Press, United States (Jan. 2005).
I-Lipo by Chroma genex, i-Lipo Ultra is the Intelligent, Non-Surgical Alternative to Liposuction, 2011, 2 pages.
Increasing Physiotherapy Presence in Cosmetology, Spa Inspirations, Jan. 2012, pp. 34-35.
Irazoqui P., Post Grant Review of U.S. Pat. No. 10,695,576, PTAB-PGR2021-00024, filed as EX1085, Dec. 14, 2020, 25 pages.
Iskra Medical, Magneto System, 2012, 2 pages.
Iskra Medical, "Tesla Stym—Functional Magnetic Stimulation FMS," Nov. 2013, http://ww.iskramedical.eu/magneto-therapy-medical/tesla-stym, 5 pages.
Iskra Medical, "Tesla Stym Website," URL: https://web.archive.org/web/20131106123126/http:/www.iskramedical.eu:80/magneto-therapy-medical/tesla-stym (Nov. 6, 2013).
Izumiya, Y., et al., "Fast/Glycolytic Muscle Fiber Growth Reduces Fat Mass and Improves Metabolic Parameters in Obese Mice", Cell Metabolism 7(2):159-172, Cell Press, United States (Feb. 2008).
Jacob, C., et al., "High Intensity Focused Electro-Magnetic Technology (HIFEM) for Non- Invasive Buttock Lifting and Toning of Gluteal Muscles: A Multi-Center Efficacy and Safety Study," Journal of Drugs in Dermatology 17(11):1229-1232, Physicians Continuing Education Corporation, United States (Nov. 2018).
Jacob, C.I., et al., "Safety and Efficacy of a Novel High-Intensity Focused Electromagnetic Technology Device for Noninvasive Abdominal Body Shaping," Journal of Cosmetic Dermatology, 17(5):783-787, Blackwell Science, United States (Oct. 2018).
Jacobm C., and Paskova, "A Novel Non-Invasive Technology Based on Simultaneous Induction of Changes in Adipose and Muscle Tissues: Safety and Efficacy of a High Intensity Focused Electro-Magnetic (HIFEM) Field Device Used for Abdominal Body Shaping," American Society for Laser Medicine and Surgery, 2018 Electronic Posters (ePosters) Town Hall and ePosters, 369, p. 1, Wiley Periodicals, Inc. (2018).
Jeanrenaud, B.,"Lipid components of adipose tissue," Handbook of Physiology, Adipose Tissue, Chapter 15, 8 Pages.
Johari Digital Healthcare Ltd., 510(k)—K062439 Powertone Letter from Department of Health and Humane Services Summary, Public Health Service, Jan. 8, 2007, 6 pages.
Johari Digital Healthcare Ltd., "510(k)—K131291 Torc Body Letter from Department of Health and Humane Services", Public Health Service, Jun. 14, 2013, 10 pages.
Johari Digital Healthcare Ltd., K131291 510(k) Summary, TorcBody, All pages (Jun. 2013).
Jutte, L.S., et al.,"The Relationship Between Intramuscular Temperature, Skin Temperature, and Adipose Thickness During Cryotherapy and Rewarming," Archives of Physical Medicine and Rehabilitation, 82(6):845-850, W.B. Saunders, United States (Jun. 2001).
Katuscakova, Z.L., et al., High Induction Magnet Therapy in Rehabilitation, Department of Physiactric Rehabilitation, 2012, 72 pages.
Katz, B., et al., "Changes in Subcutaneous Abdominal Fat Thickness Following High-Intensity Focused Electro-Magnetic (HIFEM) Field Treatments: A Multi Center Ultrasound Study," American Society for Laser Medicine and Surgery Abstracts, 360-361 (2018).
Katz, B., et al., "Ultrasound Assessment of Subcutaneous Abdominal Fat Thickness after Treatments with a High-Intensity Focused Electromagnetic Field Device: A Multicenter Study," Dermatologic Surgery 45(12):1542-1548, Williams & Wilkins, United States (Dec. 2019).
Kavanagh, S., et al., "Use of a Neuromuscular Electrical Stimulation Device for Facial Muscle Toning: A Randomized, Controlled Trial," Journal of Cosmetic Dermatology 11(4):261-266, Blackwell Science, United States (Dec. 2012).
Kent, D., and Jacob C., "Computed Tomography (CT) Based Evidence of Simultaneous Changes in Human Adipose and Muscle Tissues Following a High Intensity Focused Electro-Magnetic Field (HIFEM) Application: A New Method for Non-Invasive Body Sculpting," American Society for Laser Medicine and Surgery Abstracts, p. 370 (2018).
Kent, D,E. and Jacob, C.I., Simultaneous Changes in Abdominal Adipose and Muscle Tissues Following Treatments by High-Intensity Focused Electromagnetic HIFEM Technology- Based Device: Computed Tomography Evaluation, Journal of Drugs in Dermatology 18(11):1098-1102, Physicians Continuing Education Corporation, United States (Nov. 2019).
Kim, Y.H., et al.,"The Effect of Cold Air Application on Intra-Articular and Skin Temperatures in the Knee," Yonsei Medical Journal, 43(5):621-626, Yonsei University, Korea (South) (Oct. 2002).
Kinney, B.M. and Lozanova P., "High Intensity Focused Electromagnetic Therapy Evaluated by Magnetic Resonance Imaging: Safety and Efficacy Study of a Dual Tissue Effect Based Non-Invasive Abdominal Body Shaping," Lasers in Surgery and Medicine 51(1):40-46, Wiley-Liss, United States (Jan. 2019).
Kocbach et al., "A Simulation Approach to Optimizing Performance of Equipment for Thermostimulation of Muscle Tissue using COMSOL Multiphysics" Article in Biophysics & Bioeng. dated 2011, 26 pages.
Kolin, A., et al., "Stimulation of Irritable Tissues by means of an Alternating Magnetic Field," Proceedings of the Society for Experimental Biology and Medicine 102:251-253, Blackwell Science, United States (Oct. 1959).
Korman, P., et al., "Temperature Changes In Rheumatoid Hand Treated With Nitrogen Vapors and Cold Air," Rheumatology International, 32(10):2987-2992, Springer International, Germany (Oct. 2012).
Kotz, Y., "Theory and Practice of Physical Culture," Training of Skeletal Muscle With Method of Electrostimulation, 64-67 (Mar. 1971).
Kotz, Y., "Theory and Practice of Physical Culture," Training of Skeletal Muscle With Method ofElectrostimulation, 66-72 (Apr. 1971).
Krueger, N. et al., "Safety and Efficacy of a New Device Combining Radiofrequency and Low-Frequency Pulsed Electromagnetic Fields for the Treatment of Facial Rhytides," Journal of Drugs in Dermatology 11(11):1306-1309, Physicians Continuing Education Corporation, United States (Nov. 2012).
Kumar, N. and Agnihotri, R.C., "Effect of Frequency and Amplitude of Fes Pulses on Muscle Fatigue During Toning of Muscles," Journal of Scientific and Industrial Research 67(4):288-290, (Apr. 2008).
Lampropoulou, S.I., et al., "Magnetic Versus Electrical Stimulation in the Interpolation Twitch Technique of Elbow Flexors," Journal of

(56) References Cited

OTHER PUBLICATIONS

Sports Science and Medicine, 11(4):709-718, Dept. of Sports Medicine, Medical Faculty of Uludag University, Turkey (Dec. 2012).
Langford, J. and McCarthy, P.W., "Randomised controlled clinical trial of magnet use in chronic low back pain; a pilot study," Clinical Chiropractic 8(1):13-19, Elsevier (Mar. 2005).
Lee, P.B., et al., "Efficacy of Pulsed Electromagnetic Therapy for Chronic Lower Back Pain: a Randomized, Double-blind, Placebo-controlled Study," The Journal of International Medical Research 34(2):160-167, Cambridge Medical Publications, England (Mar.-Apr. 2006).
Leitch, M., et al., "Intramuscular Stimulation of Tibialis Anterior in Human Subjects: The Effects of Discharge Variability on Force Production and Fatigue," Physiological Reports 5(15):e13326, Wiley Periodicals, Inc., United States (Aug. 2017).
Leon-Salas, W.D., et al., "A Dual Mode Pulsed Electro-Magnetic Cell Stimulator Produces Acceleration of Myogenic Differentiation," Recent Patents on Biotechnology 7(1):71-81, Bentham Science Publishers, United Arab Emirates (Apr. 2013).
Letter from Department of Health and Human Services, Public Health Service, Dec. 19, 2014, 7 pages.
Lin, V.W., et al., "Functional Magnetic Stimulation: A New Modality for Enhancing Systemic Fibrinolysis," Archives of Physical Medicine and Rehabilitation 80(5):545-550, W.B. Saunders, United States (May 1999).
Lin, V.W., et al., "Functional Magnetic Stimulation for Conditioning of Expiratory Muscles in Patients with Spinal Cord Injury.," Archives of Physical medicine and Rehabilitation 82(2):162-166, W.B. Saunders, United States (Feb. 2001).
Lin, V.W., et al., "Functional Magnetic Stimulation for Restoring Cough in Patients With Tetraplegia," Archives of Physical Medicine and Rehabilitation, 79(5):517-522, W.B. Saunders, United States, (May 1998).
Lin, V.W., et al., "Functional Magnetic Stimulation of Expiratory Muscles: a Noninvasive and New Method for Restoring Cough," Journal of Applied Physiology (1985), 84(4):1144-1150, American Physiological Society, United States, (Apr. 1998).
Lin, V.W., et al., "Functional Magnetic Stimulation of the Respiratory Muscles in Dogs," Muscle & Nerve 21(8):1048-1057, John Wiley & Sons, United States (Aug. 1998).
Linehan, C., et al., Brainwave the Irish Epilepsy Assoication, "The Prevalence of Epilepsy in Ireland" Summary Report, pp. 1-8 (May 2009).
Lotz, B.P., et al., "Preferential Activation of Muscle Fibers with Peripheral Magnetic Stimulation of the Limb," Muscle & Nerve, 12(8):636-639, John Wiley & Sons, United States (Aug. 1989).
*Lumenis Be Ltd. v. BTL Healthcare Technologies A.S.*, PTAB-IPR2021-01402, Declaration of Dr. Marom Bikson (EX1002), Sep. 13, 2021, 244 pages.
*Lumenis Be Ltd. v. BTL Healthcare Technologies A.S.*, PTAB-IPR2021-01402, U.S. Pat. No. 10,821,295 Petition for Inter Partes Review, Sep. 13, 2021, 81 pages.
*Lumenis Be Ltd. v. BTL Healthcare Technologies A.S.*, PTAB-IPR2021-01403, Declaration of Dr. Marom Bikson (EX1002), Sep. 13, 2021, 243 pages.
*Lumenis Be Ltd. v. BTL Healthcare Technologies A.S.*, PTAB-IPR2021-01403, U.S. Pat. No. 10,821,295 Petition for Inter Partes Review, Sep. 13, 2021, 84 pages.
*Lumenis Be Ltd. v. BTL Healthcare Technologies A.S.*, PTAB-IPR2021-01404, Declaration of Dr. Marom Bikson (EX1002), Sep. 13, 2021, 245 pages.
*Lumenis Be Ltd. v. BTL Healthcare Technologies A.S.*, PTAB-IPR2021-01404, U.S. Pat. No. 10,124,187 Petition for Inter Partes Review, Sep. 13, 2021, 82 pages.
*Lumenis Be Ltd. v. BTL Healthcare Technologies A.S.*, PTAB-IPR2021-01405, Declaration of Dr. Marom Bikson (EX1002), Sep. 13, 2021, 247 pages.
*Lumenis Be Ltd. v. BTL Healthcare Technologies A.S.*, PTAB-IPR2021-01405, U.S. Pat. No. 10,124,187 Petition for Inter Partes Review, Sep. 13, 2021, 86 pages.
*Lumenis Be Ltd. v. BTL Healthcare Technologies A.S.*, PTAB-IPR2022-00126, Declaration of Dr. Marom Bikson (EX1002), Nov. 10, 2021, 263 pages.
*Lumenis Be Ltd. v. BTL Healthcare Technologies A.S.*, PTAB-IPR2022-00126, U.S. Pat. No. 10,695,576 Petition for Inter Partes Review, Nov. 10, 2021, 83 pages.
*Lumenis Be Ltd. v. BTL Healthcare Technologies A.S.*, PTAB-IPR2022-00127, Declaration of Dr. Marom Bikson (EX1002), Nov. 10, 2021, 269 pages.
*Lumenis Be Ltd. v. BTL Healthcare Technologies A.S.*, PTAB-IPR2022-00127, U.S. Pat. No. 10,695,576 Petition for Inter Partes Review, Nov. 10, 2021, 84 pages.
*Lumenis Ltd. v. BTL Healthcare Technologies A.S.*, PTAB-IPR2021-01273, Declaration of Dr. Marom Bikson (EX1002), Aug. 13, 2021, 225 pages.
*Lumenis Ltd. v. BTL Healthcare Technologies A.S.*, PTAB-IPR2021-01273, U.S. Pat. No. 10,478,634, Petition for Inter Partes Review, Aug. 13, 2021, 70 pages.
*Lumenis Ltd. v. BTL Healthcare Technologies A.S.*, PTAB-IPR2021-01275, Declaration of Dr. Marom Bikson (EX1002), Aug. 5, 2021, 282 pages.
*Lumenis Ltd. v. BTL Healthcare Technologies A.S.*, PTAB-IPR2021-01275, U.S. Pat. No. 10,632,321, Petition for Inter Partes Review, Aug. 5, 2021, 92 pages.
*Lumenis Ltd. v. BTL Healthcare Technologies A.S.*, PTAB-IPR2021-01276, Declaration of Dr. Marom Bikson (EX1002), Aug. 5, 2021, 241 pages.
*Lumenis Ltd. v. BTL Healthcare Technologies A.S.*, PTAB-IPR2021-01276, U.S. Pat. No. 10,965,575, Petition for Inter Partes Review, Aug. 5, 2021, 79 pages.
*Lumenis Ltd. v. BTL Healthcare Technologies A.S.*, PTAB-IPR2021-01278, Declaration of Dr. Marom Bikson (EX1002), Aug. 13, 2021, 255 pages.
*Lumenis Ltd. v. BTL Healthcare Technologies A.S.*, PTAB-IPR2021-01278, U.S. Pat. No. 10,709,894, Petition for Inter Partes Review, Aug. 13, 2021, 85 pages.
*Lumenis Ltd. v. BTL Healthcare Technologies A.S.*, PTAB-IPR2021-01279, Declaration of Dr. Marom Bikson (EX1002), Aug. 5, 2021, 258 pages.
*Lumenis Ltd. v. BTL Healthcare Technologies A.S.*, PTAB-IPR2021-01279, U.S. Pat. No. 10,709,895, Petition for Inter Partes Review, Aug. 5, 2021, 88 pages.
*Lumenis Ltd. v. BTL Healthcare Technologies A.S.*, PTAB-IPR2021-01280, Declaration of Dr. Marom Bikson (EX1002), Aug. 13, 2021, 235 pages.
*Lumenis Ltd. v. BTL Healthcare Technologies A.S.*, PTAB-IPR2021-01280, U.S. Pat. No. 10,478,634, Petition for Inter Partes Review, Aug. 13, 2021, 69 pages.
*Lumenis Ltd. v. BTL Healthcare Technologies A.S.*, PTAB-IPR2021-01282, Declaration of Dr. Marom Bikson (EX1002), Aug. 5, 2021, 267 pages.
*Lumenis Ltd. v. BTL Healthcare Technologies A.S.*, PTAB-IPR2021-01282, U.S. Pat. No. 10,632,321, Petition for Inter Partes Review, Aug. 5, 2021, 89 pages.
*Lumenis Ltd. v. BTL Healthcare Technologies A.S.*, PTAB-IPR2021-01283, Declaration of Dr. Marom Bikson (EX1002), Aug. 5, 2021, 241 pages.
*Lumenis Ltd. v. BTL Healthcare Technologies A.S.*, PTAB-IPR2021-01283, U.S. Pat. No. 10,695,575, Petition for Inter Partes Review, Aug. 5, 2021, 84 pages.
*Lumenis Ltd. v. BTL Healthcare Technologies A.S.*, PTAB-IPR2021-01284, Declaration of Dr. Marom Bikson (EX1002), Aug. 5, 2021, 279 pages.
*Lumenis Ltd. v. BTL Healthcare Technologies A.S.*, PTAB-IPR2021-01284, U.S. Pat. No. 10,709,895, Petition for Inter Partes Review, Aug. 5, 2021, 93 pages.
*Lumenis Ltd. v. BTL Healthcare Technologies A.S.*, PTAB-IPR2021-01285, Declaration of Dr. Marom Bikson (EX1002), Aug. 13, 2021, 249 pages.
*Lumenis Ltd. v. BTL Healthcare Technologies A.S.*, PTAB-IPR2021-01285, U.S. Pat. No. 10,709,894, Petition for Inter Partes Review, Aug. 13, 2021, 79 pages.

(56) References Cited

OTHER PUBLICATIONS

Madariaga, V.B., et al., "[Magnetic Stimulation of the Quadriceps: Analysis of 2 Stimulators Used for Diagnostic and Therapeutic Applications]," Archives De Bronconeumologfa, 43(7):411-417, Elsevier Espana, Spain, (Jul. 2007).

Maffiuletti, N.A., et al., "Activation of Human Plantar Flexor Muscles Increases After Electromyostimulation Training," Journal of Applied Physiology 92(4):1383-1392, American Physiological Society, United States (Nov. 2001).

Maffiuletti, N.A., et al., "The Effects of Electromyostimulation Training and Basketball Practice on Muscle Strength and Jumping Ability," International journal of sports medicine 21(6):437-443, Thieme, Germany (Aug. 2000).

Mag and More Gmbh, Magnetic and Life Science System, Power Mag, 12 Pages.

Mag Expert, 2 pages.

Mag Venture, Magnetic Stimulation, Accessories Catalogue, Accessories Catalogue, 2011, 54 pages.

Magstim Company Limited, K051864 510(k) Summary, Magstim Rapid and Magstim Super Rapid, All pages (Dec. 2005).

Magstim Company US, LLC, K060847 510(k) Summary, Magstim Model 200-2 with Double 70mm Remote Coil, All pages (Sep. 2006).

Magstim Corporation US, K992911 510(k) Summary, Magstim Rapid, All pages (Jan. 2000).

MagVenture, MagPro® by MagVenture®, Versatility in Magnetic Stimulation, World Leading Transcranial Magnetic Stimulation Systems, 2011, 6 Pages.

Man, W.D-C., et al., "Magnetic Stimulation for the Measurement of Respiratory and Skeletal Muscle Function," The European Respiratory Journal 24(5):846-60, European Respiratory Society, England (2004).

Manstein, D., et al., "Selective Cryolysis: A Novel Method of Non-Invasive Fat Removal," Lasers in Surgery and Medicine, 40(9):595-604, Wiley-Liss, United States (Nov. 2008).

Mantovani, A., et al., "Applications of Transcranial Magnetic Stimulation to Therapy in Pyschiatry," Psychiatric Times 21(9), Intellisphere, 29 pages (Aug. 2004).

Marek Heinfarth, "Lipostar" dated Jan. 9, 2013, accessed at https://www.youtube.com/watch?v=hZurkn8iU_U, accessed on Dec. 15, 2021.

Markov, M.S., "Pulsed Electromagnetic Field Therapy History, State of the Art and Future," Environment Systems and Decisions 27(4):465-475, Springer (Dec. 2007).

MecoTec Freezing Technology, Presentation Cryoair Whole Body Cryotherapy Chambers, Germany, Jul. 2017, 52 Pages.

Medline, Body Temperature Norms, 2 pages (Year: 2019).

Meka\Ivy et al., "Influence of Electro-lipolysis on Lipid Profile and Central Obesity in Obese Premenopausal Women" Bull. Fae. Ph. Th. Cairo Univ., vol. 17, No. (1), dated Jan. 2012, pp. 59-68.

Mettler J.A., et al., "Low-Frequency Electrical Stimulation With Variable Intensity Preserves Torque," Journal of Electromyography and Kinesiology : Official Journal of the International Society of Electrophysiological Kinesiology 42:49-56, Oxford:Elsevier, England (Oct. 2018).

Mogyoros, I., et al., "Strength-Duration Properties of Human Peripheral Nerve," Brain 119(Pt 2):439-447, Oxford University Press, England (Apr. 1996).

Moon, Chi-Woong"Study on the Pulsed Electromagnetic Fields Effect of Adipocyte Decomposition" Final Report of a Middle-grade Researcher Support Project, Inje University, 2017.

Morrissey. M., "Electromyostimulation from a Clinical Perspective," Sports Medicine 6(1):29-41, Springer International, New Zealand (Aug. 1988).

Mulholland, R.S., "Synergistic Multi-polar Radiofrequency and Pulsed Magnetic Fields in the Non-Invasive Treatment of Skin Laxity and Body Contouring," 4 pages.

Mustafa, B., "Design and Construction of a Low Cost dsPIC Controller Based Repetitive Transcranial Magnetic Stimulator TMS," Journal of medical systems 34(1):15-24, Kluwer Academic/Plenum Publishers, United States (2010).

Nadler, S.F., et al., "The Physiologic Basis and Clinical Applications of Cryotherapy and Thermotherapy for the Pain Practitioner," Pain Physician, 7(3):395-399, American Society of Interventional Pain Physicians, United States (Jul. 2004).

Nassab, R., "The Evidence Behind Noninvasive Body Contouring Devices," Aesthetic Surgery Journal, 35(3):279-293, Oxford University Press, England (Mar. 2015).

National Institute of Neurological Disorders and Stroke, Epilepsy Information Page, www.ninds.nih.gov/disorders/epilepsy/epilepsy.htm, pp. 1-6 (Feb. 1, 2016).

Neotonus, Inc., K973096 510(k) Summary, Neotonus Model 1000 Muscle Stimulator System, All pages (Jun. 1998).

Neotonus, Inc., K973929 510(k) Summary and FDA Correspondence, Neotonus, All pages (May 1998).

Neuro Star, TMS Therapy, Bringing Hope to Patients with Depression, 2013, 6 Pages.

Neurosofl, Ivanovo, Since 1992, Magnetic Stimulator, NEURO-MS, Technical Manual, Neurosofl Ltd, Ivanovo, Russia, 2006, 67 Pages.

Nexstim NBS System, Navigated Brain Stimulation, Noninvasive, direct cortical mapping, 2012, 5 Pages.

Neyroud, D., et al., "Comparison of Electrical Nerve Stimulation, Electrical Muscle Stimulation and Magnetic Nerve Stimulation to Assess the Neuromuscular Function of the Plantar Flexor Muscles," European journal of applied physiology 115(7):1429-1439, Springer-Verlag, Germany (2015).

Nielsen, J.F., et al., "A New High-frequency Magnetic Stimulator With an Oil-cooled Coil," Journal of Clinical Neurophysiology 12(5):460-467, Lippincott Williams & Wilkins, United States (Sep. 1995).

Non Final Office Action dated Jun. 23, 2017, in United States U.S. Appl. No. 15/473,390, Schwarz, T., eta/., filed Mar. 29, 2017.

Notice of Allowance dated Jul. 21, 2021 for U.S. Appl. No. 17/087,850 (pp. 1-8).

Notice of Allowance dated May 6, 2020 for U.S. Appl. No. 16/194,800 (pp. 1-8).

Notice of Allowance dated Oct. 8, 2019 for U.S. Appl. No. 15/603,162 (pp. 1-8).

Notice of Allowance dated Mar. 24, 2021 for U.S. Appl. No. 17/087,850 (pp. 1-8).

Novickij, V., et al., "Compact Microsecond Pulsed Magnetic Field Generator for Application in Bioelectronics," Elektronika ir Elektrotechnika 19(8):25-28 (Oct. 2013).

Novickij, V., et al., "Design and Optimization of Pulsed Magnetic Field Generator for Cell Magneto-Permeabilization," Elektronika ir Elektrotechnika(Electronics and Electrical Engineering) 23(2):21-25 (Apr. 2017).

Novickij, V., et al., "Magneto-Permeabilization of Viable Cell Membrane Using High Pulsed Magnetic Field," IEEE Transactions on Magnetics 51(9), All pages (Sep. 2015).

Novickij, V., et al., "Programmable Pulsed Magnetic Field System for Biological Applications," IEEE Transactions on Magnetics 50(11):5 (Nov. 2014).

NPF Electroapparat, Amplipulse-5Br Manual, allegedly accessed on Nov. 18, 2020, All pages.

Neurosoft Ltd., "Neurosofl—Neuro-MS Transcranial Magnetic Simulator Technical Manual," All pages (Nov. 2014).

Obsluze, "Apparatus for High Induction Magnetic Stimulation," 2016, 42 pages.

Obsluze, N.K.,Usage Instructions, User's Manual, Device for high-induction magnetic stimulation of type designation:Saluter Moti, 2016,88 Pages.

Office Action dated Aug. 15, 2019 for U.S. Appl. No. 16/194,800 (pp. 1-12).

Office Action dated Jul. 10, 2020 for U.S. Appl. No. 15/678,915 (pp. 1-9).

Office Action dated Jun. 14, 2021 for U.S. Appl. No. 15/786,303 (pp. 1-13).

(56) References Cited

OTHER PUBLICATIONS

Office Action dated Jun. 28, 2021 for U.S. Appl. No. 16/727,458 (pp. 1-11).
Office Action dated October?, 2019 for U.S. Appl. No. 15/678,915 (pp. 1-8).
Oliveira, P.De., et al., "Neuromuscular Fatigue After Low-and Medium-frequency Electrical Stimulation in Healthy Adults," Muscle & Nerve 58(2):293-299, John Wiley & Sons, United States (Aug. 2018).
Operating Manual: Magstim D702 Coil, MOP06-EN, Revision 01, The Magstim Company Limited, Feb. 2012, 14 Pages.
Operating Manual: Magstim Magstim 2002 , MOP01-EN, Revision 01, The Magstim Company Limited, Sep. 2011, 25 Pages.
Operating Manual: Magstim, Magstim Alpha Coil Range, MOP11-EN, Revision 01, Oct. 2012, 18 Pages.
Operating Manual: Magstim, Magstim Bistim2 , MOP02-EN, Revision, The Magstim Company Limited, 01, Sep. 2011, 27 Pages.
Operating Manual, Magstim, Model 200, P/N 3001-01, Double 70mm, Remote Coil, P/N 3190-00, The Magstim Company Limited, 2006, 32 pages.
Operating Manual: Magstim R, 2nd, Generation Coil Family, 3100-23-02, Magstim Coils, The Magstim Company Limited, Nov. 2002, 14 Pages.
Operating Manual, Magstim R Air-Cooled Double 70mm Coil System, 1600-23-04, The Magstim Company Limited, 1999, 18 Pages.
Operating Manual: Magstim R, Bistim System, P/N 3234-23-01, The Magstim Company Limited, Nov. 2004, 30 Pages.
Operating Manual: Magstim R, Coils & Accessories, 1623-23-07, Magstim Coils & Accessories, May 2010, 24 Pages.
Operating Manual: Magstim, Rapid2, P/N 3576-23-09, The Magstim Company LTD, Nov. 2009, 61 Pages.
Operator's Manual: BTL Emsculpt, BTL Industries Ltd, United Kingdom, 2018, 35 pages.
Operator's Manual: BTL, HPM-6000U, BTL Industries Ltd, United Kingdom, Dec. 2016, 36 pages.
Otte, J.S., et al.,"Subcutaneous Adipose Tissue Thickness Alters Cooling Time During Cryotherapy," Archives of Physical Medicine and Rehabilitation, 83(11):1501-1505, W.B. Saunders, United States (Nov. 2002).
Pain Management Technologies, "Pain Management Technologies Product Catalog," (2012).
Papimi, for Scientific Research, Pap Ion Magnetic Inductor, Presentation, Magnetotherapeutic Device, Nov. 2009, 61 Pages.
Periso SA, CTU mega Diamagnetic Pump 20: Device for Diamagnetic Therapy, CTU Mega 20 Manual, dated Aug. 28, 2019, 44 pages, Pazzallo Switzerland.
Photograph, Alleged Photograph of Components of a Salus Talent Pop Double Device with an Alleged Manufacture date of Nov. 14, 2012, 1 page.
Physiomed, Mag-Expert, Physiomed Manual, Dec. 19, 2012.
Physiomed, Physiomed Mag-Expert, Physiomed Catalog, pp. 81-83.
Platil, A., "Magnetopneumography Using Optical Position Reference," Sensor Letters 11(1):69-73, ResearchGate (2013).
Podebradsky.K., et al., Clinical study of high-inductive electromagnetic stimulator Salus talent, 2010, 8 pages.
Pohanka, J., et al., "An Embedded Stereovision System: Aspects of Measurement Precision," 12th Biennial Baltic Electronics Conference, pp. 157-160 (Oct. 2010).
Polk, C., "Therapeutic Applications of Low-Frequency Sinusoidal and Pulsed Electric and Magnetic Fields," The Biomedical Engineering Handbook, vol. 1, 2000, Second edition, CRC Press LLC, pp. 1625-1636.
Polkey M.I., et al., "Functional Magnetic Stimulation of the Abdominal Muscles in Humans," American Journal of Respiratory and Critical Care Medicine 160(2):513-522, American Thoracic Society, United States (Aug. 1999).
Polkey, M.I., et al., "Quadriceps Strength and Fatigue Assessed by Magnetic Stimulation of the Femoral Nerve in Man," Muscle Nerve 19(5):549-555, John Wiley & Sons, United States, (May 1996).

Pollogen, Trilipo MED Procedure, Brochure, dated Apr. 7, 2021, 76 pages.
Pollogen, Maximus Non-invasive body shaping System, User Manual, dated May 1, 2012, 44 pages, http://download.lifvation.com/Maximus_UserManual.pdf.
Porcari, J.P., et al., "Effects of Electrical Muscle Stimulation on Body Composition, Muscle Strength, and Physical Appearance," Journal of Strength and Conditioning Reasearch 16(2):165-172, Human Kinetics Pub., United States (May 2002).
Porcari, J.P., et al., "The Effects of Neuromuscular Electrical Stimulation Training on Abdominal Strength, Endurance, and Selected Anthropometric Measures," Journal of Sports Science and Medicine 4(1):66-75, Dept. of Sports Medicine, Turkey (Mar. 2005).
Pribula, 0. and Fischer, J., "Real Time Precise Position Measurement Based on Low- Cost CMOS Image Sensor," IEEE, 5 pages (2011).
Pribula, 0., et al., "cost-effective Image Acquisition System for Precise Pc-based Measurements," Przeglad Elektrotechniczny (Electrical Review), 259-263, 2011.
Pribula, 0., et al., "Optical Position Sensor Based on Digital Image Processing: Magnetic Field Mapping Improvement," Radioengineering 20 (1):55-60, (Apr. 2011).
Pribula, 0., et al., "Real-Time Video Sequences Matching Spatio-Temporal Fingerprint," IEEE, 911-916 (Jun. 2010).
Prouza, 0., et al., "High-Intensity Electromagnetic Stimulation Can Reduce Spasticity in Post-Stroke Patients," International Journal of Physiotherapy 5(3):87-91 (2018).
Prouza, 0., "Ex-Post Analyza Spot Rebnich Dani," All pages, (2008).
Prouza, 0., "Targeted Radiofrequency Therapy for Training Induced Muscle Fatigue—Effective or Not?," International Journal of Physiotherapy 3(6):707-710 (Dec. 2016).
PTAB-IPR2021-00296, U.S. Pat. No. 10,493,293, Petition for Inter Partes Review, Dec. 14, 2020, 117 pages.
PTAB-IPR2021-00312, U.S. Pat. No. 10,478,634, Petition for Inter Partes Review, Dec. 14, 2020, 108 pages.
PTAB-PGR2021-00015, U.S. Pat. No. 10,709,895, Petition for Post-Grant Review, Dec. 14, 2020, 140 pages.
PTAB-PGR2021-00016, U.S. Pat. No. 10,709,895, Petition for Post-Grant Review, Dec. 14, 2020, 144 pages.
PTAB-PGR2021-00017, U.S. Pat. No. 10,632,321, Petition for Post-Grant Review, Dec. 14, 2020, 121 pages.
PTAB-PGR2021-00018, U.S. Pat. No. 10,632,321, Petition for Post-Grant Review, Dec. 14, 2020, 140 pages.
PTAB-PGR2021-00020, U.S. Pat. No. 10,695,575, Petition for Post-Grant Review, Dec. 14, 2020, 112 pages.
PTAB-PGR2021-00021, U.S. Pat. No. 10,695,575, Petition for Post-Grant Review, Dec. 14, 2020, 117 pages.
PTAB-PGR2021-00022, U.S. Pat. No. 10,709,894, Petition for Post-Grant Review, Dec. 14, 2020, 119 pages.
PTAB-PGR2021-00023, U.S. Pat. No. 10,709,894, Petition for Post-Grant Review, Dec. 14, 2020, 136 pages.
PTAB-PGR2021-00024, U.S. Pat. No. 10,695,576, Petition for Post-Grant Review, Dec. 14, 2020, 136 pages.
PTAB-PGR2021-00025, U.S. Pat. No. 10,695,576, Petition for Post-Grant Review, Dec. 14, 2020, 135 pages.
Publication of Medical Device Manufacturing Approval of Salus-Talent-Pro, approval date Mar. 11, 2014, 39 pages.
Quick Start Manuals, Magstim Super Rapid Plus Quick Start, Aalto TMS Laboratory, Aalto School of Science, 2013, 7 Pages.
Radakovic T. and Radakovic N., "The Effectiveness of the Functional Magnetic Stimulation Therapy in Treating Sciatica Syndrome," Open Journal of Therapy and Rehabilitation 3(3):63-69 (2015).
Reaction User Manual, Viora, 2008, 53 Pages.
Reshaping the Future of Your Practice, Cool sculpting, A Revolution in Aesthetic Fat Reduction, 2011, 10 Pages.
Riehl., M., "Chapter 3: TMS Stimulator Design" The Oxford Handbook of Transcranial Stimulation, Wasserman, E.M., ed., pp. 13-23, Oxford University Press, 26 pages, United Kingdom (2008).
Roots, H., and Ranatunga, K.W., "An Analysis of the Temperature Dependence of Force, During Steady Shortening at Different Veloci-

(56) References Cited

OTHER PUBLICATIONS ties, in (Mammalian) Fast Muscle Fibres," Journal of Muscle Research and Cell Motility 29(1):9-24, Springer, Netherlands (Jun. 2008).

Ruiz-Esparza, J. and J. Barba Gomez., "The Medical Face Lift: A Noninvasive, Nonsurgical Approach to Tissue Tightening in Facial Skin Using Nonablative Radiofrequency," Dermatologic Surgery 29(4):325-332, Williams & Wilkins, United States (Apr. 2003).

Russian excerpt of Werner, R., Magnetotherapy, Pulsating energy resonance therapy, 41-67 (Jun. 2007).

Rutkove, S., "Effects of Temperature on Neuromuscular Electro physiology," Muscle & Nerve 24(7):867-882, John Wiley & Sons, United States (Jul. 2001).

Salus Talent, a Vertice and Talos, Drott, 6 pages.

Salus Talent, Deep Penetrating Electro-Magnetic Stimulator, CR Technology, 4 pages.

Salus Talent, Deep Penetrating Electro-Magnetic Stimulator, Rehabilitation Medical Company, New choice, new satisfaction, Talent, 4 pages.

Salus Talent, Electro Magnetic Stimulator, CR Technology, 9 Pages.

Salus Talent Pop, The first sales bill, Authorization No. 20120221-41000096-66667961, 2 pages, (Feb. 2012).

Salus Talent Pro, Specification, 2 pages.

Salus, Talent Pro, The Birth of Salus Talent Pro inspired by 10 Years of Experience, Specification, Rehabilitation Medical Company, Sliman, 2 pages.

Salus, Talent Pro, The World's 1st Development 3 Tesla, 2Channel Magnetic field Therapy, Sliman, 1O pages.

Salus Talent—A, Remed, User Guide, High Intensity Electro Magnetic Field Therapy, 2017, 37 pages.

Salus Talent-Pop Double, 1 page.

Salus-Talent, Device for Deep Electromagnetic Stimulation, Nowosc, Fizjoterapia, 6 Pages.

Sargeant, A.J., "Effect of Muscle Temperature on Leg Extension Force and Short-term Power Output in Humans," European Journal of Applied Physiology and Occupational Physiology 56(6):693-698, Springer Verlag, Germany (Sep. 1987).

Schaefer, D.J., et al., "Review of Patient Safety in Time-Varying Gradient Fields," Journal of Magnetic Resonance Imaging 12:20-29, Wiley-Liss, United States (Jul. 2000).

Scientific & Clinical Background of (MP)2®—A synergy between Multi polar RF and Pulsed Magnetic Field developed by Venus Concept. Prof. Yeouda Edoute M.D, Ph,D, 2 pages.

Shimada, Y., et al., "Effects of therapeutic magnetic stimulation on acute muscle atrophy in rats after hindlimb suspension," Biomedical Research 27(1):23-27, Biomedical Research Foundation, Japan (Feb. 2006).

Silinskas, V., et al., "Effect of Electrical Myostimulation on the Function of Lower Leg Muscles," Journal of strength and Conditioning Research 31(6):1577-1584, Human Kinetics Pub, United States (2017).

Sport-Elec S.A., K061914 510(k) Summary, Sport- Elec, All pages (Jul. 2007).

Sport-Elec S.A., K081026 510(k) Summary, Sport- Elec, All pages (Nov. 2008).

Starbelle, PEMF Shape, Webpage, dated Feb. 10, 2020, 3 pages, available at http://www.starbelle.cn/info/PEMFShape.html.

Stedman, T.L., "Aponeurosis—Apparatus," in Stedman's Medical Dictionary, 27th Edition, Pugh, M.B., ed., pp. 113-114, Lippincott Williams & Wilkins, Baltimore, MD (2000).

Stevens, J.E., et al., "Neuromuscular Electrical Stimulation for Quadriceps Muscle Strengthening After Bilateral Total Knee Arthroplasty: A Case Series," Journal of Orthopaedic and Sports Physical Therapy 34(1):21-29, Williams and Wilkins, United States (Jan. 2004).

Struppler, A., et al., "Facilitation of Skilled Finger Movements by Repetitive Peripheral Magnetic Stimulation (RPMS)—A New Approach In Central Paresis.," NeuroRehabilitation 18(1):69-82, IOS Press, Amsterdam (2003).

Struppler, A., et al., "Modulatory Effect of Repetitive Peripheral Magnetic Stimulation on Skeletal Muscle Tone in Healthy Subjects: Stabilization of the Elbow Joint," Experimental Brain Research 157(1):59-66, Springer Verlag, Germany (Feb. 2004).

Suarez-Bagnasco, D., et al., "The Excitation Functional for Magnetic Stimulation of Fibers.," Annual International Conference of the IEEE Engineering in Medicine and Biology Society, IEEE Engineering in Medicine and Biology Society, Annual International Conference, 2010:4829-4833, IEEE, United States (2010).

Swallow, E.B., et al., "A Novel Technique for Nonvolitional Assessment of Quadriceps Muscle Endurance in Humans," Journal of Applied Physiology 103(3):739-746, American Physiological Society, United States (Sep. 2007).

Szecsi, J., et al., "A Comparison of Functional Electrical and Magnetic Stimulation for Propelled Cycling of Paretic Patients," Archives of Physical Medicine and Rehabilitation 90(4):564-570, W.B. Saunders, United States, (Apr. 2009).

Szecsi, J., et al., "Force-pain Relationship in Functional Magnetic and Electrical Stimulation of Subjects With Paresis and Preserved Sensation," Clinical Neurophysiology 121(9):1589-1597, Elsevier, Netherlands, (Sep. 2010).

Taylor, J.L, "Magnetic Muscle Stimulation Produces Fatigue Without Effort," Journal of Applied Physiology (1985) 103(3):733-734, American Physiological Society, United States, (Sep. 2007).

Tesla Stym, Iskra Medical, Tone the inner muscle with FMS Functional Magnetic Stimulation, 2013, 4 pages.

The Burn Centre Care, Education, 3 pages, printed from internet Nov. 13, 2017.

The Magstim Company Ltd, K080499 510(k) Summary, Magstim Double 70mm Air Film Coil, All pages (Dec. 2008).

The Magstim Company Ltd., K130403 510(k) Summary, Magstim D702 coil, All pages (Aug. 2013).

Thermi Launches Arvati, powered by Thermi, with newest advances in True Temperature Controlled Radiofrequency Technology, 5 pages (2018).

Thermi Smooth TM 250, High Power Temperature Controlled Radio Frequency, Thermi Aesthetics, 25 pages.

Thompson, M.T., "Inductance Calculation Techniques—Part II: Approxmiations and Handbook Methods," Power Control and Intelligent Motion, 11 pages (Dec. 1999) http://www.pcim.com/.

Thompson, M.T., "Inductance Calculation Techniques—Part II: Classical Methods," Power Control and Intelligent Motion, 25(12):40-45, (Dec. 1999) http://www.pcim.com/.

Tomek, J., et al., "Magnetopneumography—Incorporation of optical position reference," Journal of Electrical Engineering, All pages (2012).

Torbergsen, T., "Abstracts of the International Course and Symposium in Single Fibre EMG and Quantitative EMG Analysis. Troms0, Norway, Jun. 4-8, 1984," Muscle & Nerve 9(6):562-574, John Wiley & Sons, United States (Jul.-Aug. 1986).

Trifractional FAQs, http://pollogen.lifvation.com/FAQ/TriFractional%20FAQs.pdf, Aug. 2011 (4pages).

TriLipo MED Procedure, http://download.lifvation.com/Maximus_TrilipoMED_Intro.pdf, Apr. 2013, 76 pages.

TSEM Med Swiss SA, Diamagnetic Therapy: A Revolutionary Therapy, CTU Mega 20 Catalogue, dated 2016, 24 pages, Lugano Switzerland.

Turley, J., "Agilent Technologies Announces 30 MHz Function/Arbitrary Waveform Generators with Unparalleled Signal Accuracy," Elec. Eng'g J., URL: (Aug. 4, 2010), 8 pages.

Ultra Slim Professional, The very best body Contouring, Wardphotonics LLC, 2018, 16 pages.

Unique Multi-Treatment Platform For, Feminine Health, Venus Fiore, 12 pages.

Urban, J., "Magnetotherapy and Physiotherapy," 40 pages.

URO Diagnostic Clinic, Now in UDC, Automated pelvic floor muscle training, QRS International AG, 16 Pages.

U.S. Appl. No. 60/848,720, inventor Burnett, D., filed on Sep. 30, 2006 (Not Published).

U.S. Appl. No. 62/331,060, inventor Schwarz, T., filed on May 3, 2016 (Not Published).

U.S. Appl. No. 62/331,072, inventor Schwarz, T., filed on May 3, 2016 (Not Published).

(56) References Cited

OTHER PUBLICATIONS

U.S. Appl. No. 62/331,088, inventor Schwarz, T., filed on May 3, 2016 (Not Published).
U.S. Appl. No. 62/333,666, inventor Schwarz, T., filed on May 9, 2016 (Not Published).
U.S. Appl. No. 62/351,156, inventor Schwarz, T., filed on Jun. 16, 2016 (Not Published).
U.S. Appl. No. 62/357,679, inventor Schwarz, T., filed on Jul. 1, 2016 (Not Published).
U.S. Appl. No. 62/440,905, inventors Schwarz, T. et al., filed on Dec. 30, 2016 (Not Published).
U.S. Appl. No. 62/440,912, inventors Schwarz, T. et al., filed on Dec. 30, 2016 (Not Published).
U.S. Appl. No. 62/440,922, inventor Schwarz, T., filed on Dec. 30, 2016 (Not Published).
U.S. Appl. No. 62/440,936, inventor Schwarz, T., filed on Dec. 30, 2016 (Not Published).
U.S. Appl. No. 62/440,940, inventor Schwarz, T., filed on Dec. 30, 2016 (Not Published).
U.S. Appl. No. 62/441,805, inventor Prouza, 0., filed on Jan. 3, 2017 (Not Published).
U.S. Appl. No. 62/786,731, inventor Schwarz, T., filed on Dec. 31, 2018 (Not Published).
User Guide: Mag Venture, Magpro family, MagPro R30, MagPro R30 with MagOption, MagPro X100, MagPro X100 with MagOption, MagPro software v.5.0, US-edition, MagPro family User Guide, 2010, 52 Pages.
User Guide, Salus Talent Pro, REMED, High Intensity Electro magnetic Field Therapy—2 Channel, 2017, Version M-1.0.0, 45 pages.
User Guide, Salus Talent, REMED, High Intensity Electro magnetic Field Therapy, Version. M-1.0.0, 2017, 40 pages.
User's Manual: BTL-6000, Super Inductive System Elite, BBTL Industries Ltd, United Kingdom, Sep. 2016, 36 pages.
User Manual: Electro-magnetic Stimulator, Salus-Talent, Version 1.00, Rehabilitation Medical Company,2013, 34 Pages.
User Manual: Regenetron Pro, System Information, Regenetron Pro User Manual, Nov. 2014, 7 Pages.
Vance, C., et al., "Effects of Transcutaneous Electrical Nerve Stimulation on Pain, Pain Sensitivity, and Function in People with Knee Osteoarthritis," Physical Therapy 92:898-910 (2012).
Vanquish Operator's Manual, BTL, 2012, 48 Pages.
Venus, Venus legacy marca argentina, Oct. 14, 2014, 20 pages.
Venus Concept Ltd., VenusFreeze MP2, User Manual, dated Jun. 2012, 46 pages.
Venus Concept Ltd., VenusViva, User Manual, dated Aug. 2013, 51 pages.
Venus Legacy, Featuring LiftFX and SculptFX, Venus Concept, Delivering the Promise, 24 pages.
Venus Legacy, User Manual International, 2009, Venus Concept, 49 pages.
Venus Swan, Experience the Difference, Venus Concept, Delivering the Promise, http://www.medicom.cz/UserFiles/File/LekarskeNenue/020Swan%20EN.pdf, 2 pages (Apr. 2016).
VenusFreeze, Experience the Energy, Venus Concept, Delivering the Promise, 2 pages.
Verges S., et al., "Comparison of Electrical and Magnetic Stimulations to Assess Quadriceps Muscle Function," Journal of Applied Physiology (1985) 106(2):701-710, American Physiological Society, United States, (Feb. 2009).
Wada, K., et al., "Design and Implementation of Multi-Frequency Magnetic Field Generator Producing Sinusoidal Current Waveform for Biological Researches," IEEE, 9 pages (2016).
Wanitphakdeedecha, R., et al., "Treatment of Abdominal Cellulite and Circumference Reduction With Radiofrequency and Dynamic Muscle Activation" Journal of Cosmetic and Laser Therapy 17(5):246-251, Informa Healthcare, England (2015).
Ward, A.R. and Shkuratova, N., "Russian Electrical Stimulation: The Early Experiments," Physical therapy 82(10):1019-1030, Oxford University Press, United States (2002).
Wasilewski, M.L., Academy of Aesthetic and Anti-Aging Medicine, Application of magnetic fields with deep stimulation in the fight against local obesity of lower limbs, BTL, 2012, 4 pages.
Web MD, what is normal body temperature? 3 pages, printed Mar. 4, 2019.
Weight to volume aluminum, 2 pages. printed from internet Sep. 25, 2018.
Weight to volume copper, 2 pages printed from internet Sep. 25, 2018.
Weiss, R.A., et al., "Induction of Fat Apoptosis by a Non-Thermal Device: Mechanism of Action of Non-Invasive High-Intensity Electromagnetic Technology in a Porcine Model," Lasers in surgery and medicine 51(1):47-53, Wiley-Liss, United States (Jan. 2019).
Weng, 0., "Electromagnetic Activation of the Calf Muscle Pump," UMI Dissertation Publishing (2014).
Woehrle, J., et al., "Dry Needling and its Use in Health Care—A Treatment Modality and Adjunct for Pain Management," Journal of Pain & Relief 4(5):1-3, (Aug. 2015).
Yacyshy, A.F., et al., "The Inclusion of Interstimulus Interval Variability Does Not Mitigate Electrically-evoked Fatigue of the Knee Extensors," European Journal of Applied Physiology 120(12):2649-2656, Springer-Verlag, Germany (Sep. 2020).
Z Wave, Instructions for Use, Zimmer Aesthetic Division, Version 5, 44 pages.
Zao 0KB Ritm, Electroneurostimulants, Transdermal Scenar-NT Instructions, All Pages (Nov. 2013).
Zao 0KB Ritm, Percutaneous Electrical Stimulators With Individual Biofeedback Dosing Impact on Reflex Zones, All pages (2017).
Zelickson, B., et al.."Cryolipolysis for Noninvasive Fat Cell Destruction: Initial Results From a Pig Model," Dermatologic Surgery 35(10):1462-1470, Hagerstown, MD Lippincott, Williams & Wilkins, United States (Oct. 2009).
Zeltiq System User Manual—Print and Binding Specifications, Zeltiq Aesthetics, Inc, Mar. 2011, 88 pages.
Zerona, Reveal your True Shape, Product Fact Sheet, 3 pages.
Zerona R-Z6 by Erchonia, Specifications,Retrieved from the Internet: (www.myzerona.com), 2015, 1 page.
Zhang, G., et al., "A Method of Nerve Electrical Stimulation by Magnetic Induction," Annual International Conference of the IEEE Engineering in Medicine and Biology Society 2009:622-625, IEEE, United States (2009).
Zhi-De, D., "Electromagnetic Field Modeling of Transcranial Electric and Magnetic Stimulation: Targeting, Individualization, and Safety of Convulsive and Subconvulsive Applications," Academic Commons (2013).
Zhu, Y., et al., "Magnetic Stimulation of Muscle Evokes Cerebral Potentials by Direct Activation of Nerve Afferents: A Study During Muscle Paralysis," Muscle & Nerve 19(12):1570-1575, John Wiley & Sons, United Sates (Dec. 1996).
Pascual-Leone, Alvaro et al. "Handbook of Transcranial Magnetic Stimulation" 2002 Arnold Publishers, Chapters 1-4, 58 pages.
Mantis, The non-invasive solution that restores natural beauty, improves health, and offers a renewed psychophysical sense of balance, MR991 theramagnetic, 2020, 8 pages.
Mantis Theramagnetic Compact: the compact that guarantees utmost efficiency and maximum performance, theramagnetic, 2020, 8 pages.
Pollegen, K200545, Legend Pro OMA, Indications for use, dated Oct. 20, 2021, 11 pages.
Jalinous, R., "Technical and Practical Aspects of Magnetic Nerve Stimulation," Journal of Clinical Neurophysiology 8(1):10-25, Lippincott Williams & Wilkins, United States (Jan. 1991).
*Lumenis Be Ltd.* v. *BTL Healthcare Technologies A.S.*, PTAB-IPR2022-00451, Declaration of Dr. Marom Bikson (EX1002), Jan. 24, 2022, 236 pages.
*Lumenis Be Ltd.* v. *BTL Healthcare Technologies A.S.*, PTAB-IPR2022-00451, U.S. Pat. No. 10,806,943 Petition for Inter Partes Review, Jan. 24, 2022, 87 pages.
*Lumenis Be Ltd.* v. *BTL Healthcare Technologies A.S.*, PTAB-IPR2022-00452, Declaration of Dr. Marom Bikson (EX1002), Jan. 24, 2022, 229 pages.
*Lumenis Be Ltd.* v. *BTL Healthcare Technologies A.S.*, PTAB-IPR2022-00452, U.S. Pat. No. 10,806,943 Petition for Inter Partes Review, Jan. 24, 2022, 81 pages.

(56) References Cited

OTHER PUBLICATIONS

Operating Manual: Magstim® 2002, P/N 3001-23-04, The Magstim Company Limited, Mar. 18, 2005, 34 pages.
Stallknecht, B., et al., "Are Blood Flow and Lipolysis in Subcutaneous Adipose Tissue Influenced by Contractions in Adject Muscles in Humans?," American Journal of Physiology. Endocrinology and Metabolism 292(2):E394-E399, American Physiological Society, United States (Feb. 2007).
Weyh, T., et al., "Marked Differences in the Thermal Characteristics of Figure-of-eight Shaped Coils Used for Repetitive Transcranial Magnetic Stimulation," Clinical Neurophysiology 116(6):1477-1486, Elsevier, Netherlands (Mar. 2005).

\* cited by examiner

DEVICE AND METHOD FOR UNATTENDED TREATMENT OF A PATIENT

CROSS-REFERENCE TO RELATED APPLICATIONS

This application is a continuation of U.S. patent application Ser. No. 17/661,406, filed Apr. 29, 2022, which is a continuation of U.S. patent application Ser. No. 17/576,646, filed Jan. 14, 2022, which is a continuation of PCT Application No. PCT/IB2021/00300, filed May 3, 2021, which claims priority to U.S. Provisional Application No. 63/019,619, filed May 4, 2020. All above mentioned applications are incorporated herein by reference in their entirety.

FIELD OF THE INVENTION

The present invention relates to methods and apparatus for patient treatment by means of active elements delivering electromagnetic energy and/or secondary energy in such a way that the treatment area is treated homogeneously without the need for manipulation of the active elements during the therapy.

BACKGROUND OF THE INVENTION

Delivering various forms of electromagnetic energy into the patient for medical and cosmetic purposes has been widely used in the past. These common procedures include, but are by no means limited to, skin rejuvenation, wrinkle removal, skin tightening and lifting, cellulite and fat reduction, treatment of pigmented lesions, tattoo removal, soft tissue coagulation and ablation, vascular lesion reduction, face lifting, muscle contractions and muscle strengthening, etc.

All of these procedures are performed to improve a visual appearance of the patient.

Besides many indisputable advantages of a thermal therapy, these procedures also bring certain limitations and associated risks. Among others is the limited ability of reproducible results as these are highly dependent on applied treatment techniques and the operator's capabilities. Moreover, if the therapy is performed inappropriately, there is an increased risk of burns and adverse events.

It is very difficult to ensure a homogeneous energy distribution if the energy delivery is controlled via manual movement of the operator's hand which is the most common procedure. Certain spots can be easily over- or under-treated. For this reason, devices containing scanning or other mechanisms capable of unattended skin delivery have emerged. These devices usually deliver energy without direct contact with the treated area, and only on a limited, well-defined area without apparent unevenness. Maintaining the same distance between the treated tissue and the energy generator or maintaining the necessary tissue contact may be challenging when treating uneven or rugged areas. Therefore, usage of commonly available devices on such specific areas that moreover differ from patient to patient (e.g. the face) might be virtually impossible.

Facial unattended application is, besides the complications introduced by attachment to rugged areas and necessity of adaptation to the shapes of different patients, specific by its increased need for protection against burns and other side effects. Although the face heals more easily than other body areas, it is also more exposed, leading to much higher requirements for treatment downtime. Another important aspect of a facial procedure is that the face hosts the most important human senses, whose function must not be compromised during treatment. Above all, eye safety must be ensured throughout the entire treatment.

The current aesthetic market offers either traditional manually controlled radiofrequency or light devices enabling facial tissue heating to a target temperature in the range of 40° C.-100° C. or unattended LED facial masks whose operation is based on light effects (phototherapy) rather than thermal effects. These masks are predominantly intended for home use and do not pose a risk to patients of burns, overheating or overtreating. The variability in facial shapes of individual patients does not represent any issue for these masks as the delivered energy and attained temperatures are so low that the risk of thermal tissue damage is minimized and there is no need for homogeneous treatment. Also, due to low temperatures, it is not important for such devices to maintain the predetermined distance between the individual diodes and the patient's skin, and the shape of the masks is only a very approximate representation of the human face. But their use is greatly limited by the low energy and minimal to no thermal effect and they are therefore considered as a preventive tool for daily use rather than a method of in-office skin rejuvenation with immediate effect.

Nowadays, the aesthetic market feels the needs of the combination of the heating treatment made by electromagnetic energy delivered to the epidermis, dermis, hypodermis or adipose tissue with the secondary energy providing muscle contraction or muscle stimulation in the field of improvement of visual appearance of the patient. However, none of the actual devices is adapted to treat the uneven rugged areas like the face. In addition, the commercially available devices are usually handheld devices that need to be operated by the medical professional during the whole treatment.

Thus it is necessary to improve medical devices providing more than one treatment energy (e.g. electromagnetic energy and electric current), such that both energies may be deliver via different active elements or the same active element (e.g. electrode). Furthermore, the applicator or pad of the device needs to be attached to the patient which allows unattended treatment of the patient and the applicator or pad needs to be made of flexible material allowing sufficient contact with the uneven treatment area of the body part of the patient.

SUMMARY OF THE INVENTION

In order to enable well defined unattended treatment of the uneven, rugged areas of a patient (e.g. facial area) while preserving safety, methods and devices of minimally invasive to non-invasive electromagnetic energy delivery via a single or a plurality of active elements have been proposed.

The patient may include skin and a body part, wherein a body part may refer to a body area.

The desired effect of the improvement of visual appearance of the patient may include tissue (e.g. skin) heating in the range of 40° C. to 50° C., tissue coagulation at temperatures of 40° C. to 80° C. or tissue ablation at temperatures of 60° C. to 100° C. Various patients and skin conditions may require different treatment approaches—higher temperatures allow better results with fewer sessions but require longer healing times while lower temperatures enable treatment with no downtime but limited results within more sessions. Another effect of the heating may lead to decreasing the number of the fat cells.

Another desired effect may be muscle contraction causing muscle stimulation (e.g. strengthening or toning) for improving the visual appearance of the patient.

An arrangement for contact or contactless therapy has been proposed.

For contact therapy, the proposed device comprises at least one electromagnetic energy generator inside a main unit that generates an electromagnetic energy which is delivered to the treatment area via at least one active element attached to the skin. At least one active element may be embedded in a pad made of flexible material that adapts to the shape of the rugged surface. An underside of the pad may include of an adhesive layer allowing the active elements to adhere to the treatment area and to maintain necessary tissue contact. Furthermore, the device may employ a safety system capable of adjusting one or more therapy parameters based on the measured values from at least one sensor, e.g. thermal sensors or impedance measurement sensors capable of measuring quality of contact with the treated tissue.

For contactless therapy, the proposed device comprises at least one electromagnetic energy generator inside a main unit that generates an electromagnetic energy which is delivered to the treatment area via at least one active element located at a defined distance from the tissue to be treated. A distance of at least one active element from the treatment area may be monitored before, throughout the entire treatment or post-treatment. Furthermore, the device may employ a safety system capable of adjusting one or more therapy parameters based on the measured values from at least one sensor, for example one or more distance sensors. Energy may be delivered by a single or a plurality of static active elements or by moving a single or a plurality of active elements throughout the entire treatment area, for example via a built-in automatic moving system, e.g. an integrated scanner. Treatment areas may be set by means of laser sight—the operator may mark the area to be treated prior to the treatment.

The active element may deliver energy through its entire surface or by means of a so-called fractional arrangement when the active part includes a matrix formed by points of defined size. These points may be separated by inactive (and therefore untreated) areas that allow faster tissue healing. The points surface may make up from 1% to 99% of the active element area.

The electromagnetic energy may be primarily generated by a laser, laser diode module, LED, flash lamp or incandescent light bulb or by radiofrequency generator for causing the heating of the patient. Additionally, an acoustic energy or electric or electromagnetic energy, which does not heat the patient, may be delivered simultaneously, alternately or in overlap with the primary electromagnetic energy.

The active element may deliver more than one energy simultaneously (at the same time), successively or in overlap. For example, the active element may deliver a radiofrequency energy and subsequently an electric energy (electric current). In another example, the active element may deliver the radiofrequency energy and the electric energy at the same time.

Furthermore the device may be configured to deliver the electromagnetic field by at least one active element and simultaneously (at the same time) to deliver e.g. electric energy by a different elements.

Thus the proposed methods and devices may lead to proper skin rejuvenation, wrinkle removal, skin tightening and lifting, cellulite and fat reduction, treatment of pigmented lesions, tattoo removal, soft tissue coagulation and ablation, vascular lesions reduction, etc. of uneven rugged areas without causing further harm to important parts of the patient's body, e.g. nerves or internal organs. The proposed method and devices may lead to an adipose tissue reduction, e.g. by fat cells lipolysis or apoptosis.

Furthermore, the proposed methods and devices may lead to tissue rejuvenation, e.g. muscle strengthening or muscle toning through the muscle contraction caused by electric or electromagnetic energy.

DETAILED DESCRIPTION

Figure 1:
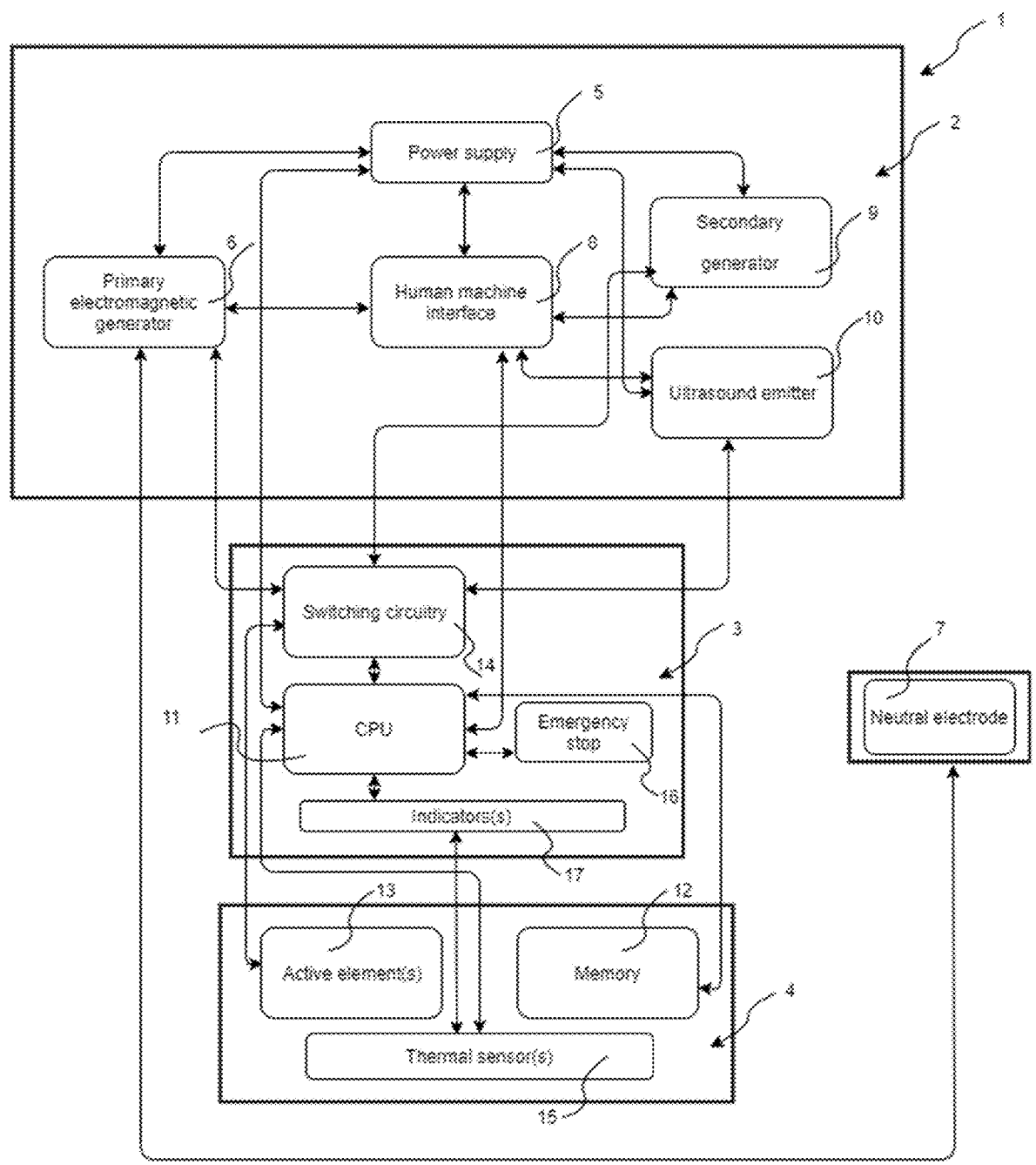
FIG. 1 shows a block diagram of an apparatus for contact therapy.

The presented methods and devices may be used for stimulation and/or treatment of a tissue, including but not limited to skin, epidermis, dermis, hypodermis or muscles. The proposed apparatus is designed for minimally to non-invasive treatment of one or more areas of the tissue to enable well defined unattended treatment of the uneven, rugged areas (e.g. facial area) by electromagnetic energy delivery via a single or a plurality of active elements without causing further harm to important parts of the patient's body, e.g. nerves or internal organs.

Additionally the presented methods and devices may be used to stimulate body parts or body areas like head, neck, bra fat, love handles, torso, back, abdomen, buttocks, thighs, calves, legs, arms, forearms, hands, fingers or body cavities (e.g. vagina, anus, mouth, inner ear etc.).

The proposed methods and devices may include a several protocols improving of visual appearance, which may be preprogramed in the control unit (e.g. CPU which may include a flex circuit or a printed circuit board and may include a microprocessor or memory for controlling the device)).

The desired effect may include tissue (e.g. skin) heating (thermal therapy) in the range of 37.5° C. to 65° C. or in the range of 38° C. to 60° C. or in the range of 39° C. to 55° C. or in the range of 40° C. to 50° C., tissue coagulation at temperatures in the range of 37.5° C. to 95° C. or in the range of 38° C. to 90° C. or in the range of 39° C. to 85° C. or in the range of 40° C. to 80° C. or tissue ablation at temperatures in the range of 50° C. to 130° C. or in the range of 55° C. to 120° C. or in the range of 60° C. to 110° C. or in the range of 60° C. to 100° C. The device may be operated in contact or in contactless methods. For contact therapy a target temperature of the skin may be typically within the range of 37.5° C. to 95° C. or in the range of 38° C. to 90° C. or in the range of 39° C. to 85° C. or in the range of 40° C. to 80° C. while for contactless therapy a target temperature of the skin may be in the range of 37.5° C. to 130° C. or in the range of 38° C. to 120° C. or in the range of 39° C. to 110° C. or in the range of 40° C. to 100° C. The temperature within the range of 37.5° C. to 130° C. or in the range of 38° C. to 120° C. or in the range of 39° C. to 110° C. or in the range of 40° C. to 100° C. may lead to stimulation of fibroblasts and formation of connective tissue—e.g. collagen, elastin, hyaluronic acid etc. Depending on the target temperature, controlled tissue damage is triggered, physiological repair processes are initiated, and new tissue is formed. Temperatures within the range of 37.5° C. to 130° C. or in the range of 38° C. to 120° C. or in the range of 39° C. to 110° C. or in the range of 40° C. to 100° C. may further lead to changes in the adipose tissue. During the process of apoptosis caused by high temperatures, fat cells come apart into apoptotic bodies and are further removed via the process of phagocytosis. During a process called necrosis, fat cells are ruptured due to high temperatures, and their content is released into an extracellular matrix. Both processes may lead to a reduction of fat layers enabling reshaping of the face. Removing fat from the face may be beneficial for example in areas like submentum or cheeks.

Another desired effect may include tissue rejuvenation, e.g. muscle strengthening through the muscle contraction caused by electric or electromagnetic energy, which doesn't heat the patient, or the muscle relaxation caused by a pressure massage. The combined effect of muscle contractions via electric energy and tissue (e.g. skin) heating by electromagnetic field in accordance to the description may lead to significant improvement of visual appearance.

Figure 2:
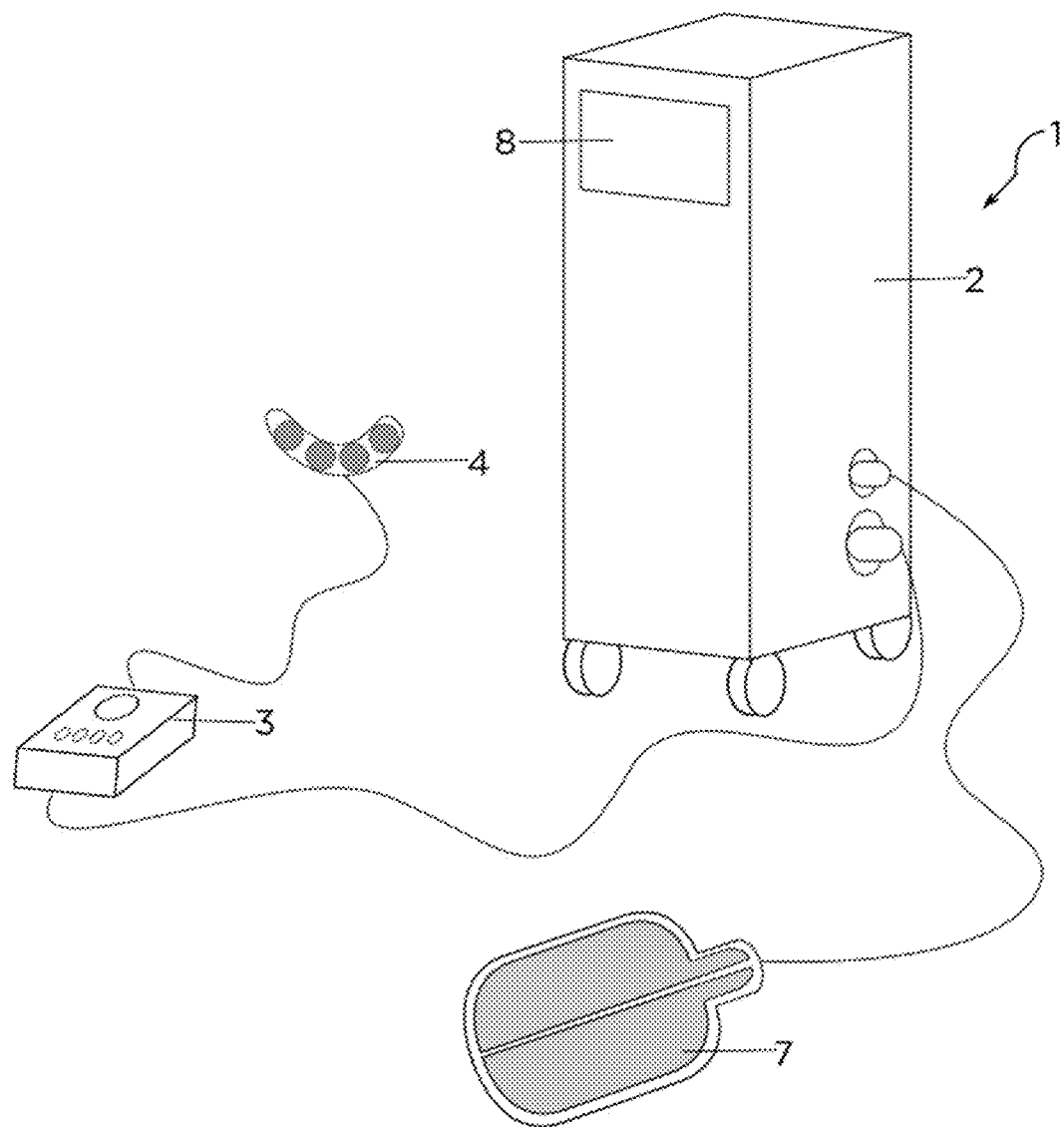
FIG. 2 is an illustration of an apparatus for contact therapy.

FIG. 1 and FIG. 2 are discussed together. FIG. 1 shows a block diagram of an apparatus for contact therapy 1. FIG. 2 is an illustration of an apparatus for contact therapy 1. The apparatus for contact therapy 1 may comprise two main blocks: main unit 2 and pad 4. Additionally, the apparatus 1 may comprise interconnecting block 3 or neutral electrode 7. However, the components of interconnecting block 3, may be implemented into the main unit 2.

Main unit 2 may include one or more generators: a primary electromagnetic generator 6 which may preferably deliver radiofrequency energy in the range of 10 kHz to 300 GHz or 300 kHz to 10 GHz or 400 kHz to 6 GHz, or in the range of 100 kHz to 550 MHz or 250 kHz to 500 MHz or 350 kHz to 100 MHz or 400 kHz to 80 MHz, a secondary generator 9 which may additionally deliver electromagnetic energy, which does not heat the patient, or deliver electric current in the range of 1 Hz to 10 MHz or 5 Hz to 5 MHz or in the range of 10 Hz to 1 MHz and/or an ultrasound emitter 10 which may furthermore deliver an acoustic energy with a frequency in the range of 20 kHz to 25 GHz or 20 kHz to 1 GHz or 50 kHz to 250 MHz or 100 kHz to 100 MHz. In addition, the frequency of the ultrasound energy may be in the range of 20 kHz to 80 MHz or 50 kHz to 50 MHz or 150 kHz to 20 MHz.

The output power of the radiofrequency energy may be less than or equal to 450, 300, 250 or 220 W. Additionally, the radiofrequency energy on the output of the primary electromagnetic generator 6 (e.g. radiofrequency generator) may be in the range of 0.1 W to 400 W, or in the range of 0.5 W to 300 W or in the range of 1 W to 200 W or in the range of 10 W to 150 W. The radiofrequency energy may be applied in or close to the ISM bands of 6.78 MHz, 13.56 MHz, 27.12 MHz, 40.68 MHz, 433.92 MHz, 915 MHz, 2.45 GHz and 5.8 GHz.

Main unit 2 may further comprise a human machine interface 8 represented by a display, buttons, a keyboard, a touchpad, a touch panel or other control members enabling an operator to check and adjust therapy and other device parameters. For example, it may be possible to set the power, treatment time or other treatment parameters of each generator (primary electromagnetic generator 6, secondary generator 9 and ultrasound emitter 10) independently. The human machine interface 8 may be connected to CPU 11. The power supply 5 located in the main unit 2 may include a transformer, disposable battery, rechargeable battery, power plug or standard power cord. The output power of the power supply 5 may be in the range of 10 W to 600 W, or in the range of 50 W to 500 W, or in the range of 80 W to 450 W.

Interconnecting block 3 may serve as a communication channel between main unit 2 and pad 4. It may be represented by a simple device containing basic indicators 17 and mechanisms for therapy control. Indicators 17 may be realized through the display, LEDs, acoustic signals, vibrations or other forms capable of providing adequate notice to an operator and/or the patient. Indicators 17 may indicate actual patient temperature, contact information or other sensor measurements as well as a status of a switching process between the active elements, quality of contact with the treated tissue, actual treatment parameters, ongoing treatment, etc. Indicators 17 may be configured to warn the operator in case of suspicious therapy behavior, e.g. temperature out of range, improper contact with the treated tissue, parameters automatically adjusted etc. Interconnecting block 3 may be used as an additional safety feature for heat-sensitive patients. It may contain emergency stop button 16 so that the patient can stop the therapy immediately anytime during the treatment. Switching circuitry 14 may be responsible for switching between active elements or for regulation of energy delivery from primary electromagnetic generator 6, secondary generator 9 or ultrasound emitter 10. The rate of switching between active elements 13 may be dependent on the amount of delivered energy, pulse length etc, and/or on the speed of switching circuitry 14 and CPU 11. The switching circuitry 14 may include relay switch, transistor (bipolar, PNP, NPN, FET, JFET, MOSFET) thyristor, diod or opto-mechanical switch or any other suitable switch know in the prior art. The switching circuitry in connection with the CPU may control the switching between the primary electromagnetic energy generated by the primary electromagnetic generator 6 and the secondary energy generated by the secondary generator 9 on the at least one active element.

Additionally, the interconnecting block 3 may contain the primary electromagnetic generator 6, the secondary generator 9 or ultrasound emitter 10 or only one of them or any combination thereof.

The CPU 11 controls the primary electromagnetic generator 6 such that the primary electromagnetic energy may be delivered in a continuous mode (CM) or a pulse mode to the at least one active element, having a fluence in the range of 10 mJ/cm$^2$ to 50 kJ/cm$^2$ or in the range of 100 mJ/cm$^2$ to 10 kJ/cm$^2$ or in the range of 0.5 J/cm$^2$ to 1 kJ/cm$^2$. The electromagnetic energy may be primarily generated by a laser, laser diode module, LED, flash lamp or incandescent light bulb or by radiofrequency generator for causing the heating of the patient. The CM mode may be operated for a time interval in the range of 0.05 s to 60 min or in the range of 0.1 s to 45 min or in the range of 0.2 s to 30 min. The pulse duration of the energy delivery operated in the pulse regime may be in the range of 0.1 ms to 10 s or in the range of 0.2 ms to 7 s or in the range of 0.5 ms to 5 s. The primary electromagnetic generator 6 in the pulse regime may be operated by CPU 11 in a single shot mode or in a repetition mode. The frequency of the repetition mode may be in the range of 0.05 to 10 000 Hz or in the range of 0.1 to 5000 Hz or in the range of 0.3 to 2000 Hz or in the range of 0.5 to 1000 Hz. Alternatively, the frequency of the repetition mode may be in the range of 0.1 kHz to 200 MHz or in the range of 0.5 kHz to 150 MHz or in the range of 0.8 kHz to 100 MHz or in the range of 1 kHz to 80 MHz. The single shot mode may mean generation of just one electromagnetic pulse of specific parameters (e.g. intensity, duration, etc.) for delivery to a single treatment area. The repetition mode may mean generation of an electromagnetic pulses, which may have the specific parameters (e.g. intensity, duration, etc.), with a repetition rate of the above-mentioned frequency for delivery to a single treatment area. The CPU 11 may provide treatment control such as stabilization of the treatment parameters including treatment time, power, duty cycle, time period regulating switching between multiple active elements, temperature of the device 1 and temperature of the primary electromagnetic generator 6 and secondary generator 9 or ultrasound emitter 10. The CPU 11 may drive and provide information from the switching circuitry 14. CPU 11 may also receive and provide information from sensors located on or in the pad 4 or anywhere in the device 1. The CPU 11 may include a flex circuit or a printed circuit board and may include a microprocessor or memory for controlling the device.

The CPU 11 may control the secondary generator 9 such that secondary energy (e.g electric current or magnetic field) may be delivered in a continuous mode (CM) or a pulse mode to the at least one active element, having a fluence in the range of 10 mJ/cm$^2$ to 50 kJ/cm$^2$ or in the range of 100 mJ/cm$^2$ to 10 kJ/cm$^2$ or in the range of 0.5 J/cm$^2$ to 1 kJ/cm$^2$ on the surface of the at least one active element. Applying the secondary energy to the treatment area of the patient may cause a muscle contractions of the patient. The CM mode may be operated for a time interval in the range of 0.05 s to 60 min or in the range of 0.1 s to 45 min or in the range of 0.2 s to 30 min. The pulse duration of the delivery of the secondary energy operated in the pulse regime may be in the range of 0.1 us to 10 s or in the range of 0.2 us to 1 s or in the range of 0.5 us to 500 ms. The secondary generator 9 in the pulse regime may be operated by CPU 11 in a single shot mode or in a repetition mode. The frequency of the repetition mode may be in the range of 0.1 to 12 000 Hz or in the range of 0.1 to 8000 Hz or in the range of 0.1 to 5000 Hz or in the range of 0.5 to 1000 Hz.

The proposed device may be multichannel device allowing the CPU 11 to control the treatment of more than one treated area at once.

Alternatively, the interconnecting block 3 may not be a part of the device 1, and the CPU 11, switching circuitry 14, indicators 17 and emergency stop 16 may be a part of the main unit 2 or pad 4. In addition, some of the CPU 11, switching circuitry 14, indicators 17 and emergency stop 16 may be a part of the main unit 2 and some of them part of pad 4, e.g. CPU 11, switching circuitry 14 and emergency stop 16 may be part of the main unit 2 and indicators 17 may be a part of the pad 4.

Pad 4 represents the part of the device which may be in contact with the patient's skin during the therapy. The pads 4 may be made of flexible substrate material—for example polymer-based material, polyimide (PI) films, teflon, epoxy, polyethylene terephthalate (PET), polyamide or PE foam with an additional adhesive layer on an underside, e.g. a hypoallergenic adhesive gel or adhesive tape that may be bacteriostatic, non-irritating, or water-soluble. The substrate may also be a silicone-based substrate. The substrate may also be made of a fabric, e.g. non-woven fabric. The adhesive layer may have the impedance for a current at a frequency of 500 kHz in the range of 1 to 150 Ω or in the range of 5 to 130 Ω or in the range of 10 to 100Ω, and the impedance for a current at a frequency of 100 Hz or less is three times or more the impedance for a current at a frequency of 500 kHz. The adhesive hydrogel may be made of a polymer matrix or mixture containing water, a polyhydric alcohol, a polyvinylpyrrolidone, a polyisocyanate component, a polyol component or has a methylenediphenyl structure in the main chain. Additionally, a conductive adhesive may be augmented with metallic fillers, such as silver, gold, copper, aluminum, platinum or titanium or graphite that make up 1 to 90% or 2 to 80% or 5 to 70% of adhesive. The adhesive layer may be covered by "ST-Gel®" or "Tensive®" conductive adhesive gel which is applied to the body to reduce its impedance, thereby facilitating the delivery of an electric shock.

The adhesive layer under the pad 4 may mean that the adhesive layer is between the surface of the pad facing the patient and the body of the patient. The adhesive layer may have impedance 1.1 times, 2 times, 4 times or up to 10 times higher than the impedance of the skin of the patient under the pad 4. A definition of the skin impedance may be that it is a portion of the total impedance, measured between two equipotential surfaces in contact with the epidermis, that is inversely proportional to the electrode area, when the internal current flux path is held constant. Data applicable to this definition would be conveniently recorded as admittance per unit area to facilitate application to other geometries. The impedance of the adhesive layer may be set by the same experimental setup as used for measuring the skin impedance. The impedance of the adhesive layer may be higher than the impedance of the skin by a factor in the range of 1.1 to 20 times or 1.2 to 15 times or 1.3 to 10 times.

The impedance of the adhesive layer may have a different values for the different types of energy delivered to the patient, e.g. the impedance may be different for radiofrequency and for electric current delivery. The impedance of the hydrogel may be in the range of 100 to 2000 Ohm or in the range of 150 to 1800 Ohm or 200 to 1500 Ohm or 300 to 1200 Ohm in case of delivery of the electric current (e.g. during electrotherapy)

The pad 4 may also have a sticker on a topside of the pad. The topside is the opposite site of the underside (the side where the adhesive layer may be deposited) or in other words the top side is the side of the pad that is facing away from the patient during the treatment. The sticker may have a bottom side and a top side, wherein the bottom side of the sticker may comprise a sticking layer and the top side of the sticker may comprise non-sticking layer (eg. polyimide (PI) films, teflon, epoxy, polyethylene terephthalate (PET), polyamide or PE foam).

The sticker may have the same shape as the pad 4 or may have additional overlap over the pad. The sticker may be bonded to the pad such that the sticking layer of the bottom side of the sticker is facing towards the topside of the pad 4. The top side of the sticker facing away from the pad 4 may be made of a non-sticking layer. The size of the sticker with additional overlap may exceed the pad in the range of 0.1 to 10 cm, or in the range of 0.1 to 7 cm, or in the range of 0.2 to 5 cm, or in the range of 0.2 to 3 cm. This overlap may also comprise the sticking layer and may be used to form additional and more proper contact of the pad with the patient.

Alternatively, the pad 4 may comprise at least one suction opening, e.g. small cavities or slits adjacent to active elements or the active element may be embedded inside a cavity. The suction opening may be connected via connecting tube to a pump which may be part of the main unit 2. When the suction opening is brought into contact with the skin, the air sucked from the suction opening flows toward the connecting tube and the pump and the skin may be slightly sucked into the suction opening. Thus by applying a vacuum the adhesion of pad 4 may be provided. Furthermore, the pad 4 may comprise the adhesive layer and the suction openings for combined stronger adhesion.

In addition to the vacuum (negative pressure), the pump may also provide a positive pressure by pumping the fluid to the suction opening. The positive pressure is pressure higher than atmospheric pressure and the negative pressure or vacuum is lower than atmospheric pressure. Atmospheric pressure is a pressure of the air in the room during the therapy.

The pressure (positive or negative) may be applied to the treatment area in pulses providing a massage treatment. The massage treatment may be provided by one or more suction openings changing pressure value to the patient's soft tissue in the meaning that the suction opening apply different pressure to patient tissue. Furthermore, the suction openings may create a pressure gradient in the soft tissue without touching the skin. Such pressure gradients may be targeted on the soft tissue layer, under the skin surface and/or to different soft tissue structure.

Massage accelerates and improves treatment therapy by electromagnetic energy, electric energy or electromagnetic energy which does not heat the patient, improves blood and/or lymph circulation, angioedema, erythema effect, accelerates removing of the fat, accelerate metabolism, accelerates elastogenesis and/or neocolagenesis.

Each suction opening may provide pressure by a suction mechanism, airflow or gas flow, liquid flow, pressure provided by an object included in the suction opening (e.g. massaging object, pressure cells etc.) and/or in other ways.

Pressure value applied on the patient's tissue means that a suction opening providing massaging effect applies positive, negative and/or sequentially changing positive and negative pressure on the treated and/or adjoining patient's tissue structures and/or creates a pressure gradient under the patient's tissue surface Massage applied in order to improve body liquid flow (e.g. lymph drainage) and/or relax tissue in the surface soft tissue layers may be applied with pressure lower than during the massage of deeper soft tissue layers. Such positive or negative pressure compared to the atmospheric pressure may be in range of 10 Pa to 30 000 Pa, or in range of 100 Pa to 20 000 Pa or in range of 0.5 kPa to 19 kPa or in a range of 1 kPa to 15 kPa.

Massage applied in order to improve body liquid flow and/or relaxation of the tissue in the deeper soft tissue layers may be applied with higher pressure. Such positive or negative pressure may be in range from 12 kPa to 400 kPa or from 15 kPa to 300 kPa or from 20 kPa to 200 kPa. An uncomfortable feeling of too high applied pressure may be used to set a pressure threshold according to individual patient feedback.

Negative pressure may stimulate body liquid flow and/or relaxation of the deep soft tissue layers (0.5 cm to non-limited depth in the soft tissue) and/or layers of the soft tissue near the patient surface (0.1 mm to 0.5 cm). In order to increase effectiveness of the massage negative pressure treatment may be used followed by positive pressure treatment.

A number of suction openings changing pressure values on the patient's soft tissue in one pad 4 may be between 1 to 100 or between 1 to 80 or 1 to 40 or between 1 to 10.

Sizes and/or shapes of suction openings may be different according to treated area. One suction opening may cover an area on the patient surface between 0.1 mm2 to 1 cm2 or between 0.1 mm2 to 50 mm2 or between 0.1 mm2 to 40 mm2 or between 0.1 mm2 to 20 mm2. Another suction opening may cover an area on the patient surface between 1 cm2 to 1 m2 or between 1 cm2 to 100 cm2 or between 1 cm2 to 50 cm2 or between 1 cm2 to 40 cm2.

Several suction openings may work simultaneously or switching between them may be in intervals between 1 ms to 10 s or in intervals between 10 ms to 5 s or in intervals between 0.5 s to 2 s.

Suction openings in order to provide massaging effect may be guided according to one or more predetermined massage profile included in the one or more treatment protocols. The massage profile may be selected by the operator and/or by a CPU with regard to the patient's condition. For example a patient with lymphedema may require a different level of compression profile and applied pressure than a patient with a healed leg ulcer.

Pressure applied by one or more suction openings may be gradually applied preferably in the positive direction of the lymph flow and/or the blood flow in the veins. According to specific treatment protocols the pressure may be gradually applied in a direction opposite or different from ordinary lymph flow. Values of applied pressure during the treatment may be varied according to the treatment protocol.

A pressure gradient may arise between individual suction openings. Examples of gradients described are not limited for this method and/or device. The setting of the pressure gradient between at least two previous and successive suction openings may be: 0%, i.e. The applied pressure by suction openings is the same (e.g. pressure in all suction openings of the pad is the same);

1%, i.e. The applied pressure between a previous and a successive suction opening decreases and/or increases with a gradient of 1% (e.g. the pressure in the first suction opening is 5 kPa and the pressure in the successive suction opening is 4.95 kPa);

2%, i.e. The pressure decreases or increases with a gradient of 2%. The pressure gradient between two suction openings may be in range 0% to 100% where 100% means that one suction openings is not active and/or does not apply any pressure on the patient's soft tissue.

A treatment protocol that controls the application of the pressure gradient between a previous and a successive suction opening may be in range between 0.1% to 95%, or in range between 0.1% to 70%, or in range between 1% to 50%.

The suction opening may also comprise an impacting massage object powered by a piston, massage object operated by filling or sucking out liquid or air from the gap volume by an inlet/outlet valve or massage object powered by an element that creates an electric field, magnetic field or electromagnetic field. Additionally, the massage may be provided by impacting of multiple massage objects. The multiple massage objects may have the same or different size, shape, weight or may be created from the same or different materials. The massage objects may be accelerated by air or liquid flowing (through the valve) or by an electric, magnetic or electromagnetic field. Trajectory of the massage objects may be random, circular, linear and/or massage objects may rotate around one or more axes, and/or may do other types of moves in the gap volume.

The massage unit may also comprise a membrane on the side facing the patient which may be accelerated by an electric, magnetic, electromagnetic field or by changing pressure value in the gap volume between wall of the chamber and the membrane. This membrane may act as the massage object.

During the treatment, it may be convenient to use a combination of pads with adhesive layer and pads with suction openings. In that case at least one pad used during the treatment may comprise adhesive layer and at least additional one pad used during the treatment may comprise suction opening. For example, pad with adhesive layer may be suited for treatment of more uneven areas, e.g. periorbital area, and pad with suction openings for treatment of smoother areas, e.g. cheeks.

The advantage of the device where the attachment od the pads may be provided by adhesion layer or by suction opening or their combination is that there is no need of any additional gripping system which would be necessary to hold the pads on the treatment area during the treatment, e.g. a band or a felt, which may cause a discomfort of the patient.

Yet in another embodiment, it is possible to fasten the flexible pads 4 to the face by at least one band or felt which may be made from an elastic material and thus adjusted for an individual face. In that case the flexible pads, which may have not the adhesive layer or suction opening, are placed on the treatment area of the patient and their position is then fastened by a band or felt to avoid deflection of the pads from the treatment areas. Alternatively, the band may be replaced by an elastic mask that covers from 5% to 100% or from 30% to 99% or from 40% to 95% or from 50% to 90% of the face and may serve to secure the flexible pads on the treatment areas. Furthermore, it may be possible to use the combination of the pad with adhesive layer or suction opening and the fastening band, felt or mask to ensure strong attachment of the pads on the treatment areas.

Additionally, the fastening mechanism may be in the form of a textile or a garment which may be mountable on a user's body part. In use of the device, a surface of the electrode or electrode pad 4 lays along an inner surface of the garment, while the opposite surface of the electrode or electrode pad 4 is in contact with the user's skin, preferably by means of a skin-electrode hydrogel interface.

The garment may be fastened for securement of the garment to or around a user's body part, e.g. by hook and loop fastener, button, buckle, stud, leash or cord, magnetic-guided locking system or clamping band and the garment may be manufactured with flexible materials or fabrics that adapt to the shape of the user's body or limb. The electrode pad 4 may be in the same way configured to be fastened to the inner surface of the garment. The garment is preferably made of breathable materials. Non limiting examples of such materials are soft Neoprene, Nylon, polyurethane, polyester, polyamide, polypropylene, silicone, cotton or any other material which is soft and flexible. All named materials could be used as woven, non-woven, single use fabric or laminated structures.

The garment and the pad may be modular system, which means module or element of the device (pad, garment) and/or system is designed separately and independently from the rest of the modules or elements, at the same time that they are compatible with each other.

The pad 4 may be designed to be attached to or in contact with the garment, thus being carried by the garment in a stationary or fixed condition, in such a way that the pads are disposed on fixed positions of the garment. The garment ensures the correct adhesion or disposition of the pad to the user's skin. In use of the device, the surface of one or more active elements not in contact with the garment is in contact with the patient's skin, preferably by means of a hydrogel layer that acts as pad-skin interface. Therefore, the active elements included in the pad are in contact with the patient's skin.

The optimal placement of the pad on the patient's body part, and therefore the garment which carries the pad having the active elements, is determined by a technician or clinician helping the patient.

In addition, the garment may comprise more than one pad or the patient may wear more than one garment comprising one or more pads during one treatment session.

The pad 4 may contain at least one active element 13 capable of delivering energy from primary electromagnetic generator 6 or secondary generator 9 or ultrasound emitter 10. The active element may be in the form of an electrode, an optical element, an acoustic window, an ultrasound emitter or other energy delivering elements known in the art. The electrode may be a radiofrequency (RF) electrode. The RF electrode may be a dielectric electrode coated with insulating (e.g. dielectric) material. The RF electrode may be monopolar, bipolar, unipolar or multipolar. The bipolar arrangement may consist of electrodes that alternate between active and return function and where the thermal gradient beneath electrodes is almost the same during treatment. Bipolar electrodes may form circular or ellipsoidal shapes, where electrodes are concentric to each other. However, a group of bipolar electrode systems may be used as well. A unipolar electrode or one or more multipolar electrodes may be used as well. The system may alternatively use monopolar electrodes, where the so called return electrode has larger area than so called active electrode. The thermal gradient beneath the active electrode is therefore higher than beneath the return electrode. The active electrode may be part of the pad and the passive electrode having larger surface area may be located at least 5 cm, 10 cm, or 20 cm from the pad. A neutral electrode may be used as the passive electrode. The neutral electrode may be on the opposite side of the patient's body than the pad is attached. A unipolar electrode may also optionally be used. During unipolar energy delivery there is one electrode, no neutral electrode, and a large field of RF emitted in an omnidirectional field around a single electrode. Capacitive and/or resistive electrodes may be used. Radiofrequency energy may provide energy flux on the surface of the active element 13 or on the surface of the treated tissue (e.g. skin) in the range of 0.001 W/cm$^2$ to 1500 W/cm$^2$ or 0.01 W/cm$^2$ to 1000 W/cm$^2$ or 0.5 W/cm$^2$ to 500 W/cm$^2$ or 0.5 W/cm$^2$ to 100 W/cm$^2$ or 1 W/cm$^2$ to 50 W/cm$^2$. The energy flux on the surface of the active element 13 may be calculated from the size of the active element 13 and its output value of the energy. The energy flux on the surface of the treated tissue may be calculated from the size of the treated tissue exactly below the active element 13 and its input value of the energy provided by the active element 13. In addition, the RF electrode positioned in the pad 4 may act as an acoustic window for ultrasound energy.

The active element 13 may provide a secondary energy from secondary generator 9 in form of an electric current or a magnetic field. By applying the secondary energy to the treated area of the body of the patient, muscle fibers stimulation may be achieved and thus increasing muscle tone, muscle strengthening, restoration of feeling the muscle, relaxation of the musculature and/or stretching musculature.

The proposed device may provide an electrotherapy in case that the secondary energy delivered by the active element 13 (e.g a radiofrequency electrode or simply referred just as an electrode) is the electric current. The main effects of electrotherapy are: analgesic, myorelaxation, iontophoresis, anti-edematous effect or muscle stimulation causing a muscle fiber contraction. Each of these effects may be achieved by one or more types of electrotherapy: galvanic current, pulse direct current and alternating current.

Galvanic current (or "continuous") is a current that may have constant electric current and/or absolute value of the electric current is in every moment higher than 0. It may be used mostly for iontophoresis, or its trophic stimulation (hyperemic) effect is utilized. At the present invention this current may be often substituted by galvanic intermittent current. Additionally, galvanic component may be about 95% but due to interruption of the originally continuous intensity the frequency may reach 5-12 kHz or 5-10 kHz or 5-9 kHz or 5-8 kHz.

The pulse direct current (DC) is of variable intensity but only one polarity. The basic pulse shape may vary. It includes e.g. diadynamics, rectangular, triangular and exponential pulse of one polarity. Depending on the used frequency and intensity it may have stimulatory, tropic, analgesic, myorelaxation, iontophoresis, at least partial muscle contraction and anti-edematous effect and/or other.

Alternating Current (AC or biphasic) where the basic pulse shape may vary—rectangular, triangular, harmonic sinusoidal, exponential and/or other shapes and/or combination of mentioned above. It can be alternating, symmetric and/or asymmetric. Use of alternating currents in contact electrotherapy implies much lower stress on the tissue under the electrode. For these types of currents the capacitive component of skin resistance is involved, and due to that these currents are very well tolerated by the patients.

AC therapies may be differentiate to five subtypes: TENS, Classic (four-pole) Interference, Two-pole Interference, Isoplanar Interference and Dipole Vector Field. It also exist some specific electrotherapy energy variants and modularity of period, shape of the energy etc.

Due to interferential electrotherapy, different nerves and tissue structures by medium frequency may be stimulated in a range of 500 Hz to 12 kHz or in a range of 500 Hz to 8 kHz, or 500 Hz to 6 kHz, creating pulse envelopes with frequencies for stimulation of the nerves and tissues e.g. sympathetic nerves (0.1-5 Hz), parasympathetic nerves (10-150 Hz), motor nerves (10-50 Hz), smooth muscle (0.1-10 Hz), sensor nerves (90-100 Hz) nociceptive fibres (90-150 Hz).

Electrotherapy may provide stimulus with currents of frequency in the range from 0.1 Hz to 12 kHz or in the range from 0.1 Hz to 8 kHz or in the range from 0.1 Hz to 6 kHz.

Muscle fiber stimulation by electrotherapy may be important during and/or as a part of the RF treatment. Muscle stimulation increases blood flow and lymph circulation. It may improve removing of treated cells and/or prevent of hot spots creation. Moreover internal massage stimulation of adjoining tissues improves homogeneity of tissue and dispersing of the delivered energy. The muscle fiber stimulation by electrotherapy may cause muscle contractions, which may lead to improvement of a visual appearance of the patient through muscle firming and strengthening, Another beneficial effect is for example during fat removing with the RF therapy. RF therapy may change structure of the fat tissue. The muscle fiber stimulation may provide internal massage, which may be for obese patient more effective than classical massage.

Muscle stimulation may be provided by e.g. intermittent direct currents, alternating currents (medium-frequency and TENS currents), faradic current as a method for multiple stimulation and/or others.

Frequency of the currents may be in the range from 0.1 Hz to 1500 Hz or from 0.1 to 1000 Hz or from 0.1 Hz to 500 Hz or from 0.1 to 300 Hz.

Frequency of the current envelope is typically in the range from 0.1 Hz to 500 Hz or from 0.1 Hz to 250 Hz or from 0.1 Hz to 150 Hz or from 0.1 Hz to 140 Hz.

The electrostimulation may be provided in a combined manner where various treatments with various effects may be achieved. As an illustrative example, the electromagnetic energy with the electrostimulation may be dosed in trains of pulses of electric current where the first train of electrostimulation may achieve different effect than second or other successive train of stimulation. Therefore, the treatment may provide muscle fibers stimulation or muscle contractions followed by relaxation, during continual or pulsed radiofrequency thermal heating provided by electromagnetic energy provided by electromagnetic energy generator.

The electrostimulation may be provided by monopolar, unipolar, bipolar or multipolar mode.

Absolute value of voltage between the electrotherapy electrodes operated in bipolar, multipolar mode (electric current flow between more than two electrodes) and/or provided to at least one electrotherapy electrode may be in range between 0.8 V and 10 kV; or in range between 1 V and 1 kV; or in range between 1 V and 300 V or in range between 1 V and 100 V.

Current density of electrotherapy for non-galvanic current may be in range between 0.1 mA/cm$^2$ and 150 mA/cm$^2$, or in range between 0.1 mA/cm$^2$ and 100 mA/cm$^2$, or in range between 0.1 mA/cm$^2$ and 50 mA/cm$^2$, or in range between 0.1 mA/cm$^2$ and 20 mA/cm$^2$; for galvanic current may be preferably in range between 0.05 mA/cm$^2$ and 3 mA/cm$^2$, or in range between 0.1 mA/cm$^2$ and 1 mA/cm$^2$, or in range between 0.01 mA/cm$^2$ and 0.5 mA/cm$^2$. The current density may be calculated on the surface of the electrode providing the electrotherapy to the patient.

During electrotherapy, e.g. bipolar electrotherapy, two or more electrodes may be used. If polarity of at least one electrode has a non-zero value in a group of the electrodes during bipolar mode, the group of the electrodes has to include at least one electrode with opposite polarity value. Absolute values of both electrode polarities may or may not be equal. In bipolar electrostimulation mode stimulating signal passes through the tissue between electrodes with opposite polarities.

Distance between two electrodes operating in bipolar mode may be in range between 0.1 mm and 4 cm or in range between 0.2 mm to 3 cm or in range between 0.5 mm and 2 cm or in range between 1 mm and 1 cm or in the range of 0.1 cm and 40 cm or in range between 1 cm and 30 cm, or in the range between 1 cm and 20 cm.

During monopolar electrotherapy mode stimulating signal may be induced by excitement of action potential by changing polarity of one electrode that change polarization in the nerve fiber and/or neuromuscular plague.

During the electrotherapy, one of the bipolar or monopolar electrotherapy mode may be used or bipolar or monopolar electrotherapy mode may be combined.

The ultrasound emitters may provide focused or defocused ultrasound energy. The ultrasound energy may be transferred to the tissue through an acoustic window. The output power of the ultrasound energy on the surface of the active element 13 may be less than or equal to 20 W or 15 W or 10 W or 5 W. Ultrasound energy may provide energy flux on the surface of the active element 13 or on the surface of the treated tissue (e.g. skin) in the range of 0.001 W/cm$^2$ to 250 W/cm$^2$, or in the range of 0.005 W/cm$^2$ to 50 W/cm$^2$, or in the range of 0.01 W/cm$^2$ to 25 W/cm$^2$, or in the range of 0.05 W/cm$^2$ to 20 W/cm$^2$. The treatment depth of ultrasound energy may be in the range of 0.1 mm to 100 mm or 0.2 mm to 50 mm or 0.25 mm to 25 mm or 0.3 mm to 15 mm. At a depth of 5 mm the ultrasound energy may provide an energy flux in the range of 0.01 W/cm$^2$ to 20 W/cm$^2$ or 0.05 W/cm$^2$ to 15 W/cm$^2$. An ultrasound beam may have a beam non-uniformity ratio (RBN) in the range of 0.1 to 20 or 2 to 15 to 4 to 10. In addition, an ultrasound beam may have a beam non-uniformity ratio below 15 or below 10. An ultrasound beam may be divergent, convergent and/or collimated. The ultrasound energy may be transferred to the tissue through an acoustic window. It is possible that the RF electrode may act as the acoustic window. Furthermore, the ultrasound emitter 10 may be a part of the active element 13, thus ultrasound emitter 10 may be a part of the pad 4.

At least some of the active elements 13 may be capable of delivering energy from primary electromagnetic generator 6 or secondary generator 9 or ultrasound emitter 10 simultaneously (at the same time) successively or in an overlapping method or in any combination thereof. For example, the active element 13 may be capable of delivering radiofrequency energy and electric current sequentially, which may mean that firstly the active element 13 may provide primary electromagnetic energy generated by the primary electromagnetic generator 6 and subsequently the active element 13 may provide the secondary energy generated by the secondary generator 9. Thus the active element 13 may e.g. apply radiofrequency energy to the tissue of the patient and then the same active element 13 may apply e.g. electrical current to the tissue of the patient.

Pad 4 may further comprise thermal sensors 15 enabling temperature control during the therapy, providing feedback to CPU 11, enabling adjustment of treatment parameters of each active element and providing information to the operator. The thermal sensor 15 may be a contact sensor, contactless sensor (e.g. infrared temperature sensor) or invasive sensor (e.g. a thermocouple) for precise temperature measurement of deep layers of skin, e.g. epidermis, dermis or hypodermis. The CPU 11 may also use algorithms to calculate the deep or upper-most temperatures. A temperature feedback system may control the temperature and based on set or pre-set limits alert the operator in human perceptible form, e.g. on the human machine interface 8 or via indicators 17. In a limit temperature condition, the device may be configured to adjust one or more treatment parameters, e.g. output power, switching mode, pulse length, etc. or stop the treatment. A human perceptible alert may be a sound, alert message shown on human machine interface 8 or indicators 17 or change of color of any part of the interconnecting block 3 or pad 4.

Memory 12 may include, for example, information about the type and shape of the pad 4, its remaining lifetime, or the time of therapy that has already been performed with the pad.

Neutral electrode 7 may ensure proper radiofrequency distribution within the patient's body for mono-polar radiofrequency systems. The neutral electrode 7 is attached to the patient's skin prior to each therapy so that the energy may be distributed between active element 13 and neutral electrode 7. In some bipolar or multipolar radiofrequency systems, there is no need to use a neutral electrode—radiofrequency energy is distributed between multiple active elements 13. Neutral electrode 7 represents an optional block of the apparatus 1 as any type of radiofrequency system can be integrated.

Additionally, device 1 may include one or more sensors. The sensor may provide information about at least one physical quantity and its measurement may lead to feedback which may be displayed by human machine interface 8 or indicators 17. The one or more sensors may be used for sensing delivered electromagnetic energy, impedance of the skin, resistance of the skin, temperature of the treated skin, temperature of the untreated skin, temperature of at least one layer of the skin, water content of the device, the phase angle of delivered or reflected energy, the position of the active elements 13, the position of the interconnecting block 3, temperature of the cooling media, temperature of the primary electromagnetic generator 6 and secondary generator 9 and ultrasound emitter 10 or contact with the skin. The sensor may be a thermal, acoustic, vibration, electric, magnetic, flow, positional, optical, imaging, pressure, force, energy flux, impedance, current, Hall or proximity sensor. The sensor may be a capacitive displacement sensor, acoustic proximity sensor, gyroscope, accelerometer, magnetometer, infrared camera or thermographic camera. The sensor may be invasive or contactless. The sensor may be located on or in the pad 4, in the main unit 2, in the interconnecting block 3 or may be a part of a thermal sensor 15. One sensor may measure more than one physical quantity. For example, the sensor may include a combination of a gyroscope, an accelerometer and/or a magnetometer. Additionally, the sensor may measure one or more physical quantities of the treated skin or untreated skin.

A resistance sensor may measure skin resistance, because skin resistance may vary for different patients, as well as the humidity—wetness and sweat may influence the resistance and therefore the behavior of the skin in the energy field. Based on the measured skin resistance, the skin impedance may also be calculated.

Information from one or more sensors may be used for generation of a pathway on a model e.g. a model of the human body shown on a display of human machine interface 8. The pathway may illustrate a surface or volume of already treated tissue, presently treated tissue, tissue to be treated, or untreated tissue. A model may show a temperature map of the treated tissue providing information about the already treated tissue or untreated tissue.

The sensor may provide information about the location of bones, inflamed tissue or joints. Such types of tissue may not be targeted by electromagnetic energy due to the possibility of painful treatment. Bones, joints or inflamed tissue may be detected by any type of sensor such as an imaging sensor (ultrasound sensor, IR sensor), impedance sensor, and the like. A detected presence of these tissue types may cause general human perceptible signals or interruption of generation of electromagnetic energy. Bones may be detected by a change of impedance of the tissue or by analysis of reflected electromagnetic energy.

The patient's skin over at least one treatment portion may be pre-cooled to a selected temperature for a selected duration, the selected temperature and duration for pre-cooling may be sufficient to cool the skin to at least a selected temperature below normal body temperature. The skin may be cooled to at least the selected temperature to a depth below the at least one depth for the treatment portions so that the at least one treatment portion is substantially surrounded by cooled skin. The cooling may continue during the application of energy, and the duration of the application of energy may be greater than the thermal relaxation time of the treatment portions. Cooling may be provided by any known mechanism including water cooling, sprayed coolant, presence of an active solid cooling element (e.g. thermoelectric cooler) or air flow cooling. A cooling element may act as an optical element. Alternatively, the cooling element may be a spacer. Cooling may be provided during, before or after the treatment with electromagnetic energy. Cooling before treatment may also provide an environment for sudden heat shock, while cooling after treatment may provide faster regeneration after heat shock. The temperature of the coolant may be in the range of −200° C. to 36° C. The temperature of the cooling element during the treatment may be in the range of −80° C. to 36° C. or −70° C. to 35° C. or −60° C. to 34° C. Further, where the pad is not in contact with the patient's skin, cryogenic spray cooling, gas flow or other non-contact cooling techniques may be utilized. A cooling gel on the skin surface might also be utilized, either in addition to or instead of, one of the cooling techniques indicated above.

Figure 3A:
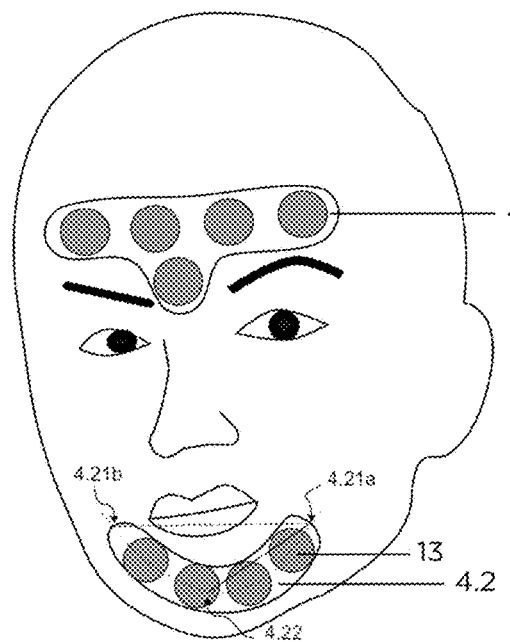
FIG. 3A represents pad shapes and layout.
Figure 3B:
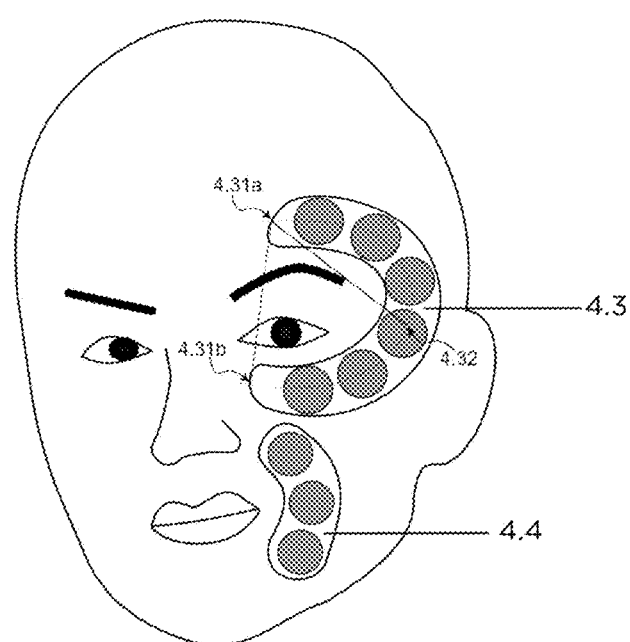
FIG. 3B represents pad shapes and layout.

FIG. 3A and FIG. 3B show different shapes and layouts of pad 4 used by an apparatus for contact therapy. Pads 4 comprise at least one active element 13 and may be available in various shapes and layouts so that they may cover a variety of different treatment areas and accommodate individual patient needs, e.g. annular, semicircular, elliptical, oblong, square, rectangular, trapezoidal, polygonal or formless (having no regular form or shape). The shapes and layouts of the pad 4 may be shaped to cover at least part of one or more of the periorbital area, the forehead (including frown lines), the jaw line, the perioral area (including Marionette lines, perioral lines—so called smoker lines, nasolabial folds, lips and chin), cheeks or submentum, etc. The shape of the pad 4 and distribution, size and number of active elements 13 may differ depending on the area being treated, e.g. active elements 13 inside the pad 4 may be in one line, two lines, three lines, four lines or multiple lines. The pad 4 with active elements 13 may be arranged into various shapes, e.g. in a line, where the centers of at least two active elements 13 lie in one straight line, while any additional center of an active element 13 may lie in the same or different lines inside the pad 4.

In addition, the pad 4 may be used to treat at least partially neck, bra fat, love handles, torso, back, abdomen, buttocks, thighs, calves, legs, arms, forearms, hands, fingers or body cavities (e.g. vagina, anus, mouth, inner ear etc.).

The pad 4 may have a rectangular, oblong, square, trapezoidal form, or of the form of a convex or concave polygon wherein the pad 4 may have at least two different inner angles of the convex or concave polygon structure. Additionally, the pad 4 may form at least in part the shape of a conic section (also called conic), e.g. circle, ellipse, parabola or hyperbola. The pad 4 may have at least in part one, two, three, four, five or more curvatures of a shape of an arc with the curvature k in the range of 0.002 to 10 $mm^{-1}$ or in the range of 0.004 to 5 $mm^{-1}$ or in the range of 0.005 to 3 $mm^{-1}$ or in the range of 0.006 to 2 $mm^{-1}$. The pad 4 may have at least one, two, three, four, five or more arcs with the curvature k or may have at least two different inner angles of a convex or concave polygon structure, and may be suitable for the treatment of chin, cheeks, submental area (e.g. "banana shape 1" 4.2), for treating jaw line, perioral area, Marionette lines and nasolabial folds (e.g. "banana shape 2" 4.4), for the treatment of periorbital area (e.g. "horseshoe shape" 4.3) or other regions of face and neck.

The "banana shape" pad 4.2 or 4.4 may have a convex-concave shape, which means that one side is convex and the opposite side is concave, that occupies at least 5% to 50% or 10% to 60% or 15% to 70% or 20% to 90% of a total circumference of the pad 4 seen from above, wherein the shortest distance between the endpoints 4.21a and 4.21b of the "banana shape" pad 4.2 (dashed line in FIG. 3A) is longer than the shortest distance between the endpoint 4.21a or 4.21b and the middle point 4.22 of the "banana shape" (full line in pad 4.2 in FIG. 3A). The "horseshoe shape" 4.3 seen from above may have the convex-concave shape that occupies at least 15% to 50% or 20% to 60% or 25% to 70% or 30% to 90% of its total circumference, wherein the shortest distance between the endpoints 4.31a and 4.31b of the "horseshoe shape" pad 4.3 (dashed line in FIG. 3B) is equal or shorter than the shortest distance between the endpoint 4.31a or 4.31b and the middle point 4.32 of the "horseshoe shape" (full line in pad 4.3 in FIG. 3B). When seen from above, if the longest possible center curve, which may be convex or concave and whose perpendiculars at a given point have equidistant distance from perimeter edges of the pad at each of its points (dotted line in pad 4.2 in FIG. 3A), intersects the circumference of the pad 4 then this point is the endpoint of the pad, e.g. endpoint 4.21a or 4.21b. The middle point, e.g. 4.22, is then given as the middle of the center curve, wherein the total length of the center curve is given by two endpoints, e.g. 4.21a and 4.21b, thus the length of the center curve (dotted line in pad 4.2 in FIG. 3A) from point 4.21a to point 4.22 is the same as the length from point 4.21b to point 4.22. The total length of the center curve may be in the range of 0.1 to 30 cm or in the range of 0.5 to 25 cm or in the range of 1 to 20 cm.

In addition, the center curve may have at least in part circular, elliptical, parabolic, hyperbolic, exponential, convex or concave curve such that the straight line connecting endpoint of the pad 4 with the middle point of the center curve forms an angle alpha with the tangent of the middle of the center curve. The angle alpha may be in a range of 0.1° to 179° or in a range of 0.2° to 170° or in a range of 0.5° to 160° or in a range of 1° to 150°.

The pad 4 whose shape has at least two concave arcs with the curvature k or has at least two concave inner angles of the polygon structure may be suitable for the treatment of the forehead like the "T shape" 4.1 in FIG. 3A. The "T shape" 4.1 may be also characterized by the arrangement of the active elements 13 where the centers of at least two active elements 13 lie in one straight line and center of at least one additional element 13 lies in a different line.

Pads may have different sizes with the surface areas ranging from 0.1 to 150 $cm^2$ or from 0.2 to 125 $cm^2$ or from 0.5 to 100 $cm^2$ or in the range of 1 to 50 $cm^2$. The pad may occupy approximately 1 to 99% or 1 to 80% or 1 to 60% or 1 to 50% of the face. The number of active elements 13 within a single pad 4 ranges from 1 to 100 or from 1 to 80 or from 1 to 60 or from 1 to 40. A thickness at least in a part of the pad 4 may be in the range of 0.01 to 15 cm or in the range of 0.02 to 10 cm or in the range of 0.05 to 7 cm or in the range of 0.1 to 7 cm.

Furthermore the pads 4 may have a shape that at least partially replicates the shape of galea aponeurotica, procerus, levatar labii superioris alaeque nasi, nasalis, lavator labii superioris, zygomaticus minor, zygomaticus major, levator anguli oris, risorius, platysma, depressor anguli oris, depressor labii inferioris, occipitofrontalis (frontal belly), currugator supercilii, orbicularis oculi, buccinator, masseter, orbicularis oris or mentalis muscle when the pad 4 is attached to the surface of the patient skin.

The pad 4 may be characterized by at least one aforementioned aspect or by a combination of more than one aforementioned aspect or by a combination of all aforementioned aspects.

The electromagnetic energy generator 6 or the secondary generator 9 inside the main case may generate an electromagnetic or secondary energy (e.g. electric current) which may be delivered via a conductive lead to at least one active element 13 attached to the skin, respectively. The active element 13 may deliver energy through its entire surface or by means of a so-called fractional arrangement. Active element 13 may comprise an active electrode in a monopolar, unipolar, bipolar or multipolar radiofrequency system. In the monopolar radiofrequency system, energy is delivered between an active electrode (active element 13) and a neutral electrode 7 with a much larger surface area. Due to mutual distance and difference between the surface area of the active and neutral electrode, energy is concentrated under the active electrode enabling it to heat the treated area. In the unipolar, bipolar or multipolar radiofrequency system, there is no need for neutral electrode 7. In the bipolar and multipolar radiofrequency system, energy is delivered between two and multiple active electrodes with similar surface area, respectively. The distance between these electrodes determines the depth of energy penetration. In the unipolar radiofrequency system, only a single active electrode is incorporated and energy is delivered to the tissue and environment surrounding the active electrode. The distance between the two nearest active elements 13 (e.g. the nearest neighboring sides of electrodes) in one pad 4 may be in the range of 0.1 to 100 mm or in the range of 0.3 to 70 mm or in the range of 0.5 to 60 mm or in the range of 1 to 50 mm.

Figure 4:
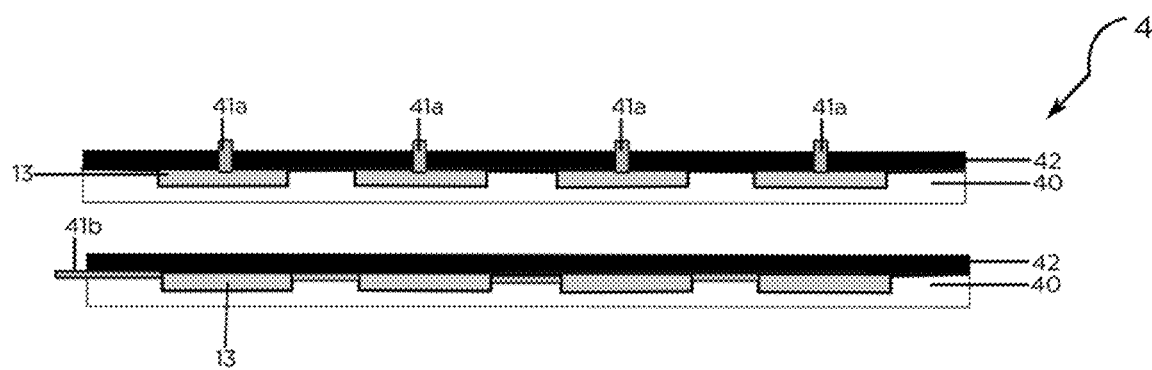
FIG. 4 represents a side view of the pad intended for contact therapy.

FIG. 4 represents a side view of the pad 4 configured for contact therapy. Pads 4 may be made of flexible substrate material 42—polyimide (PI) films, teflon, epoxy or PE foam with an additional adhesive layer 40 on the underside. They may be of different shapes to allow the operator to choose according to the area to be treated. Active elements 13 may have a circumference of annular, semicircular, elliptical, oblong, square, rectangular, trapezoidal or polygonal shape with a surface area in the range from 0.1 to 70 cm$^2$ or from 0.5 to 50 cm$^2$ or from 1 to 25 cm$^2$ or from 1 to 10 cm$^2$. The material used may be copper, aluminum, lead or any other conductive medium that can be deposited or integrated in the pad. Furthermore the active elements 13 (e.g. electrodes) may be made of silver, gold or graphite. Electrodes 13 in the pad 4 may be printed by means of biocompatible ink, such as silver ink, graphite ink or a combination of inks of different conductive materials.

The active element 13 (e.g. electrode providing radiofrequency field and/or electric field) may be full-area electrode that has a full active surface. This means that the whole surface of the electrode facing the patient may be made of conductive material deposited or integrated in the pad 4 as mentioned above.

Figure 8A:
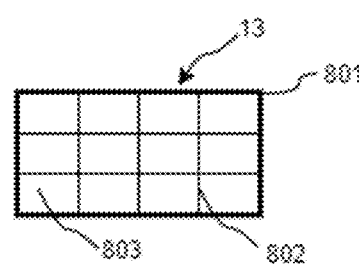
FIG. 8A is an illustration of the framed grated electrode.
Figure 8B:
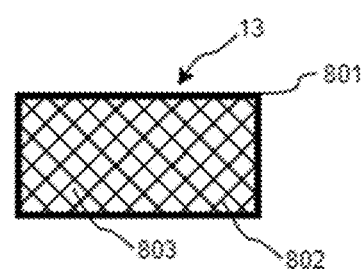
FIG. 8B is an illustration of another framed grated electrode.
Figures 8C, 8D:
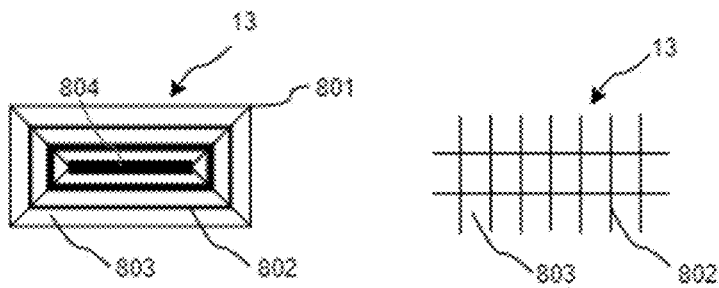
FIG. 8C is an illustration of framed grated electrode with thinning conductive lines.
FIG. 8D is an illustration of non-framed grated electrode.

Alternatively, the surface of the electrode 13 facing the patient may be formed by the combination of the conductive (e.g. copper) and non-conductive material (for example dielectric material, insulation material, substrate of the pad, air or hydrogel). The electrode 13 may be framed by the conductive material and the inside of the frame may have a combination of conductive and non-conductive material. The frame may create the utmost circumference of the electrode from the side facing the patient. The frame may have a form of annular, semicircular, elliptical, oblong, square, rectangular, trapezoidal or polygonal shape. The inside of the frame 801 may have a structure of a grid 802 as shown in FIGS. 8A and 8B with the non-conductive part 803. The frame 801 may be of the same thickness as the thickness of the grid lines 802 or the thickness of the frame 801 may be thicker than the grid lines 802 in the range of 1% to 2000% or in the range of 10% to 1000% or in the range of 20% to 500% or in the range of 50% to 200%. Additionally the frame 801 may be thinner than the grid lines 802 in the range of 0.01 times to 20 times or in the range of 0.1 times to 10 times or in the range of 0.2 times to 5 times or in the range of 0.5 times to 2 times. It may be also possible to design the electrode such that the conductive material of the electrode is getting thinner from the center 804 of the electrode 13 as shown in FIG. 8C. The thinning step between adjacent grid lines 802 in the direction from the center 804 may be in the range of 0.1 times to 10 times or in the range of 0.2 times to 5 times or in the range of 0.5 times to 2 times with the frame 801 having the thinnest line of conductive material. Alternatively, the electrode may not be framed, e.g. it may have a form of a grid with no boundaries as shown in FIG. 8D. A ratio of conductive to non-conductive material of the electrode may be in the range of 1% to 99%, or in the range of 5% to 95% or in the range of 10% to 90% or in the range of 20% to 80% or in the range of 30% to 70% or in the range of 40% to 60%. Additionally the ration of conductive to non-conductive material of the electrode may be in the range of 1% to 20%, or in the range of 10% to 40% or in the range of 33% to 67% or in the range of 50% to 70% or in the range of 66% to 100%. Such a grated electrode may be very advantageous. It may be much more flexible, it may ensure contact with the patient that is more proper and it may have much better self-cooling properties than full-area electrode.

In case when the active element 13 is in the form of the grated electrode, the energy flux of the grated electrode may be calculated as an energy flux of the grid 802 and/or the frame 801 of the active element 13 and may be in the range of 0.001 W/cm$^2$ to 1500 W/cm$^2$ or 0.01 W/cm$^2$ to 1000 W/cm$^2$ or 0.5 W/cm$^2$ to 500 W/cm$^2$.

The active elements 13 may be partially embedded within the flexible substrate layer 42 or adhesive layer 40 or in the interface of the flexible substrate layer 42 and adhesive layer 40. The active elements 13 may be supplied and controlled independently by multiple conductive leads 41a or they may be conductively interconnected and supplied/controlled via a single conductive lead 41b. The multiple conductive leads 41a may be connected to the active elements 13 via a free space (e.g. hole) in the flexible substrate layer 42. The free space (e.g. hole) may have such dimensions that each conductive lead 41a may fit tightly into the substrate layer 42, e.g. the conductive lead 41a may be encapsulated by flexible substrate layer 42. In case of a single conductive lead connection, the active elements 13 may be partially embedded inside the flexible substrate 42 or adhesive layer 40 or in the interface of the flexible substrate layer 42 and adhesive layer 40, and the active elements 13 may be connected via single conductive lead 41b which may be situated in the flexible substrate 42 or at the interface of the flexible substrate 42 and adhesive layer 40. The single conductive lead 41b may leave the pad 4 on its lateral or top side in a direction away from the patient. In both cases the conductive lead 41a or 41b does not come into contact with the treatment area.

Additionally, the active elements 13 may be partially embedded within the flexible substrate 42 and the adhesive layer 40 may surround the active elements 13 such that a surface of active elements 13 may be at least partially in direct contact with the surface of a treatment area.

Total pad thickness in the narrower spot may be in the range of 0.1 mm to 60 mm or in the range of 0.5 mm to 50 mm or in the range of 0.7 mm to 40 mm or in the range of 1 mm to 30 mm.

The apparatus configured in a fractional arrangement may have the active element 13 comprising a matrix formed by active points of defined size. These points are separated by inactive (and therefore untreated) areas that allow faster tissue healing. The surface containing active points may make up from 1 to 99% or from 2 to 90% or from 3 to 80% or from 4 to 75% of the whole active element area. The active points may have blunt ends at the tissue contact side that do not penetrate the tissue, wherein the surface contacting tissue may have a surface area in the range of 500 $\mu m^2$ to 250 000 $\mu m^2$ or in the range of 1000 $\mu m^2$ to 200 000 $\mu m^2$ or in the range of 200 $\mu m^2$ to 180 000 $\mu m^2$ or in the range of 5000 $\mu m^2$ to 160 000 $\mu m^2$. The blunt end may have a radius of curvature of at least 0.05 mm. A diameter of the surface contacting tissue of one active point may be in the range of 25 $\mu m$ to 1500 $\mu m$ or in the range of 50 $\mu m$ to 1000 $\mu m$ or in the range of 80 $\mu m$ to 800 $\mu m$ or in the range of 100 $\mu m$ to 600 $\mu m$.

Additionally, the device may employ a safety system comprising thermal sensors and a circuit capable of adjusting the therapy parameters based on the measured values. One or more thermal sensors, depending on the number and distribution of active elements 13, may be integrated onto pad 4 to collect data from different points so as to ensure homogeneity of heating. The data may be collected directly from the treatment area or from the active elements 13. If uneven heating or overheating is detected, the device may notify the operator and at the same time adjust the therapy parameters to avoid burns to the patient. Treatment parameters of one or more active elements might be adjusted. The main therapy parameters are power, duty cycle and time period regulating switching between multiple active elements 13. Therapy may be automatically stopped if the temperature rises above the safe threshold.

Furthermore, impedance measurement may be incorporated in order to monitor proper active element 13 to skin contact. If the impedance value is outside the allowed limits, the therapy may be automatically suspended and the operator may be informed about potential contact issues.

CPU 11 may be incorporated onto the pad 4 itself or it may form a separate part conductively connected to the pad 4. In addition to the control mechanism, CPU 11 may also contain main indicators (e.g. ongoing therapy, actual temperature and active element to skin contact).

Figure 5:
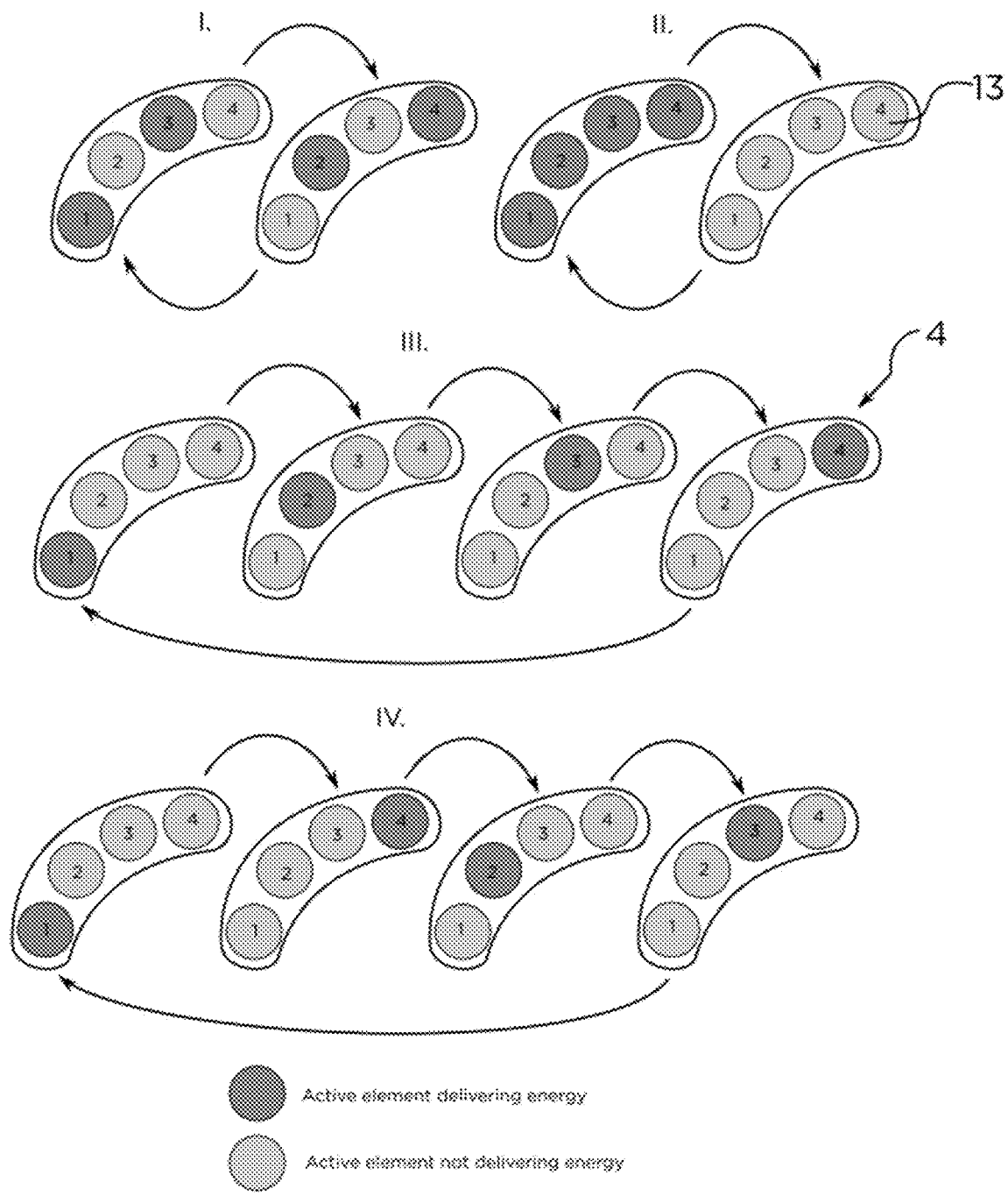
FIG. 5 shows one variant of energy delivery by switching multiple active elements.

FIG. 5 shows some delivery approaches of apparatus for contact therapy.

It is possible to switch between multiple active elements 13 within the single pad 4 in such a way so that the multiple active elements 13 deliver energy simultaneously, successively or in an overlapping method or any combination thereof. For example, in the case of two active elements: in the simultaneous method, both active elements are used simultaneously during the time interval e.g., 1-20 s. In the successive method, the first active element is used during the first time interval e.g., from 1 s to 10 s. The first active element is then stopped and the second active element is immediately used in a subsequent time interval e.g., from 10 s to 20 s. This successive step may be repeated. In the overlapping method, the first active element is used during a time interval for e.g., 1-10 s, and the second active element is used in a second overlapping time interval for e.g., 1-10 s, wherein during the second time interval the first active element and the second active element are overlapping e.g., with total overlapping method time of 0.1-9.9 s. Active elements 13 may deliver energy sequentially in predefined switching order or randomly as set by operator via human machine interface 8. Schema I in FIG. 5 represents switching between pairs/groups formed of non-adjacent active elements 13 located within a pad 4. Every pair/group of active elements 13 is delivering energy for a predefined period of time (dark gray elements in FIG. 5—in schema I elements 1 and 3) while the remaining pairs/groups of active elements 13 remain inactive in terms of energy delivery (light gray elements in FIG. 5—in schema I elements 2 and 4). After a predefined period of time, energy is delivered by another pair/group of active elements 13 and the initial active elements become inactive. This is indicated by arrows in FIG. 5. Switching between pairs/groups of active elements 13 may continue until a target temperature is reached throughout the entire treatment area or a predefined energy is delivered by all active elements 13. Schema II in FIG. 5 represents switching of all active elements 13 within the pad 4 between state ON when active elements are delivering energy and OFF when they are not delivering energy. The duration of ON and OFF states may vary depending on predefined settings and/or information provided by sensors, e.g. thermal sensors. Schema III in FIG. 5 shows sequential switching of individual active elements 13 within a pad 4. Each active element 13 is delivering energy for predefined periods of time until a target temperature is reached throughout the entire treatment area or a predefined energy is delivered by all active elements 13. This sequential switching may be executed in a clockwise or anticlockwise order. Schema IV in FIG. 5 represents a zig-zag switching order during which preferably non-adjacent active elements 13 deliver energy sequentially until all active elements 13 within a pad 4 have been switched ON. Each active element 13 delivers energy for a predefined period of time until a target temperature is reached throughout the entire treatment area or a predefined energy is delivered by all active elements.

The CPU may be configured to control the stimulation device and provide treatment by at least one treatment protocol improving of visual appearance. Treatment protocol is set of parameters of the primary electromagnetic energy and the secondary energy ensuring the desired treatment effect. Each pad may be controlled to provide same or alternatively different protocol. Pair areas or areas where symmetrical effect is desired may be treated by the same treatment protocol. Each protocol may include one or several sections or steps.

As a non-limiting example: in case of applying the radiofrequency energy by the active elements one by one as shown in Schema III and IV in FIG. 5, the time when one active element delivers the radiofrequency energy to the tissue of the patient may be in the range of 1 ms to 10 s or in the range of 10 ms to 5 s or in the range of 50 ms to 2 s or in the range of 100 ms to 1500 ms. Two consecutive elements may be switched ON and OFF in successive or overlapping method. Additionally, the delivery of the radiofrequency energy by two consecutive active elements may be separated by the time of no or low radiofrequency stimulation, such that non of the two consecutive active elements provides a radiofrequency heating of the treatment tissue. The time of no or low radiofrequency stimulation may be in the range of 1 us to 1000 ms, or in the range of 500 us to 500 ms or in the range of 1 ms to 300 ms or in the range of 10 ms to 250 ms.

In case of the treatment when more than one pad is used, the sequential switching of the active elements providing radiofrequency treatment may be provided within each pad independently of the other pads or active elements may deliver energy sequentially through all pads.

As an example for three dependent pads, each with two active elements:
first step—the radiofrequency may be provided by active element one in the first pad, wherein other active elements are turned off,
second step—the active element two of the first pad is turned on and the rest of the active elements are turned off,
third step—the active element one of the second pad is turned on and the rest of the active elements are turned off,
fourth step—the active element two of the second pad is turned on and the rest of the active elements are turned off,
fifth step—the active element one of the third pad is turned on and the rest of the active elements are turned off,
sixth step—the active element two of the third pad is turned on and the rest of the active elements are turned off Another non-limiting example may be:
first step—the radiofrequency may be provided by active element one in the first pad, wherein other active elements are turned off,
second step—the active element one of the second pad is turned on and the rest of the active elements are turned off,
third step—the active element one of the third pad is turned on and the rest of the active elements are turned off,
fourth step—the active element two of the first pad is turned on and the rest of the active elements are turned off,
fifth step—the active element two of the second pad is turned on and the rest of the active elements are turned off,
sixth step—the active element two of the third pad is turned on and the rest of the active elements are turned off.

In case that the pads are treating pair areas (e.g. cheeks, thighs or buttocks), where symmetrical effect is desired, the pair pads may be driven by the same protocol at the same time.

An example of treatment protocol for one pad delivering the radiofrequency energy for heating of the patient and the electric current causing the muscle contractions is as follow. The protocol may include a first section where electrodes in one pad may be treated such that the electrodes provide an electric current pulses modulated in an envelope of increasing amplitude modulation (increasing envelope) followed by constant amplitude (rectangle envelope) followed by decreasing amplitude modulation (decreasing envelope), all these three envelopes may create together a trapezoidal amplitude modulation (trapezoidal envelope). The trapezoidal envelope may last 1 to 10 seconds or 1.5 to 7 seconds or 2 to 5 seconds. The increasing, rectangle, or decreasing envelope may last for 0.1 to 5 seconds or 0.1 to 4 seconds or 0.1 to 3 seconds. The increasing and decreasing envelope may last for the same time, thus creating a symmetrical trapezoid envelope. Alternatively, the electric current may be modulated to a sinusoidal envelope or rectangular envelope or triangular envelope. The respective envelopes causing muscle contractions may be separated by time of no or low current stimulation, such that no muscle contraction is achieved or by a radiofrequency energy causing the heating of the tissue. During this time of no muscle contraction, the pressure massage by suction openings may be provided, which may cause the relaxation of the muscles. The first section may be preprogrammed such that electrodes on various places of the pad may be switched in time to provide alternating current pulses wherein some other electrodes in the pad may not provide any alternating current pulses but only RF pulses causing heating of the tissue. All electrodes in the pad may ensure providing (be switched by the switching circuitry 14 to provide) RF pulses for heating the tissue during the section of protocol or protocol, while only a limited amount of the electrodes may provide (be switched by the switching circuitry 14 to provide) alternating currents for muscle contracting during the section of protocol or protocol. The device may be configured such that the first section lasts for 1-5 minutes.

A second section may follow the first section. The second section may be preprogrammed such that different electrodes than the ones used in the first section on various places of the pad may be switched in time to provide alternating current pulses wherein some other electrodes (same or different electrodes than the ones used in the first section) in the pad may not provide any alternating current pulses but only RF pulses causing heating of the tissue.

A third section may follow the second section. The third section may be preprogrammed such that different electrodes than the ones used in the second section on various places of the pad may be switched in time to provide alternating current pulses wherein some other electrodes (same or different electrodes than the ones used in the second section) in the pad may not provide any alternating current pulses but only RF pulses causing heating of the tissue.

The protocol may be preprogrammed such, that the electrodes providing the electric current causing the muscle contractions are switched to provide radiofrequency heating after they produce one, two, three, four or five contractions on maximum.

The respective sections are assembled by the control unit (CPU) in the treatment protocol to provide at least 60-900 contractions or 90-800 contractions, or 150-700 contractions by a single pad.

Figure 9:
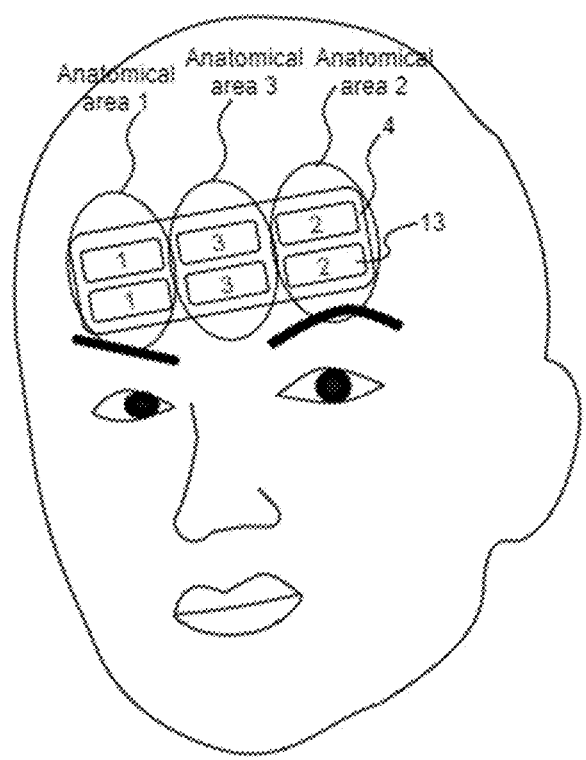
FIG. 9 is an illustration of forehead applicator.

The forehead pad may include a layout of electrodes such that the anatomical area 1 and anatomical area 2 are stimulated by alternating currents which may cause muscle contractions while anatomical area 3 is not stimulated by alternating electric causing muscle contraction. The control unit (CPU) is configured to provide a treatment protocol energizing by alternating electric currents only those electrodes located in proximity or above the anatomical area 1 and 2; and energizing electrode/electrodes in proximity of or above anatomical area 3 by radiofrequency signal only as shown in FIG. 9. The anatomical area 1 and 2 may comprise the Frontalis muscles and the anatomical area 3 may comprise the center of the Procerus muscle.

The pad used for a treatment of the cheek (either side of the face below the eye) may include a layout of electrodes such that the anatomical area comprising the Buccinator muscle, the Masseter muscle, the Zygomaticus muscles or the Risorius muscle are stimulated by electrical currents, which may cause muscle contractions, wherein the other anatomical area may be only heated by the radiofrequency energy.

On the contrary the pad may be configured such, that the layout of electrodes close to the eyes (e.g. body part comprising Orbicularis oculi muscles) or teeth (e.g. body part comprising Orbicularis oris muscles) may not provide energy causing the muscle contractions.

The treatment device may be configured such, that in each section or step the impedance sensor provides the information about the contact of the pad or active element with the patient to the CPU. The CPU may determine based on the pre-set conditions if the contact of the pad or active element with the patient is sufficient or not. In case of sufficient contact, the CPU may allow the treatment protocol to continue. In case that the contact is inappropriate, the valuated pad or active element is turned off and the treatment protocol continues to consecutive pad or active element or the treatment is terminated. The determination of proper contact of the pad or active element may be displayed on the human machine interface 8.

The impedance measurement may be made at the beginning of the section/step, during the section/step or at the end of the section/step. The impedance measurement and/or the proper contact evaluation may be determined only on the active electrodes for the given section/step or may be made on all electrodes of all pads used during the section/step.

Figure 6:
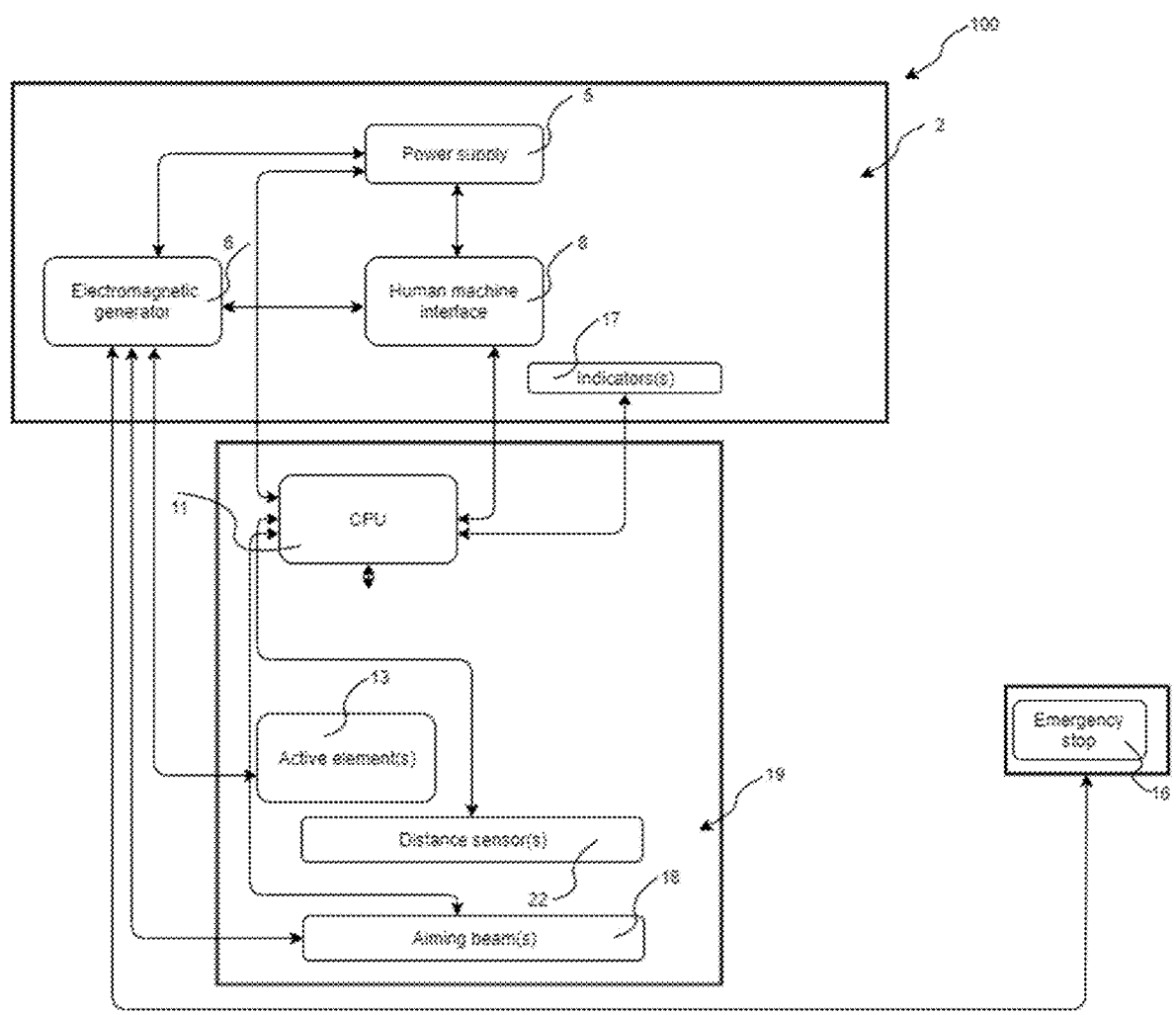
FIG. 6 shows a block diagram of an apparatus for contactless therapy.
Figure 7:
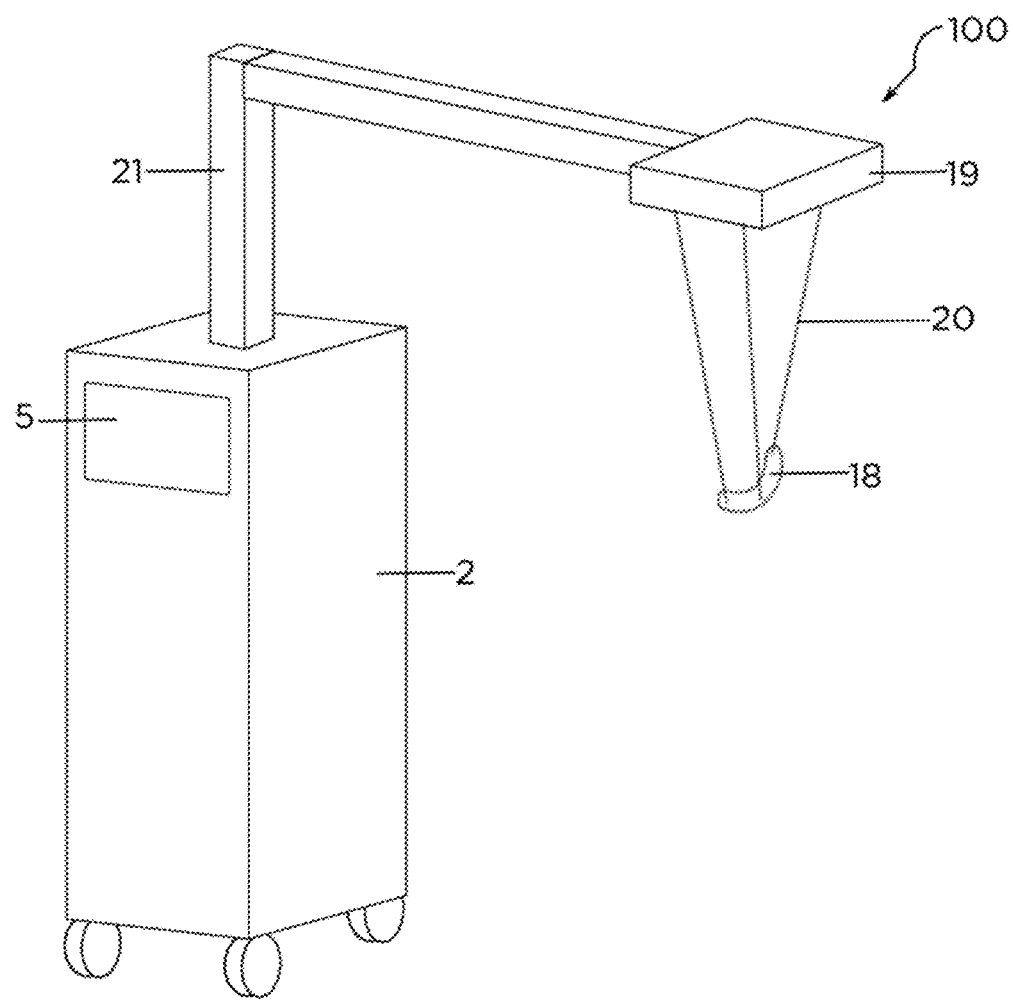
FIG. 7 is an illustration of an apparatus for contactless therapy.

FIG. 6 and FIG. 7 are discussed together. FIG. 6 shows a block diagram of an apparatus for contactless therapy 100. FIG. 7 is an illustration of an apparatus for contactless therapy 100. Apparatus for contactless therapy 100 may comprise two main blocks: main unit 2 and a delivery head 19 interconnected via fixed or adjustable arm 21.

Main unit 2 may include electromagnetic generator 6 which may generate one or more forms of electromagnetic radiation wherein the electromagnetic radiation may be e.g., in the form of incoherent light or in the form of coherent light (e.g. laser light) of predetermined wavelength. The electromagnetic field may be primarily generated by a laser, laser diode module, LED, flash lamp or incandescent light bulb. The electromagnetic radiation may be such that it may be at least partially absorbed under the surface of the skin of the patient. The wavelength of the applied radiation may be in the range of 100 to 15000 nm or in the range of 200 to 12000 nm or in the range of 300 to 11000 nm or in the range of 400 to 10600 nm or it may be in the form of second, third, fourth, fifth, sixth, seventh or eighth harmonic wavelengths of the above mentioned wavelength ranges. Main unit 2 may further comprise a human machine interface 8 represented by display, buttons, keyboard, touchpad, touch panel or other control members enabling an operator to check and adjust therapy and other device parameters. The power supply 5 located in the main unit may include a transformer, disposable battery, rechargeable battery, power plug or standard power cord. The output power of the power supply 5 may be in the range of 10 W to 600 W, or in the range of 50 W to 500 W, or in the range of 80 W to 450 W. Indicators 17 may provide additional information about the current status of the device independently on human machine interface 8. Indicators 17 may be realized through the display, LEDs, acoustic signals, vibrations or other forms capable of adequate notice.

Delivery head 19 may be interconnected with the main unit via arm 21 which may form the main optical and electrical pathway. Arm 21 may comprise transmission media, for example wires or waveguide, e.g. mirrors or fiber optic cables, for electromagnetic radiation in the form of light or additional electric signals needed for powering the delivery head 19. The CPU 11 controls the electromagnetic generator 6 which may generate a continuous electromagnetic energy (CM) or a pulses, having a fluence in the range of 0.1 pJ/cm$^2$ to 1000 J/cm$^2$ or in the range of 0.5 pJ/cm$^2$ to 800 J/cm$^2$ or in the range of 0.8 pJ/cm$^2$ to 700 J/cm$^2$ or in the range of 1 pJ/cm$^2$ to 600 J/cm$^2$ on the output of the electromagnetic generator. The CM mode may be operated for a time interval in the range of 0.1 s to 24 hours or in the range of 0.2 s to 12 hours or in the range of 0.5 s to 6 hours or in the range of 1 s to 3 hours. The pulse duration of the electromagnetic radiation operated in the pulse regime may be in the range of 0.1 fs to 2000 ms or in the range of 0.5 fs to 1500 ms or in the range of 1 fs to 1200 ms or in the range of 1 fs to 1000 ms. Alternatively the pulse duration may be in the range of 0.1 fs to 1000 ns or in the range of 0.5 fs to 800 ns or in the range of 1 fs to 500 ns or in the range of 1 fs to 300 ns. Alternatively, the pulse duration may be in the range of 0.3 to 5000 ps or in the range of 1 to 4000 ps or in the range of 5 to 3500 ps or in the range of 10 to 3000 ps. Or alternatively the pulse duration may be in the range of 0.05 to 2000 ms or in the range of 0.1 to 1500 ms or in the range of 0.5 to 1250 ms or in the range of 1 to 1000 ms. The electromagnetic generator 6 in the pulse regime may be operated by CPU 11 in a single shot mode or in a repetition mode or in a burst mode. The frequency of the repetition mode or the burst mode may be in the range of 0.05 to 10 000 Hz or in the range of 0.1 to 5000 Hz or in the range of 0.3 to 2000 Hz or in the range of 0.5 to 1000 Hz. Alternatively the frequency of the repetition mode or the burst mode may be in the range of 0.1 kHz to 200 MHz or in the range of 0.5 kHz to 150 MHz or in the range of 0.8 kHz to 100 MHz or in the range of 1 kHz to 80 MHz. The single shot mode may be configured to generate a single electromagnetic energy of specific parameters (e.g. intensity, duration, etc.) for irradiation of a single treatment area. The repetition mode may be configured to generate an electromagnetic energy, which may have one or more specific parameters (e.g. intensity, duration, etc.), with a repetition rate of the above-mentioned frequency for irradiation of a single treatment area. The burst mode may be configured to generate multiple consecutive electromagnetic energys, which may have variable parameters (e.g. intensity, duration, delay etc.), during one sequence, wherein the sequences are repeated with the above-mentioned frequency and wherein the sequence may include the same or different sets of consecutive electromagnetic energys.

Alternatively, the device may contain more than one electromagnetic generator 6 for generation of the same or a different electromagnetic energy, e.g. one electromagnetic generator is for generation of an ablative electromagnetic energy and the other is for generation of a non-ablative electromagnetic energy. In this case, it is possible for an operator to select which electromagnetic generators may be used for a given treatment or the clinician can choose a required treatment through the human machine interface 8 and the CPU 11 will select which electromagnetic generators will be used. It is possible to operate one or more electromagnetic generators of the device 100 simultaneously, successively or in an overlapping method. For example in the case of two electromagnetic generators: in the simultaneous method, both electromagnetic generators are used simultaneously during a time interval e.g., 1-20 ps. In the successive method, the first electromagnetic generator is used during the first time interval e.g., from 1 to 10 ps. The first electromagnetic generator is then stopped and the second electromagnetic generator is immediately used in a subsequent time interval e.g., from 10 to 20 ps. Such a sequence of two or more successive steps may be repeated. In the overlapping method, the first electromagnetic generator is used during a time interval, e.g., 1-10 ps, and the second electromagnetic generator is used in a second overlapping time interval for e.g., 2-11 ps, wherein during the second time interval the first electromagnetic generator and the second electromagnetic generator are overlapping e.g., with total overlapping method time for 2-10 ps. In the case of more than two electromagnetic generators, the activating and deactivating of the electromagnetic generators in a successive or overlap method may be driven by CPU 11 in the order which is suitable for a given treatment, e.g. first activating the pre-heating electromagnetic generator, then the ablation electromagnetic generator and then the non-ablative electromagnetic generator.

The active elements 13 in the delivery head 19 may be in the form of optical elements, which may be represented by one or more optical windows, lenses, mirrors, fibers or diffraction elements. The optical element representing active element 13 may be connected to or may contain electromagnetic generator 6 inside the delivery head 19. The optical element may produce one beam of electromagnetic energy, which may provide an energy spot having an energy spot size defined as a surface of tissue irradiated by one beam of light. One light generator may provide one or more energy spots e.g. by splitting one beam into a plurality of beams. The energy spot size may be in the range of 0.001 $cm^2$ to 1000 $cm^2$, or in the range of 0.005 $cm^2$ to 700 $cm^2$, or in the range of 0.01 $cm^2$ to 300 $cm^2$, or in the range of 0.03 $cm^2$ to 80 $cm^2$. Energy spots of different or the same wavelength may be overlaid or may be separated. Two or more beams of light may be applied to the same spot at the same time or with a time gap ranging from 0.1 μs to 30 seconds. Energy spots may be separated by at least 1% of their diameter, and in addition, energy spots may closely follow each other or may be separated by a gap ranging from 0.01 mm to 20 mm or from 0.05 mm to 15 mm or from 0.1 mm to 10 mm.

The CPU 11 may be further responsible for switching between active elements 13 or for moving the active elements 13 within the delivery head 19 so that the electromagnetic radiation may be delivered homogeneously into the whole treatment area marked with aiming beam 18. The rate of switching between active elements 13 may be dependent on the amount of delivered energy, pulse length, etc. and the speed of CPU 11 or other mechanism responsible for switching or moving the active elements 13 (e.g. scanner). Additionally, a device may be configured to switch between multiple active elements 13 in such a way that they deliver energy simultaneously, successively or in an overlapping method. For example, in the case of two active elements: in the simultaneous method, both active elements are used simultaneously during the time interval e.g., 1-20 ps. In the successive method, the first active element is used during the first time interval e.g., from 1 to 10 ps. The first active element is then stopped and the second active element is immediately used in a subsequent time interval e.g., from 10 to 20 ps. This successive step may be repeated. In the overlapping method, the first active element is used during a time interval for e.g., 1-10 ps, and the second active element is used in a second overlapping time interval for e.g., 2-11 ps, wherein during the second time interval the first active element and the second active element are overlapping e.g., with total overlapping method time for 2-10 ps.

The aiming beam 18 has no clinical effect on the treated tissue and may serve as a tool to mark the area to be treated so that the operator knows which exact area will be irradiated and the CPU 11 may set and adjust treatment parameters accordingly. An aiming beam may be generated by a separate electromagnetic generator or by the primary electromagnetic generator 6. Aiming beam 18 may deliver energy at a wavelength in a range of 300-800 nm and may supply energy at a maximum power of 10 mW.

In addition, the pad may contain a CPU 11 driven distance sensor 22 for measuring a distance from active element 13 to the treated point within the treated area marked by aiming beam 18. The measured value may be used by CPU 11 as a parameter for adjusting one or more treatment parameters which may depend on the distance between an electromagnetic generator and a treating point, e.g. fluence. Information from distance sensor 22 may be provided to CPU 11 before every switch/movement of an active element 13 so that the delivered energy will remain the same across the treated area independent of its shape or unevenness.

The patient's skin may be pre-cooled to a selected temperature for a selected duration over at least one treatment portion, the selected temperature and duration for pre-cooling preferably being sufficient to cool the skin to at least a selected temperature below normal body temperature. The skin may be cooled to at least the selected temperature to a depth below the at least one depth for the treatment portions so that the at least one treatment portion is substantially surrounded by cooled skin. The cooling may continue during the application of radiation, wherein the duration of the application of radiation may be greater than the thermal relaxation time of the treatment portions. Cooling may be provided by any known mechanism including water cooling, sprayed coolant, presence of an active solid cooling element (e.g. thermoelectric cooler) or air flow cooling. A cooling element may act as an optical element. Alternatively, a spacer may serve as a cooling element. Cooling may be provided during, before or after the treatment with electromagnetic energy. Cooling before treatment may also provide an environment for sudden heat shock, while cooling after treatment may provide faster regeneration after heat shock. The temperature of the coolant may be in the range of −200° C. to 36° C. The temperature of the cooling element during the treatment may be in the range of −80° C. to 36° C. or −70° C. to 35° C. or −60° C. to 34° C. Further, where the pad is not in contact with the patient's skin, cryogenic spray cooling, gas flow or other non-contact cooling techniques may be utilized. A cooling gel on the skin surface might also be utilized, either in addition to or instead of, one of the cooling techniques indicated above.

Additionally, device 100 may include one or more sensors. The sensor may provide information about at least one physical quantity and its measurement may lead to feedback which may be displayed by human machine interface 8 or indicators 17. The one or more sensors may be used for sensing a variety of physical quantities, including but not limited to the energy of the delivered electromagnetic radiation or backscattered electromagnetic radiation from the skin, impedance of the skin, resistance of the skin, temperature of the treated skin, temperature of the untreated skin, temperature of at least one layer of the skin, water content of the device, the phase angle of delivered or reflected energy, the position of the active elements 13, the position of the delivery element 19, temperature of the cooling media or temperature of the electromagnetic generator 6. The sensor may be a temperature, acoustic, vibration, electric, magnetic, flow, positional, optical, imaging, pressure, force, energy flux, impedance, current, Hall or proximity sensor. The sensor may be a capacitive displacement sensor, acoustic proximity sensor, gyroscope, accelerometer, magnetometer, infrared camera or thermographic camera. The sensor may be invasive or contactless. The sensor may be located on the delivery element 19 or in the main unit 2 or may be a part of a distance sensor 22. One sensor may measure more than one physical quantity. For example, a sensor may include a combination of a gyroscope, an accelerometer or a magnetometer. Additionally, the sensor may measure one or more physical quantities of the treated skin or untreated skin.

The temperature sensor measures and monitors the temperature of the treated skin. The temperature can be analyzed by a CPU 11. The temperature sensor may be a contactless sensor (e.g. infrared temperature sensor). The CPU 11 may also use algorithms to calculate a temperature below the surface of the skin based on the surface temperature of the skin and one or more additional parameters. A temperature feedback system may control the temperature and based on set or pre-set limits alert the operator in human perceptible form e.g. on the human machine interface 8 or via indicators 17. In a limit temperature condition, the device may be configured to adjust treatment parameters of each active element, e.g. output power, activate cooling or stop the treatment. Human perceptible form may be a sound, alert message shown on human machine interface 8 or indicators 17 or change of color of any part of the device 100.

A resistance sensor may measure the skin resistance, since it may vary for different patients, as well as the humidity—wetness and sweat may influence the resistance and therefore the behavior of the skin in the energy field. Based on the measured skin resistance, the skin impedance may also be calculated.

Information from one or more sensors may be used for generation of a pathway on a convenient model e.g. a model of the human body shown on a display of human machine interface 8. The pathway may illustrate a surface or volume of already treated tissue, presently treated tissue, tissue to be treated, or untreated tissue. A convenient model may show a temperature map of the treated tissue providing information about the already treated tissue or untreated tissue.

The sensor may provide information about the location of bones, inflamed tissue or joints. Such types of tissue may not be targeted by electromagnetic radiation due to the possibility of painful treatment. Bones, joints or inflamed tissue may be detected by any type of sensor such as an imaging sensor (ultrasound sensor, IR sensor), impedance and the like. A detected presence of these tissue types may cause general human perceptible signals or interruption of generation of electromagnetic radiation. Bones may be detected for example by a change of impedance of the tissue or by analysis of reflected electromagnetic radiation.

Furthermore, the device 100 may include an emergency stop button 16 so that the patient can stop the therapy immediately anytime during the treatment.

It may be part of the invention that the method of treatment includes the following steps: preparation of the tissue; positioning the proposed device; selecting or setting up the treatment parameters; and application of the energy. More than one step may be executed simultaneously.

Preparation of the tissue may include removing make-up or cleansing the patient's skin. For higher target temperatures, anesthetics may be applied topically or in an injection.

Positioning the device may include selecting the correct shape of the pad according to the area to be treated and affixing the pad or the neutral electrode to the patient, for example with an adhesive layer, vacuum suction, band or mask, and verifying proper contact with the treated tissue in the case of contact therapy. In the case of contactless therapy, positioning of the device may include adjusting the aiming beam of proposed device so that the device can measure the distance of the active element(s) from the treatment area and adjust the treatment parameters accordingly.

Selecting or setting up the treatment parameters may include adjusting treatment time, power, duty cycle, delivery time and mode (CM or pulsed), active points surface density/size for fractional arrangement and mode of operation. Selecting the mode of operation may mean choosing simultaneous, successive or overlapping methods or selecting the switching order of active elements or groups of active elements or selecting the proper preprogrammed protocol.

Application of the energy may include providing at least one type of energy in the form of RF energy, ultrasound energy or electromagnetic energy in the form of polychromatic or monochromatic light, or their combination. The energy may be provided from at least one active element into the skin by proposed device. Energy may be delivered and regulated automatically by the CPU according to information from temperature sensors and impedance measurements and, in the case of contactless therapy, distance sensors. All automatic adjustments and potential impacts on the therapy may be indicated on the device display. Either the operator or the patient may suspend therapy at any time during treatment. A typical treatment might have a duration of about 1 to 60 min or 2 to 50 min or 3 to 40 min per pad depending on the treated area and the size and number of active elements located within the pad.

In one example, application of energy to the tissue may include providing radiofrequency energy or ultrasound energy or their combination, from the active elements embedded in the pad, to the skin of the patient. In such case, active elements providing radiofrequency energy may be dielectric and capacitive or resistive RF electrodes and the RF energy may cause heating, coagulation or ablation of the skin. Ultrasound energy may be provided through an acoustic window and may rise the temperature in the depth which may suppress the gradient loss of RF energy and thus the desired temperature in a germinal layer may be reach. In addition, the RF electrode may act as an acoustic window for ultrasound energy.

Alternatively, the application of the energy to the tissue may include providing electromagnetic energy in the form of polychromatic or monochromatic light from the active elements into the skin of the patient. In such case, active elements providing the electromagnetic energy may comprise optical elements described in the proposed device. Optical elements may be represented by an optical window, lens, mirror, fiber or electromagnetic field generator, e.g. LED, laser, flash lamp, incandescent light bulb or other light sources known in the state of art. The electromagnetic energy in the form of polychromatic or monochromatic light may entail the heating, coagulation or ablation of the skin in the treated area.

After reaching the required temperature and therapy time the therapy is terminated, the device accessories may be removed and a cleansing of the patient's skin may be provided.

The invention claimed is:
1. A device for a treatment of a patient, comprising:
a pad comprising an electrode, wherein the pad and the electrode are configured to be attached to a body part of a patient during a treatment, and wherein the body part comprises one of a face, a neck, or a submentum,
wherein the electrode is configured to apply radiofrequency energy in a range of 400 kHz to 80 MHz to the body part of the patient, thereby causing radiofrequency heating of skin of the body part to a temperature in a range of 37.5° C. to 65° C.,
wherein the electrode is configured to apply a pulsed electric current with a duration in a range of 0.1 μs to 10 s to the body part, thereby causing an electric muscle stimulation of a muscle within the body part, and
wherein the electrode is configured to provide the radiofrequency heating and the electric muscle stimulation during the treatment; and a control unit configured to control the radiofrequency energy and the pulsed electric current.

2. The device of claim 1, wherein the control unit is configured to modulate amplitudes of pulses of the pulsed electric current to create an increasing envelope of consecutive pulses of the pulsed electric current, followed by a rectangular envelope of consecutive pulses of the pulsed electric current, followed by a decreasing envelope of consecutive pulses of the pulsed electric current.

3. The device of claim 2, wherein the at least one of the increasing, the decreasing, or the rectangular envelope of the pulsed electric current lasts for a time duration in a range of 0.1 seconds to 5 seconds.

4. The device of claim 1, wherein the control unit is configured to modulate the amplitudes of pulses of the pulsed electric current to create a trapezoidal envelope of consecutive pulses of the pulsed electric current.

5. The device of claim 4, wherein the trapezoidal envelope of the pulsed electric current lasts for a time duration in a range of 1 second to 10 seconds.

6. The device of claim 5, wherein the electrode is configured to provide the radiofrequency energy and the pulsed electric current sequentially.

7. The device of claim 6, wherein the electrode applies the radiofrequency energy in pulses with a radiofrequency energy pulse duration in a range of 0.1 ms to 10 s.

8. A device for a treatment of a patient, comprising:
a pad comprising an electrode, wherein the pad is flexible and configured to be attached to a body part of a patient during a treatment, and wherein the body part comprises one of a face, a neck, or a submentum,
wherein the electrode is configured to be coupled to the body part,
wherein the electrode is configured to apply radiofrequency energy to the body part, thereby causing radiofrequency heating of skin of the body part during the treatment, and
wherein the electrode is configured to apply a pulsed electric current with a pulse duration in a range of 0.5 us to 500 ms to the body part, thereby causing a contraction of a muscle within the body part during the treatment; and
a control unit comprising a central processing unit, the control unit configured to control the radiofrequency energy and the pulsed electric current.

9. The device of claim 8, wherein the pulsed electric current has a frequency in a range of 0.5 Hz to 1 kHz.

10. The device of claim 9, further comprising an adhesive coupled to the electrode, wherein the adhesive is configured to provide attachment of the electrode to the body part, and wherein the electrode is configured to be in contact with the body part via the adhesive.

11. The device of claim 8, wherein the control unit is configured to modulate amplitudes of pulses of the pulsed electric current to create a trapezoidal envelope comprising an increasing part, a constant part, and a decreasing part, and
wherein a time duration of the trapezoidal envelope is in a range of 1 second to 10 seconds.

12. The device of claim 11, further comprising a sensor configured to obtain information indicative of contact between the electrode and the body part and to provide the information to the control unit, wherein the information comprises impedance of the electrode or the body part.

13. The device of claim 10, further comprising a user interface,
wherein the control unit further comprises a memory having a preprogramed treatment protocol stored thereon,
wherein the user interface is configured to allow a selection of the preprogrammed treatment protocol,
wherein the preprogrammed treatment protocol comprises a set of parameters of the radiofrequency energy and the pulsed electric current, and
wherein the control unit is configured to execute the treatment based on the preprogrammed treatment protocol.

14. The device of claim 13, wherein the preprogrammed treatment protocol is configured to induce 60 to 900 contractions of the muscle by the pad during the treatment.

15. The device of claim 8, wherein the control unit is configured to modulate amplitudes of pulses of the pulsed electric current to create at least one of an increasing envelope followed by a rectangular envelope, a rectangular envelope followed by a decreasing envelope, or an increasing envelope followed by a decreasing envelope of the pulsed electric current.

16. A device for treating a patient by radiofrequency energy and a pulsed electric current, the device comprising:
a flexible pad configured to be attached to a body part of a patient, the flexible pad comprising:
a flexible substrate comprising an underside configured to face the body part during a treatment;
an electrode coupled to the underside of the flexible substrate; and
an adhesive coupled to the underside of the flexible substrate and to the electrode,
wherein the electrode is configured to be in contact with the body part via the adhesive;
wherein the electrode is configured to apply radiofrequency energy to the body part to cause heating of the body part, and
wherein the electrode is configured to apply pulsed electric current to the body part to cause a muscle contraction of a muscle within the body part; and
a control unit configured to control the radiofrequency energy and the pulsed electric current to provide the heating and the muscle contraction of the body part during the treatment,
wherein the body part comprises one of a face, a neck, or a submentum.

17. The device of claim 16, wherein the control unit is configured to modulate amplitudes of pulses of the pulsed electric current to create a trapezoidal envelope of consecutive pulses of the pulsed electric current.

18. The device of claim 17, wherein the flexible pad is configured to cover at least partially one or more of a periorbital area, a forehead, a jaw line, a perioral area, a left cheek, a right cheek, a neck, or a submentum of the patient.

19. The device of claim 18, wherein the flexible pad is configured to cover at least partially the forehead of the patient, and wherein the pulsed electric current causes a contraction of a frontalis muscle.

20. The device of claim 18, wherein the flexible pad is configured to cover at least partially the left cheek or the right cheek of the patient, and wherein the pulsed electric current causes a contraction of at least one of a buccinators muscle, masseter muscle, zygomaticus muscle, or risorius muscle.

21. The device of claim 18, further comprising a second flexible pad configured to be attached to the body part of the patient, the second flexible pad comprises:

a second flexible substrate comprising a underside configured to face the body part during a treatment;

a second electrode coupled to the underside of the second flexible substrate; and a second adhesive coupled to the underside of the second flexible substrate and to the second electrode, wherein the second electrode is configured to be in contact with the body part via the second adhesive, wherein the second electrode is configured to apply the radiofrequency energy to the body part to cause heating of the body part, wherein the second electrode is configured to apply the pulsed electric current to the body part to cause a second muscle contraction of a second muscle within the body part, and wherein the control unit is configured to control the radiofrequency energy and the pulsed electric current to provide the heating, the muscle contraction, and the second muscle contraction of the body part during the treatment.

22. The device of claim 21, wherein the control unit is configured to control the pulsed electric current to provide 60 to 900 contractions of the muscle or the second muscle per treatment.

* * * * *